United States Patent
Koppitz et al.

(10) Patent No.: US 10,167,293 B2
(45) Date of Patent: Jan. 1, 2019

(54) [8-(PHENYLSULFONYL)-3,8-DIAZABICYCLO[3.2.1]OCT-3-YL] (1H-1,2,3-TRIAZOL-4-YL)METHANONES

(71) Applicant: BAYER PHARMA AKTIENGESELLSCHAFT, Berlin (DE)

(72) Inventors: Marcus Koppitz, Berlin (DE); Holger Siebeneicher, Berlin (DE); Holger Steuber, Berlin (DE); Antonius Ter Laak, Berlin (DE); Reinhard Nubbemeyer, Berlin (DE); Antje Rottmann, Berlin (DE); Horst Irlbacher, Berlin (DE); Benjamin Bader, Berlin (DE); Michaele Peters, Berlin (DE); Andrea Wagenfeld, Berlin (DE); Ildiko Terebesi, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/596,383

(22) Filed: May 16, 2017

(65) Prior Publication Data

US 2017/0342082 A1 Nov. 30, 2017
US 2018/0319807 A2 Nov. 8, 2018

(30) Foreign Application Priority Data

May 26, 2016 (EP) ..................... 16171538
Jul. 11, 2016 (EP) ..................... 16178891

(51) Int. Cl.
C07D 487/08 (2006.01)
A61K 31/4995 (2006.01)
A61K 45/06 (2006.01)

(52) U.S. Cl.
CPC ........ C07D 487/08 (2013.01); A61K 31/4995 (2013.01); A61K 45/06 (2013.01)

(58) Field of Classification Search
CPC ... C07D 487/08; A61K 31/4995; A61K 45/06
See application file for complete search history.

(56) References Cited

U.S. PATENT DOCUMENTS 6,541,463 B1  4/2003  Labrie et al.

FOREIGN PATENT DOCUMENTS

| WO | 2007/103456 | 9/2007 | |
| WO | 2007/111921 | 10/2007 | |
| WO | WO 2007/111921 | * 10/2007 | ........... C07D 295/22 |
| WO | 2007/124423 | 11/2007 | |
| WO | 2008/024284 | 2/2008 | |
| WO | 2013/045407 | 4/2013 | |
| WO | 2013/059245 | 4/2013 | |
| WO | 2013/142390 | 9/2013 | |
| WO | 2014/009274 | 1/2014 | |
| WO | 2014/039820 | 3/2014 | |
| WO | 2014/128108 | 8/2014 | |

OTHER PUBLICATIONS

West, Anthony R., Solid State Chemistry and Its Applications, Wiley, New York, 1988, 358.*
Heinrich et al. "Synthesis and structure-activity relationships for 1-(4-(piperidin-1-ylsulfonyl)phenyl)pyrrolidin-2-ones as novel non-carboxylate inhibitors of the aldo-keto reductase enzyrne AKR1C3" Eur. J. Med. Chem. 62:738-744 (2013).
Jamieson et al. "3-(3,4-Dihydroisoquinolin-2(1H)-ylsulfonyl)benzoic acids: Highly Potent and selective inhibitors of the type 5 17-β-hydroxysteroid dehydrogenase AKR1C3" J. Med. Chem. 55:7746-7758 (2012).
Adeniji et al. "AKR1C3 as a target in castrate resistant prostate cancer" J. Steroid Biochem. Mol. Biol. 137:136-149 (2013).
Azzarello et al. "Expression of AKR1C3 in renal cell carcinoma, papillary urothelial carcinoma, and Wilms' tumor" Int'l J. Clin. Exp. Pathol. 3:147-155 (2010).
Azziz et al. "Criteria for defining polycystic ovary syndrome as a predominantly hyper-androgenic syndrome: An androgen excess society guideline" J. Clin. Endocrinol. Metab. 91:4237-4245 (2006).
Bains et al. "Naturally occurring variants of human aldo-keto reductases with reduced in vitro metabolism of daunorubicin and doxorubicin" J. Pharmacol. Exper. Therapeut. 335:533-545 (2010).
Barr et al. "The release of prostaglandin D2 from human skin in vivo and in vitro during immediate allergic reactions" Br. J. Pharmacol. 94:773-780 (1988).

(Continued)

Primary Examiner — Erich A Leeser
(74) Attorney, Agent, or Firm — Nixon & Vanderhye P.C.

(57) ABSTRACT

The present invention covers [8-(phenylsulfonyl)-3,8-diazabicyclo[3.2.1]oct-3-yl](1H-1,2,3-triazol-4-yl)methanone compounds of general formula (I):

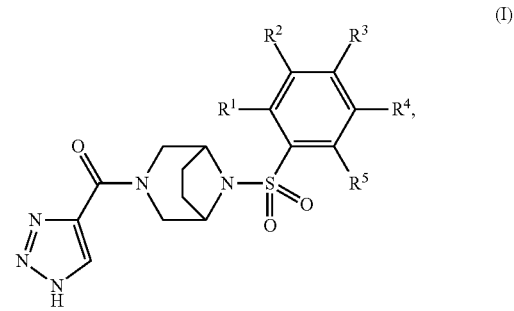

in which $R^1$, $R^2$, $R^3$, $R^4$ and $R^5$ are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of disorders, in particular of gynecological disorders, hyperproliferative disorders, metabolic disorders, or inflammatory disorders as a sole agent or in combination with other active ingredients.

18 Claims, 2 Drawing Sheets

(56) References Cited

OTHER PUBLICATIONS

Berge et al. "Pharmaceutical salts" J. Pharmaceut. Sci. 66:1-19 (1977).

Birtwistle et al. "The aldoketo reductase AKR1C3 contributes to 7,12-dimethylbenz(a)-anthracene-3,4-dihydrodiol mediated oxidative DNA damage in myeloid cells: Implications for leukemogenesis" Mutation Res. 662:67-74 (2009).

Byrns et al. "Aldoketo reductase 1C3 expression in MCF7 cells reveals roles in steroid hormone and prostaglandin metabolism that may explain its overexpression in breast cancer" J. Steroid Biochem. Mol. Biol. 118:177-187 (2010).

Cai et al. "Intratumoral de novo steroid synthesis activates androgen receptor in castration-resistant prostate cancer and is upregulated by treatment with CYP17A1 inhibitors" Cancer Res. 71:6503-6513 (2011).

Colombe et al. "Prostaglandin metabolism in human hair follicle" Exper. Dermatol. 16:762-769 (2007).

Dahten et al. "Systemic PPARγ ligation inhibits allergic immune response in the skin" J. Invest. Dermatol. 128:2211-2218 (2008).

Desmond et al. "The aldo-keto reductase AKR1C3 is a novel suppressor of cell differentiation that provides a plausible target for the non-cyclooxygenase-dependent antineoplastic actions of nonsteroidal anti-inflammatory drugs" Cancer Res. 63:505-512 (2003).

Du et al. "KLF15 is a transcriptional regulator of the human 17β-hydroxysteroid dehydrogenase type 5 gene. A potential link between regulation of testosterone production and fat stores in women" J. Clin. Endocrinol. Metab. 94:2594-2601 (2009).

Dufort et al. "Characteristics of a highly labile human type 5 17β-hydroxysteroid dehydrogenase" Endocrinol. 140:568-574 (1999).

Dunaif "Insulin resistance and the polycystic ovary syndrome: Mechanism and implications for pathogenesis" Endocrine Rev. 18:774-800 (1997).

Einspanier et al. "Induction of endometriosis in the marmoset monkey (*Callithrix jacchus*)" Mol. Hum. Reprod. 12:291-299 (2006).

Figueroa et al. "Bladder cancer risk and genetic variation in AKR1C3 and other metabolizing genes" Carcinogenesis 29:1955-1962 (2008).

Flanagan et al. "Morpholylureas are a new class of potent and selective inhibitors of the type 5 17-β-hydroxysteroid dehydrogenase (AKR1C3)" Bioorg. Med. Chem. 22:967-977 (2014).

Franks et al. "Polycystic ovary syndrome: Evidence for a primary disorder of ovarian steroidogenesis" J. Steroid Biochem. Mol. Biol. 69:269-272 (1999).

Fujiwara et al. "Anthracycline antibiotics" Crit. Rev. Biotechnol. 3:133-157 (1985).

Fung et al. "Increased expression of type 2 3α-hydroxysteroid dehydrogenase/type 5 17β-hydroxysteroid dehydrogenase (AKR1C3) and its relationship with androgen receptor in prostate carcinoma" Endocrine-Related Cancer 13:169-180 (2006).

Gavelová et al. "Reduction of doxorubicin and oracin and induction of carbonyl reductase in human breast carcinoma MCF7 cell" ChemicoBiological Interactions 176:9-18 (2008).

Halim et al. "Imaging induction of cytoprotective enzymes in intact human cells: Coumberone, a metabolic reporter for human AKR1c enzymes reveals activation by panaxytriol, an active component of red ginseng" J. Am. Chem. Soc. 130:14123-14128 (2008).

Hamid et al. "Aldo-keto reductase family 1 member C3 (AKR1C3) is a biomarker and therapeutic target for castration-resistant prostate cancer" Mol. Med. 18:1449-1455 (2012).

He et al. "A large-scale candidate gene association study of age at menarche and age at natural menopause" Hum. Genet. 128:515-527 (2010).

Heibein et al. "Role of aldo-keto reductases and other doxorubicin pharmacokinetic genes in doxorubicin resistance, DNA binding, and subcellular localization" BMC Cancer 12:1-14 (2012).

Hofman et al. "Anthracycline resistance mediated by reductive metabolism in cancer cells: The role of aldo-keto reductase 1C3" Toxicol. Appl. Pharmacol. 278:238-248 (2014).

Huhtinen et al. "Endometrial and endometriotic concentrations of estrone and estradiol are determined by local metabolism rather than circulating levels" J. Clin. Endocrinol. Metab. 97:4228-4235 (2012).

Labrie et al. "DHEA and its transformation into androgens and estrogens in peripheral target tissues: Intracrinology" Front. Neuroendocrin. 22:185-212 (2001).

Lan et al. "Oxidative damage-related genes AKR1C3 and OGG1 modulate risks for lung cancer due to exposure to PAH-rich coal combustion emissions" Carcinogenesis 25:2177-2181 (2004).

Lan et al. "Genetic polymorphisms in the oxidative stress pathway and susceptibility to non-Hodgkin lymphoma" Hum. Genet. 121:161-168 (2007).

Legro et al. "Letrozole versus clomiphene for infertility in the polycystic ovary syndrome" N. Engl. J. Med. 371:119-129 (2014).

Liu et al. "Intracrine androgens and AKR1C3 activation confer resistance to enzalutamide in prostate cancer" Cancer Res. 75:1413-1422 (2015).

Loriot et al. "Safety, tolerability and anti-tumour activity of the androgen biosynthesis inhibitor ASP9521 in patients with metastatic castration-resistant prostate cancer: Multi-centre phase I/II study" Invest. New Drugs 32:995-1004 (2014).

Maggi et al. "Anti-inflammtory actions of 15-deoxyΔ$^{12,14}$ prostaglandin J$_2$ and troglitazone evidence for heat shock-dependent and independent inhibition of cytokine-induced inducible nitric oxide synthase expression" Diabetes 49:346-355 (2000).

Maltais et al. "In vitro and in vivo isotope effects with hepatitis c protease inhibitors: Enhanced plasma exposure of deuterated telaprevir versus telaprevir in rats" J. Med. Chem. 52:7993-8001 (2009).

Mani et al. "Diabetes and cardiovascular events in women with polycystic ovary syndrome: A 20-year retrospective cohort study" Clin. Endocrinol. 78:926-934 (2013).

Mantel et al. "Aldo-keto reductase 1C3 Is expressed in differentiated human epidermis, affects keratinocyte differentiation, and is upregulated in atopic dermatitis" J. Invest. Dermatol. 132:1103-1110 (2012).

Mantel et al. "The role of aldo-keto reductase 1C3 (AKR1C3)-mediated prostaglandin D2 (PGD2) metabolism in keloids" Exper. Dermatol. 25:38-43 (2016).

Miller et al. "Aldo-keto reductase family 1 member C3 (AKR1C3) is expressed in adeno-carcinoma and squamous cell carcinoma but not small cell carcinoma" Int'l J. Clin. Exp. Pathol. 5:278-289 (2012).

Morimura et al. "Differential susceptibility of mice humanized for peroxisome proliferator-activated receptor a to Wy-14,643-induced liver tumorigenesis" Carcinogenesis 27:1074-1080 (2006).

Mostaghel et al. "Resistance to CYP17A1 inhibition with abiraterone in castration-resistant prostate cancer: Induction of steroidogenesis and androgen receptor splice variants" Clin. Cancer Res. 17:5913-5925 (2011).

Mutlib et al. "The species-dependent metabolism of efavirenz produces a nephrotoxic glutathione conjugate in rats" Toxicol. Appl. Pharmacol. 169:102-113 (2000).

Novotna et al. "Inactivation of the anticancer drugs doxorubicin and oracin by aldo-keto reductase (AKR) 1C3" Toxicol. Lett. 181:1-6 (2008).

O'Reilly et al. "Hyperandrogenemia predicts metabolic phenotype in polycystic ovary syndrome: The utility of serum androstenedione" J. Endocrinol. Metab. 99:1027-1036 (2014).

O'Reilly et al. "Effect of insulin on AKR1C3 expression in female adipose tissue: In vivo and in-vitro study of adipose androgen generation in polycystic ovary syndrome" Lancet 385 Suppl 1:S16 (2015).

Penning et al. "Aldo-keto reductase (AKR) 1C3: Role in prostate disease and the development of specific inhibitors" Mol. Cell. Endocrinol. 248:182-191 (2006).

Perrin et al. "Stereochemistry of β-deuterium isotope effects on amine basicity" J. Am. Chem. Soc. 127:9641-9647 (2005).

Perrin et al. "Secondary deuterium isotope effects on the acidity of carboxylic acids and phenols" J. Am. Chem. Soc. 129:4490-4497 (2007).

Pfeiffer et al. "Steroidogenic enzymes and stem cell markers are upregulated during androgen deprivation in prostate cancer" Mol. Med. 17:657-664 (2011).

(56) References Cited

OTHER PUBLICATIONS

Pierrou et al. "Expression of genes involved in oxidative stress responses in airway epithelial cells of smokers with chronic obstructive pulmonary disease" Am. J. Respir. Crit. Care Med. 175:577-586 (2007).
Quinkler et al. Androgen generation in adipose tissue in women with simple obesity—A site-specific role for 17β-hydroxysteroid dehydrogenase type 5 J. Endocrinol. 183:331-342 (2004).
Rizner et al. "AKR1C1 and AKR1C3 may determine progesterone and estrogen ratios in endometrial cancer" Mol. Cell. Endocrinol. 248:126-135 (2006).
Roberts et al. "Polymorphisms in genes involved in sex hormone metabolism may increase risk of benign prostatichyperplasia" Prostate 66:392-404 (2006).
Rosman & Taylor "Isotopic compositions of the elements 1997" Pure Appl. Chem. 70:217-235 (1998).
Satoh et al. "Prostaglandin $D_2$ plays an essential role in chronic allergic inflammation of the skin via CRTH2 receptor" J. Immunol. 177:2621-2629 (2006).
Scher et al. "15d-PGD2: The anti-inflammatory prostaglandin?" Clin. Immunol. 114:100-109 (2005).
Schneider et al. "Enhanced plasma concentration by selective deuteration of rofecoxib in rats" Arzneim.-Forsch. Drug Res. 56:295-300 (2006).
Sharma et al. "Nevirapine bioactivation and covalent binding in the skin" Chem. Res. Toxicol. 26:410-421 (2013).
Shimura et al. "Dendritic cells express hematopoietic prostaglandin D synthase and function as a source of prostaglandin D2 in the skin" Am. J. Pathol. 176:227-237 (2010).
Sinreih et al. "Expression of AKR1B1, AKR1C3 and other genes of prostaglandin F2a biosynthesis and action in ovarian endometriosis tissue and in model cell lines" Chemico-Biological Interactions 234 :320-331 (2015).
Smuc et al. "Disturbed estrogen and progesterone action in ovarian endometriosis" Mol. Cell. Endocrinol. 301:59-64 (2009).
Smuc et al. "Expression of 17β-hydroxysteroid dehydrogenases and other estrogen metabolizing enzymes in different cancer cell lines" Chemico-Biological Interactions 178:228-233 (2009).
Spiegelman "Perspective in Diabetes PPAR-γ: Adipogenic regulator and thiazolidinedione receptor" Diabetes 47:507-514 (1998).
Stanbrough et al. "Increased expression of genes converting adrenal androgens to testosterone in androgen-independent prostate cancer" Cancer Res. 66:2815-2825 (2006).
Svensson et al. "Regulation of human aldoketoreductase 1C3 (AKR1C3) gene expression in the adipose tissue" Cell. Mol. Biol. Lett.13:599-613 (2008).
Taponen et al. "Metabolic cardiovascular disease risk factors in women with self-reported symptoms of oligomenorrhea and/or hirsutism: Northern Finland birth cohort 1966 study" J. Clin. Endocrinol. Metabol. 89:2114-2118 (2004).
Tayar et al. "The lipophilicity of deuterium atoms. A comparison of shake-flask and HPLC methods" Int'l J. Pharmaceut. 19:271-281 (1984).
Thoma "Breaking AKR1C3-mediated enzalutamide resistance by inhibiting androgen synthesis" Nat. Rev. Urology 12:124 (2015).
Voon et al. "Correlation of aldo-ketoreductase (AKR) 1C3 genetic variant with doxorubicin pharmacodynamics in Asian breast cancer patients" Br. J. Clin. Pharmacol. 75:1497-1505 (2012).
Wako et al. "Expression of androgen receptor through androgen-converting enzymes is associated with biological aggressiveness in prostate cancer" J. Clin. Pathol. 61:448-454 (2008).
Wenthur et al. "Discovery of (R)-(2-fluoro-4-((-4-methoxyphenyl)ethynyl)phenyl) (3-hydroxypiperidin-1-yl)methanone (ML337), an mGlu3 selective and CNS penetrant negative allosteric modulator (NAM)" J. Med. Chem. 56:5208-5212 (2013).
Yee et al. "Fluorogenic metabolic probes for direct activity readout of redox enzymes: Selective measurement of human AKR1C2 in living cells" Proc. Nat. Acad. Sci. USA 103:13304-13309 (2006).
Yoda et al. "11β-Prostaglandin F2α, a bioactive metabolite catalyzed by AKR1C3, stimulates prostaglandin F receptor and induces slug expression in breast cancer" Mol. Cell. Endocrinol. 413:236e247 (2015).
Yu et al. "Molecular markers in sex hormone pathway genes associated with the efficacy of androgen-deprivation therapy for prostate cancer" PLOS One 8:e54627 (2013).

* cited by examiner

A

B

[8-(PHENYLSULFONYL)-3,8-DIAZABICYCLO [3.2.1]OCT-3-YL](1H-1,2,3-TRIAZOL-4-YL)METHANONES

This application claims priority benefit of EP Application 16171538.8, filed May 26, 2016; and EP Application EP 16178891.4, filed Jul. 11, 2016; the entire contents of each of which are hereby incorporated by reference.

The present invention covers [8-(phenylsulfonyl)-3,8-diazabicyclo[3.2.1]oct-3-yl](1H-1,2,3-triazol-4-yl)methanone compounds of general formula (I) as described and defined herein, methods of preparing said compounds, intermediate compounds useful for preparing said compounds, pharmaceutical compositions and combinations comprising said compounds, and to the use of said compounds for manufacturing a pharmaceutical composition for the treatment or prophylaxis of a disease, in particular in mammals, such as but not limited to gynecological disorders, hyperproliferative disorders, metabolic disorders or inflammatory disorders.

BACKGROUND

The present invention covers [8-(phenylsulfonyl)-3,8-diazabicyclo[3.2.1]oct-3-yl](1H-1,2,3-triazol-4-yl)methanone compounds of general formula (I) which inhibit the enzymatic activity of AKR1C3.

The Aldo-keto reductase family 1 member C3 (AKR1C3 also called type 5 17-beta-hydroxysteroid dehydrogenase (17-beta-HSD5)) is a member of the aldo-keto reductase (AKR) superfamily of enzymes, which reduce the aldehyde/keto group in steroid hormones to the corresponding alcohol and therefore play an important role in androgen-, progesterone-, and estrogene metabolism/activation/deactivation.

AKR1C3 possesses 3α-HSD (hydroxysteroid dehydrogenase activity), 17β-HSD, 20α-HSD and prostaglandin (PG) F synthase activities. It catalyzes the conversion of estrone (weak estrogenic activity) to estradiol (potent estrogenic activity), the conversion of progesterone (potent anti-estrogenic activity) to 20-alpha-hydroxyprogesterone (weak anti-estrogenic activity) and the conversion of androstenedione to testosterone (Labrie et al. Front Neuroendocrinol. 2001, 22(3):185-212). Furthermore AKR1C3 catalyzes the conversion of PGH2 to PGF2α and PGD2 to 11β-PGF2, both known to stimulate inflammation and proliferation. Furthermore AKR1C3 has also been shown to metabolize a broad spectrum of carbonyl compounds and xenobiotics, including clinically administered anthracyclines (Bains et al. J. Pharmacol Exp. Ther. 2010, 335: 533-545; Novona et al. Toxicol Lett. 2008, 181:1-6; Hofman et al. Toxicology and Applied Pharmacology 2014, 278: 238-248).

AKR1C3 plays a role in several pathologic conditions/diseases:

Endometrioses:

Endometriosis is a chronic, mainly estrogen-dependent inflammatory disease characterized by the presence of endometrial tissue outside the uterine cavity. Major symptoms of endometriosis are chronic pelvic pain and subfertility.

Estrogen (E2) deprivation is the clinically proven concept and the underlying primary mechanism of action for pharmacological treatment of endometriosis. Besides systemic estrogen levels, there is increasing evidence that locally derived estrogen contributes to the growth of endometriotic lesions. High intra-tissue estrogen concentrations in endometriotic lesions have recently been described, suggesting high local estrogen synthesis in endometriosis (Huhtinen et al. J Clin Endocrinol Metab. 2012, 97(11):4228-4235). Accordingly, inhibition of local E2 production in the endometriotic lesion is regarded as a highly attractive mechanism of action for the treatment of endometriosis.

AKR1C3 is strongly expressed in endometriotic lesions and only marginally detectable in the ovary (Smuc et al. Mol Cell Endocrinol. 2009, 301(1-2):59-64). In a concerted action with CYP19A1 (aromatase), AKR1C3 is expected to be a key enzyme in local E2 production in endometriotic lesions, generating a pro-estrogenic environment, thereby stimulating proliferation in estrogen-sensitive endometriotic cells. Inhibition of AKR1C3 should therefore result in decreased local intra-tissue E2 levels and thereby decreased proliferation of endometriotic lesions. Effects on ovarian estrogen production are not expected, since AKR1C3 is only marginally expressed in the ovary and 17βHSD1 is the dominant ovarian hydroxysteroid dehydrogenase.

AKR1C3 is also a PGF2a synthase and beside the upregulation of AKR1C3 in endometriotic lesions, it has been shown that levels of PGF2a were significantly higher in both the eutopic and ectopic endometria derived from women with peritoneal endometriosis than in similar tissues derived from women with ovarian endometrioma (Sinreih et al. Chemico-Biological Interactions 2015, 234:320-331). PGF2a in endometriotic tissues is expected contribute to inflammation, pain and proliferation in endometriosis patients and AKR1C3, expressed in endometriotic lesions, is expected to contribute to high local PGF2a level in endometriotic tissues.

AKR1C3 inhibition has the potential to relieve proliferation, pain and inflammation in endometriosis patients by locally reducing E2, testosterone and PGF2a levels in the endometriotic tissues.

Polycystic Ovary Syndrome (PCOS):

PCOS is a common endocrine disorder, affecting up to 10% of women of reproductive age. It is associated clinically with anovulatory infertility, dysfunctional bleeding, androgen excess, hyperinsulinemia and insulin resistance, obesity and metabolic syndrome (Dunaif et al. Endocrine Rev. 1997, 18:774-800). Four cardinal features of PCOS have been recognized by the Androgen Excess Society: ovulatory and menstrual dysfunction, biochemical hyperandrogenaemia, clinical hyperandrogonism (e.g. acne, hirsutism) and polycystic ovaries (Azziz et al. Clin Endocrinol Metab 2006, 91:4237-45). The vast majority of women with PCOS will present with clinical signs of hyperandrogonism, e.g. acne, hirsutism, or anovulation manifest by primary subfertility or oligomenorrhea (Legro et al. N Engl J Med 2014, 371:119-129). Women with PCOS are predisposed to glucose intolerance and metabolic syndrome (Taponen et al. J of Clin Endocrinology and Metabolism 2004, 89:2114-2118), with associated risk factors for cardiovascular disease and a likely increased risk in future cardiovascular events (Mani et al. Clin Endocrinol 2013, 78:926-934).

Hyperandrogonism, hirsutism and/or hyperandrogenaemia is the key component of the syndrome and is mandatory for the diagnosis of PCOS (Azziz et al. Clin Endocrinol Metab 2006, 91:4237-45). While serum testosterone is a key factor for biochemical assessment of hyperandrogenaemia, recently androstenedione was suggested as a more reliable marker of PCOS-related androgen excess, since androstenedione is circulating at high concentrations in PCOS women (Reilly et al. J Clin Endocrinol Metab 2014, jc20133399).

PCOS has traditionally been regarded as a disorder of the ovary (Franks et al. J Steroid Biochem Molecular Biology 1999, 69:269-272). However, increased focus on extra-ovarian and extra-adrenal androgen formation in PCOS has highlighted the role of peripheral tissues such as adipose androgen formation (Quinkler et al. J of Endocrinology 2004, 183:331-342).

AKR1C3 is an androgen-activating enzyme, known to predominantly convert androstenedione to testosterone. Upregulation of AKR1C3 in adipose tissue of PCOS patients has been described, indicating that ARK1C3 expression in adipose is significantly contributing to androgen formation for androstenedione in PCOS patients. It has in addition been shown that AKR1C3 expression in adipocytes is significantly increased by insulin, indicating that insulin, which is high in PCOS is able to drive adipose androgen formation by increasing AKR1C3 activity in female subcutaneous adipose tissue (O'Reilly et al. Lancet 2015, 385 Suppl 1:S16). AKR1C3 is also a PGF2a synthase and plays a suppressive role in the formation of endogenous ligands for the peroxisome proliferator-activated receptor γ (PPAR-gamma), which is a target for insulin-sensitizing drugs (Spiegelman et al. Diabetes 1998, 47:507-514).

Selective AKR1C3 inhibition might offer a novel therapeutic target to reduce androgen burden and improve the metabolic phenotype in PCOS. (O'Reilly M1, et al. Lancet. 2015 385 Suppl 1:S16.; Du et al. J Clin Endocrinol Metab. 2009, 94(7):2594-2601.)

Cancer:

AKR1C3 is overexpressed in numerous cancers, which includes those cancers of the prostate, breast, uterine, blood, lung, brain and kidney, such as endometrial carcinoma (T. L. Rizner et al., *Mol Cell Endocrinol* 2006 248(1-2), 126-135), lung carcinoma (Q. Lan et al., *Carcinogenesis* 2004, 25(11), 2177-2181), non-Hodgkin lymphoma (Q. Lan et al., *Hum Genet* 2007, 121(2), 161-168), bladder carcinoma (J. D. Figueroa, *Carcinogenesis* 2008, 29(10), 1955-1962), chronic myeloid leukaemia (J. Birthwistle, *Mutat Res* 2009, 662(1-2), 67-74), renal cell carcinoma (J. T. Azzarello, *Int J Clin Exp Pathol* 2009, 3(2), 147-155), breast cancer (M. C. Byrns, *J Steroid Biochem Mol Biol* 2010, 118(3), 177-187), whereas its upregulation frequently correlates with tumor invasiveness and aggressiveness (Azzarello et al. Int. J. Clin. Exp. Path. 2009, 3:147-155, Birtwistle et al. Mutat. Res. 2009, 662:67-74; Miller et al. Int. J. Clin. Exp. Path. 2012, 5:278-289). AKR1C3 is able to directly reduce estrone and progesterone to 17β-estradiol and 20α-hydroxyprogesterone, respectively, thereby potentiating this pro-proliferative signal (Smuc and Rizner, Chem Biol Interact. 2009, 178: 228-33). Additionally, the prostaglandin F synthase activities of AKR1C3 catalyses the conversion of PGH2 to PGF2α and PGD2 to 11β-PGF2, both known to stimulate inflammation and proliferation. In the absence of AKR1C3 activity, PGD2 (instead of being converted to PGF2), spontaneously dehydrates and rearranges to form anti-proliferative and anti-inflammatory PGJ2 isomers, including 15d-PGJ2. In summary, AKR1C3 increases the proliferative PGF2 isomers and decreases antiproliferative PGJ2 products, and therefore AKR1C3 has the potential to impact both hormone-dependent and hormone-independent cancers. In breast cancer it is postulated that actions of AKR1C3 can produce prostaglandin F2 alpha (PTGFR) ligands whose activation results in carcinoma cell survival (Yoda T et al., (2015) Mol Cell Endocrinol. 15; 413:236-247).

Prostate Cancer:

Elevated expression of AKR1C3 has been associated with prostate cancer progression and aggressiveness (Stanbrough M et al. Cancer Res 2006, 66:2815-25; Wako K et al. J Clin Pathol. 2008, 61(4):448-54). In hormone-dependent prostate cancer, AKR1C3 converts androstenedione to testosterone, which, in turn, excessively activates androgen receptors and promotes tumor growth (Penning et al. Mol Cell Endocrinol. 2006, 248(1-2):182-91).

In Castration-Resistant Prostate Cancer (CRPC)

AKR1C3 is involved in intratumoral androgen biosynthesis—it facilitates the conversion of weak androgens androstenedione (A' dione) and 5 α-androstanedione (5α-dione) to the more active androgens testosterone and DHT, respectively (Liu et al. Cancer Res. 2015, 75(7):1413-22; Fung et al. *Endocr Relat Cancer* 2006, 13(1), 169-180). Importantly, AKR1C3 expression has been shown to be increased in patients with CRPC compared with primary prostate cancer (Stanbrough et al. Cancer Res 2006, 66: 2815-2825; Hamid et al. Mol Med 2012, 18:1449-1455; Pfeiffer et al. Mol Med 2011, 17:657-664). A genetic polymorphism in the AKR1C3 gene coding for AKR1C3 was also shown to be an independent predictor of prostate cancer (Yu et al. PLoS One 2013, 8(1):e54627). Moreover, AKR1C3-dependent de novo androgen synthesis was suggested to be a potential mechanism of resistance to CYP17A1 inhibitors, such as abiraterone (Mostaghel et al. Clin Cancer Res 2011, 17:5913-5925; Cai et al. Cancer Res 2011, 71:6503-6513). Therefore, AKR1C3 may be a promising therapeutic target in patients with CRPC (Adeniji et al. J Steroid Biochem Mol Biol 2013, 137:136-149). An AKR1C3 inhibitor was tested in patients with metastatic castration-resistant prostate cancer in a multi-centre phase I/II study. However, the novel androgen biosynthesis inhibitor showed no relevant evidence of clinical activity (Loriot et al. Invest New Drugs 2014, 32:995-1004). Recent data are indicating that AKR1C3 activation in CRPC is a critical resistance mechanism associated with anti-androgen (enzalutamide) resistance. It could be shown that androgen precursors such as cholesterol, DHEA and progesterone, as well as androgens are highly upregulated in enzalutamide-resistant prostate cancer cells compared to the parental cells. The data suggest that inhibition of AKR1C3 pathways could act as an enzalutamide-sensitizing treatment and restore efficacy in patients with enzalutamide-resistant CRPC (Liu et al. Cancer Res. 2015, 75(7):1413-22). It is postulated that co-treatment with an AKR1C3 inhibitor will overcome enzalutamide resistance and improve survival of advanced prostate cancer patients (Thoma et al. Nature Reviews Urology 2015, 12:124).

Anthracycline Resistant Cancer:

Anthracyclines (or anthracycline antibiotics) are a class of drugs which are used in cancer chemotherapy and derived from *Streptomyces* bacterium *Streptomyces peucetius* var. *caesius* (Fujiwara et al. Critical Reviews in Biotechnology 1985, 3(2):133). These compounds are used to treat many cancers, including leukaemia's, lymphomas, breast, stomach, uterine, ovarian, bladder cancer, and lung cancers. The anthracyclines are among the most effective anticancer treatments ever developed. However, the clinical success of anthracyclines for cancer treatment is overshadowed by drug resistance. It has become widely accepted that the elevated enzymatic reduction of anthracyclines to their less potent secondary C13-hydroxy metabolites constitutes one of the mechanisms that cause anthracycline resistance in tumors (Gavelova et al., 2008 Chem. Biol. Interact 176, 9-18; Heibein et al. 2012 BMC Cancer 12, 381). Enzymatic metabolism, especially of doxorubicin is responsible for the cardiomyopathy observed upon doxorubicin chemotherapy. AKR1C3 was shown to be implicated in the metabolism of clinically administered anthracyclines such as doxorubicin and daunorubicin (Novotna et al. Toxicol. Letter 2008, 181:1-6).

In 2012, a correlation of an AKR1C3 genetic variant with doxorubicin pharmacodynamics has been shown in Asian breast cancer patients: one genetic variant was associated with longer progression-free survival and overall survival after doxorubicin-based therapy suggesting potential interaction with the doxorubicin metabolism (Voon et al. British J of Clin Pharmacology 2012, 75:1497-1505).

Recently it could be demonstrated that AKR1C3 contributes to the resistance of cancer cells to anthracycline treatment and therefore concomitant administration of a specific AKR1C3 inhibitor with anthracyclines could be an efficient strategy for the successful prevention and treatment of anthracycline resistant tumors (Hofman et al. Toxicology and Applied Pharmacology 2014, 278:238-248).

Atopic Dermatitis:

Challenge of atopic subjects with antigen caused the release of PGD2 and histamine showing that PGD2 contributes little to the immediate hypersensitivity reactions of human skin and that PGD2 is a lipid mediator that promotes skin inflammation in atopic dermatitis (AD) (Barr et al., Br J Pharmacol. 1988, 94:773-80; Satoh et al. J Immunol. 2006, 177:2621-9.; Shimura et al. Am J Pathol. 2010; 176:227-37). PGD2 is a relatively unstable pro-inflammatory mediator which spontaneously converts to the potent anti-inflammatory mediator 15d-PGJ2. That conversion is diverted by the metabolism of PGD2 to the pro-inflammatory 9α,11β-PGF2 by AKR1C3. (Mantel et al. Exp Dermatol. 2016, 25(1):38-43).

It was demonstrated that AKR1C3 is upregulated in human AD samples and a role for AKR1C3 in mediating inflammation in skin pathology, especially atopic dermatitis and in keloids has been postulated (Mantel et al. J Invest Dermatol. 2012, 132(4): 1103-1110) Mantel et al. Exp Dermatol. 2016, 25(1):38-43). AKR1C3 inhibition might be a novel option for treatment of AD and keloids.

Inflammation:

AKR1C3 is involved in prostaglandin biosynthesis, catalyzing the conversion of PGH2 to PGF2α and PGD2 to 11β-PGF2. It has been postulated that expression and upregulation of AKR1C3 supports inflammation by directly causing an increase in 9α,11β-PGF2 synthesis rates and diverting the spontaneous generation of the potent anti-inflammatory mediator 15d-PGJ2 (Mantel et al. J Invest Dermatol 2012, 132(4):1103-1110). This function of AKR1C3 has also been implicated in HL-60 cells (Desmond et al. Cancer Res 2003, 63:505-512) and in MCF-7 cells (Byrns et al. J Steroid Biochem Mol Biol 2010, 118:177-187). Inhibition of AKR1C3 is postulated to increase 15d-PGJ2, an anti-inflammatory lipid that mostly mediates its actions directly via activation of peroxisome proliferator-activated receptor γ (PPAR-γ) and/or inhibition of NF-κB signaling in immune cells (Maggi et al. Diabetes 2000, 49:346-355; Scher et al. Clinical Immunology 2005, 114: 100-109). Previous data have shown that PPAR-γ activation attenuates allergen-induced inflammation in skin and lungs of mice (Ward et al. Carcinogenesis. 2006, 27(5):1074-80; Dahten et al. J Invest Dermatol. 2008, 128(9):2211-8.). This suggests a role for AKR1C3 inhibition in suppressing of inflammation.

Further Diseases

Furthermore AKR1C3 inhibitors have potential for the treatment of prostate hyperplasia (Roberts et al., *Prostate* 2006, 66(4), 392-404), hair loss (L. Colombe et al., *Exp Dermatol* 2007, 16(9), 762-769), adiposity (P. A. Svensson et al., *Cell Mol Biol Lett* 2008, 13(4), 599-613), premature sexual maturity (C. He, *Hum Genet* 2010, 128(5), 515-527) and chronic obstructive pulmonary disease (S. Pierrou, *Am J Respir Crit Care* 2007, 175(6), 577-586).

Inhibitors of AKR1C3 are described in the prior art: Flanagan et al. Bioorganic & Medicinal Chemistry 2014, 22:967-977, Jamieson et al. Journal of Medicinal Chemistry 2012, 55:7746-7758, WO 2013/059245, WO 2013/142390, WO 2014/039820, WO 2013/045407, WO 2014/128108 and WO 2014/009274.

Heinrich et al. European Journal of Medicinal Chemistry 2013, 62:738-744 relates to 1-(4-(piperidin-1-ylsulfonyl) phenyl)pyrrolidin-2-ones as inhibitors of AKR1C3.

WO 2007/111921 (Amgen) relates to 1-phenylsulfonyl-diaza heterocyclic amide compounds and their uses in methods for treating a condition or disorder responsive to the modulation of hydroxysteroid dehydrogenases (HSD's), mainly for the treatment of diabetis or obesity. Among other diseases endometriosis is also specified. 11betaHSD1, 11betaHSD2 and 17betaHSD3 are explicitly disclosed. It is shown that the disclosed examples inhibit 11 betaHSD1 with a IC$_{50}$ ranging from <1 nM-1000 nM. However, inhibition or modulation of the enzymatic activity of AKR1C3 or other HSD's are not disclosed. WO 2007/111921 relates inter alia to piperazine compounds, e.g. compound number 4 of table 1. However, piperazines with an ethylene bridge between position 2 and 6 are not disclosed in WO 2007/111921.

WO 2007/103456 (Trimeris) relates to piperazine derivatives and to methods of using the same in the treatment of HIV infection and AIDS.

WO 2008/024284 (Merck) relates to sulfonylated piperazines as cannabinoid-1 receptor modulators.

However, the state of the art does not describe the [8-(phenylsulfonyl)-3,8-diazabicyclo[3.2.1]oct-3-yl](1H-1,2,3-triazol-4-yl)methanone compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively inhibit AKR1C3 for which data are given in biological experimental section and may therefore be used for the treatment or prophylaxis of AKR1C3 related disorders such as gynecological disorders particularly endometriosis-related and polycystic ovary syndrome-related gynecological disorders, conditions and diseases, metabolic disorders, hyperproliferative disorders, conditions and diseases, and inflammation disorders.

In accordance with a first aspect, the present invention covers compounds of general formula (I):

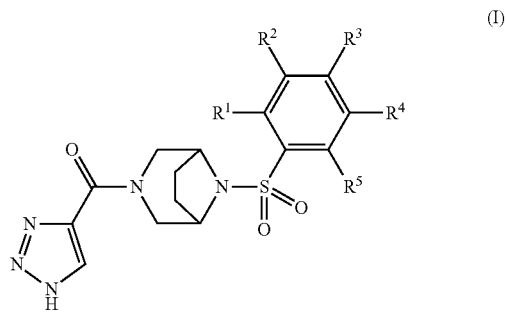

in which:

R$^1$ represents hydrogen, halogen, C$_1$-C$_3$-alkyl, C$_1$-C$_3$-haloalkyl, C$_1$-C$_3$-alkoxy, C$_1$-C$_3$-haloalkoxy, nitro or cyano;

R² represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;

R³ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or hydroxy;

R⁴ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;

R⁵ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;

wherein R¹ and R² or R² and R³ are optionally linked to one another in such a way that they jointly form a methylenedioxy, ethylenedioxy, ethyleneoxy, trimethyleneoxy or a group selected from:

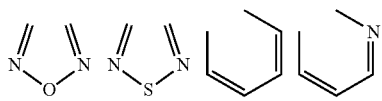

and stereoisomers, tautomers, N-oxides, hydrates, solvates, and salts thereof, and mixtures of same.

Definitions

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_3$-alkyl" means a linear or branched, saturated, monovalent hydrocarbon group having 1, 2 or 3 carbon atoms, e.g. a methyl, ethyl, propyl, isopropyl, e.g. a methyl, ethyl, n-propyl or isopropyl group.

The term "$C_1$-$C_3$-haloalkyl" means a linear or branched, saturated, monovalent hydrocarbon group in which the term "$C_1$-$C_3$-alkyl" is as defined supra, and in which one or more of the hydrogen atoms are replaced, identically or differently, with a halogen atom. Particularly, said halogen atom is a fluorine atom. Said $C_1$-$C_3$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_3$-alkoxy" means a linear or branched, saturated, monovalent group of formula ($C_1$-$C_3$-alkyl)-O—, in which the term "$C_1$-$C_3$-alkyl" is as defined supra, e.g. a methoxy, ethoxy, n-propoxy or isopropoxy.

The term "$C_1$-$C_3$-haloalkoxy" means a linear or branched, saturated, monovalent $C_1$-$C_3$-alkoxy group, as defined supra, in which one or more of the hydrogen atoms is replaced, identically or differently, with a halogen atom. Particularly, said halogen atom is a fluorine atom. Said $C_1$-$C_3$-haloalkoxy group is, for example, fluoromethoxy, difluoromethoxy or trifluoromethoxy.

The term "$C_1$-$C_3$", as used in the present text, e.g. in the context of the definition of "$C_1$-$C_3$-alkyl", "$C_1$-$C_3$-haloalkyl", "$C_1$-$C_3$-alkoxy" or "$C_1$-$C_3$-haloalkoxy" means an alkyl group having a finite number of carbon atoms of 1 to 3, i.e. 1, 2 or 3 carbon atoms.

When a range of values is given, said range encompasses each value and sub-range within said range.

For example:

"$C_1$-$C_3$" encompasses $C_1$, $C_2$, $C_3$, $C_1$-$C_3$, $C_1$-$C_2$ and $C_2$-$C_3$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl) sulfonyl]oxy, [(4-nitrophenyl)sulfonyl]oxy, [(2-nitrophenyl)sulfonyl]oxy, [(4-isopropylphenyl) sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity (C. L. Perrin, et al., J. Am. Chem. Soc., 2007, 129, 4490), basicity (C. L. Perrin et al., J. Am. Chem. Soc., 2005, 127, 9641), lipophilicity (B. Testa et al., Int. J. Pharm., 1984, 19(3), 271)) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect.

Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

Further, it is possible for the compounds of the present invention to exist as tautomers. For example, any compound of the present invention which contains a 1,2,3-triazole moiety can exist as a 1H tautomer or a 3H tautomer, or even as a mixture in any amount of the two tautomers, namely:

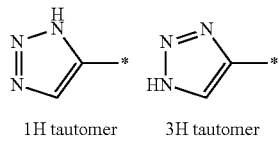

1H tautomer    3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge et al. J. Pharm. Sci. 1977, 66:1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethane-sulfonic, dodecylsulfuric, ethanesulfonic, benzenesulfonic, para-toluenesulfonic, methane-sulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:
$R^1$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
$R^2$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
$R^3$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or hydroxy;
$R^4$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
$R^5$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
and stereoisomers, tautomers, N-oxides, hydrates, solvates, and salts thereof, and mixtures of same.

In accordance with a third embodiment of the first aspect, the present invention covers compounds of general formula (I), supra, in which:
$R^1$ represents hydrogen, fluoro, chloro, bromo, methyl, trifluoromethyl, methoxy, trifluoromethoxy or cyano;
$R^2$ represents hydrogen, fluoro, chloro, bromo, methyl, trifluoromethyl, methoxy, trifluoromethoxy, cyano or $SF_5$;
$R^3$ represents hydrogen;
$R^4$ represents hydrogen, fluoro, chloro, bromo, methyl, trifluoromethyl, methoxy, trifluoromethoxy, cyano or $SF_5$;
$R^5$ represents hydrogen, fluoro, chloro, bromo, methyl, trifluoromethyl, methoxy, trifluoromethoxy or cyano;
and stereoisomers, tautomers, N-oxides, hydrates, solvates, and salts thereof, and mixtures of same.

In accordance with a fourth embodiment of the first aspect, the present invention covers compounds of general formula (I), supra, in which:
$R^1$ represents hydrogen, fluoro, chloro, bromo, methyl or trifluoromethyl;
$R^2$ represents hydrogen, fluoro, chloro, bromo, methyl, trifluoromethyl or $SF_5$;
$R^3$ represents hydrogen;
$R^4$ represents hydrogen, fluoro, chloro, bromo, methyl, trifluoromethyl or $SF_5$;
$R^5$ represents hydrogen, fluoro, chloro, bromo, methyl or trifluoromethyl;
and stereoisomers, tautomers, N-oxides, hydrates, solvates, and salts thereof, and mixtures of same.

Further embodiments of the first aspect of the present invention:

In a further embodiment of the first aspect, the present invention covers compounds of formula (I), supra, in which:
$R^1$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
and stereoisomers, tautomers, N-oxides, hydrates, solvates, and salts thereof, and mixtures of same.

In a further embodiment of the first aspect, the present invention covers compounds of formula (I), supra, in which:
$R^1$ represents hydrogen, fluoro, chloro, bromo, methyl, trifluoromethyl, methoxy, trifluoromethoxy or cyano;
and stereoisomers, tautomers, N-oxides, hydrates, solvates, and salts thereof, and mixtures of same.

In a further embodiment of the first aspect, the present invention covers compounds of formula (I), supra, in which:
$R^1$ represents hydrogen, fluoro, chloro, bromo, methyl or trifluoromethyl;
and stereoisomers, tautomers, N-oxides, hydrates, solvates, and salts thereof, and mixtures of same.

In a further embodiment of the first aspect, the present invention covers compounds of formula (I), supra, in which:
$R^2$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^2$ represents hydrogen, fluoro, chloro, bromo, methyl, trifluoromethyl, methoxy, trifluoromethoxy, cyano or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^2$ represents hydrogen, fluoro, chloro, bromo, methyl, trifluoromethyl or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^3$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or hydroxy;
and stereoisomers, tautomers, N-oxides, hydrates, solvates, and salts thereof, and mixtures of same.

In a further embodiment of the first aspect, the present invention covers compounds of formula (I), supra, in which:
$R^3$ represents hydrogen;
and stereoisomers, tautomers, N-oxides, hydrates, solvates, and salts thereof, and mixtures of same.

In a further embodiment of the first aspect, the present invention covers compounds of formula (I), supra, in which:
$R^4$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^4$ represents hydrogen, fluoro, chloro, bromo, methyl, trifluoromethyl, methoxy, trifluoromethoxy, cyano or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^4$ represents hydrogen, fluoro, chloro, bromo, methyl, trifluoromethyl or $SF_5$;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents hydrogen, fluoro, chloro, bromo, methyl, trifluoromethyl, methoxy, trifluoromethoxy or cyano;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents hydrogen, fluoro, chloro, bromo, methyl or trifluoromethyl;
and stereoisomers, tautomers, N-oxides, hydrates, solvates, and salts thereof, and mixtures of same.

In a further embodiment of the first aspect, the present invention covers compounds of formula (I), supra, in which:
$R^1$ and $R^2$ or $R^2$ and $R^3$ are linked to one another in such a way that they jointly form a methylenedioxy, ethylenedioxy, ethyleneoxy, trimethyleneoxy or
a group selected from:

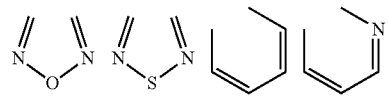

and stereoisomers, tautomers, N-oxides, hydrates, solvates, and salts thereof, and mixtures of same.

In a further embodiment of the first aspect, the present invention covers compounds of formula (I), supra, in which:
$R^1$ and $R^2$ or $R^2$ and $R^3$ are linked to one another in such a way that they jointly form a methylenedioxy, ethylenedioxy, ethyleneoxy or trimethyleneoxy group;
and stereoisomers, tautomers, N-oxides, hydrates, solvates, and salts thereof, and mixtures of same.

In a further embodiment of the first aspect, the present invention covers compounds of formula (I), supra, in which:
$R^1$ and $R^2$ or $R^2$ and $R^3$ are linked to one another in such a way that they jointly form a group selected from:

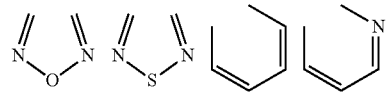

and stereoisomers, tautomers, N-oxides, hydrates, solvates, and salts thereof, and mixtures of same.

In a further embodiment of the first aspect, the present invention covers compounds of formula (I), supra, in which:
$R^1$ and $R^2$ or $R^2$ and $R^3$ are linked to one another in such a way that they jointly form a group selected from:

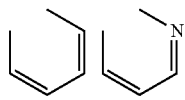

and stereoisomers, tautomers, N-oxides, hydrates, solvates, and salts thereof, and mixtures of same.

In a further embodiment of the first aspect, the present invention covers a compound which is selected from the group consisting of:

1 [8-(phenylsulfonyl)-3,8-diazabicyclo[3.2.1]oct-3-yl](1H-1,2,3-triazol-4-yl)methanone
2 1H-1,2,3-triazol-4-yl[8-{[2-(trifluoromethyl)phenyl]sulfonyl}-3,8-diazabicyclo[3.2.1]oct-3-yl]methanone
3 {8-[(3,5-difluorophenyl)sulfonyl]-3,8-diazabicyclo[3.2.1]oct-3-yl}(1H-1,2,3-triazol-5-yl)methanone
4 {8-[(3-fluorophenyl)sulfonyl]-3,8-diazabicyclo[3.2.1]oct-3-yl}(1H-1,2,3-triazol-5-yl)methanone
5 {8-[(3-chlorophenyl)sulfonyl]-3,8-diazabicyclo[3.2.1]oct-3-yl}(1H-1,2,3-triazol-5-yl)methanone
6 {8-[(2-methylphenyl)sulfonyl]-3,8-diazabicyclo[3.2.1]oct-3-yl}(1H-1,2,3-triazol-4-yl)methanone
7 {8-[(2-chlorophenyl)sulfonyl]-3,8-diazabicyclo[3.2.1]oct-3-yl}(1H-1,2,3-triazol-4-yl)methanone
8 [8-{[3-(pentafluoro-lambda<sup>6</sup>-sulfanyl)phenyl]sulfonyl}-3,8-diazabicyclo[3.2.1]oct-3-yl](1H-1,2,3-triazol-4-yl)methanone
9 {8-[(3,5-dichlorophenyl)sulfonyl]-3,8-diazabicyclo[3.2.1]oct-3-yl}(1H-1,2,3-triazol-4-yl)methanone
10 [8-{[3,5-bis(trifluoromethyl)phenyl]sulfonyl}-3,8-diazabicyclo[3.2.1]oct-3-yl](1H-1,2,3-triazol-5-yl)methanone
11 {8-[(5-chlorothiophen-2-yl)sulfonyl]-3,8-diazabicyclo[3.2.1]oct-3-yl}(1H-1,2,3-triazol-4-yl)methanone
12 {8-[(2,5-difluorophenyl)sulfonyl]-3,8-diazabicyclo[3.2.1]oct-3-yl}(1H-1,2,3-triazol-4-yl)methanone
13 {8-[(3-methylphenyl)sulfonyl]-3,8-diazabicyclo[3.2.1]oct-3-yl}(1H-1,2,3-triazol-5-yl)methanone
14 {8-[(4-methylphenyl)sulfonyl]-3,8-diazabicyclo[3.2.1]oct-3-yl}(1H-1,2,3-triazol-5-yl)methanone
15 {8-[(2-fluorophenyl)sulfonyl]-3,8-diazabicyclo[3.2.1]oct-3-yl}(1H-1,2,3-triazol-5-yl)methanone
16 {8-[(4-fluorophenyl)sulfonyl]-3,8-diazabicyclo[3.2.1]oct-3-yl}(1H-1,2,3-triazol-5-yl)methanone
17 3-{[3-(1H-1,2,3-triazol-5-ylcarbonyl)-3,8-diazabicyclo[3.2.1]oct-8-yl]sulfonyl}benzonitrile
18 {8-[(3,5-dimethylphenyl)sulfonyl]-3,8-diazabicyclo[3.2.1]oct-3-yl}(1H-1,2,3-triazol-5-yl)methanone
19 {8-[(2,5-dimethylphenyl)sulfonyl]-3,8-diazabicyclo[3.2.1]oct-3-yl}(1H-1,2,3-triazol-5-yl)methanone
20 {8-[(3-methoxyphenyl)sulfonyl]-3,8-diazabicyclo[3.2.1]oct-3-yl}(1H-1,2,3-triazol-5-yl)methanone
21 {8-[(4-methoxyphenyl)sulfonyl]-3,8-diazabicyclo[3.2.1]oct-3-yl}(1H-1,2,3-triazol-5-yl)methanone
22 {8-[(4-chlorophenyl)sulfonyl]-3,8-diazabicyclo[3.2.1]oct-3-yl}(1H-1,2,3-triazol-5-yl)methanone
23 {8-[(3,4-difluorophenyl)sulfonyl]-3,8-diazabicyclo[3.2.1]oct-3-yl}(1H-1,2,3-triazol-5-yl)methanone
24 {8-[(2,6-difluorophenyl)sulfonyl]-3,8-diazabicyclo[3.2.1]oct-3-yl}(1H-1,2,3-triazol-5-yl)methanone
25 {8-[(2,4-difluorophenyl)sulfonyl]-3,8-diazabicyclo[3.2.1]oct-3-yl}(1H-1,2,3-triazol-5-yl)methanone
26 {8-[(3-chloro-2-methylphenyl)sulfonyl]-3,8-diazabicyclo[3.2.1]oct-3-yl}(1H-1,2,3-triazol-5-yl)methanone
27 {8-[(3-chloro-2-fluorophenyl)sulfonyl]-3,8-diazabicyclo[3.2.1]oct-3-yl}(1H-1,2,3-triazol-5-yl)methanone
28 {8-[(3-chloro-4-fluorophenyl)sulfonyl]-3,8-diazabicyclo[3.2.1]oct-3-yl}(1H-1,2,3-triazol-5-yl)methanone
29 1H-1,2,3-triazol-5-yl[8-{[3-(trifluoromethyl)phenyl]sulfonyl}-3,8-diazabicyclo[3.2.1]oct-3-yl]methanone
30 {8-[(2,5-dichlorophenyl)sulfonyl]-3,8-diazabicyclo[3.2.1]oct-3-yl}(1H-1,2,3-triazol-5-yl)methanone
31 {8-[(3-bromophenyl)sulfonyl]-3,8-diazabicyclo[3.2.1]oct-3-yl}(1H-1,2,3-triazol-5-yl)methanone
32 {8-[(2-bromophenyl)sulfonyl]-3,8-diazabicyclo[3.2.1]oct-3-yl}(1H-1,2,3-triazol-5-yl)methanone
33 1H-1,2,3-triazol-5-yl[8-{[3-(trifluoromethoxy)phenyl]sulfonyl}-3,8-diazabicyclo[3.2.1]oct-3-yl]methanone
34 [8-{[5-chloro-2-(trifluoromethyl)phenyl]sulfonyl}-3,8-diazabicyclo[3.2.1]oct-3-yl](1H-1,2,3-triazol-5-yl)methanone
35 2-{[3-(1H-1,2,3-triazol-5-ylcarbonyl)-3,8-diazabicyclo[3.2.1]oct-8-yl]sulfonyl}benzonitrile
36 1H-1,2,3-triazol-5-yl[8-{[4-(trifluoromethyl)phenyl]sulfonyl}-3,8-diazabicyclo[3.2.1]oct-3-yl]methanone
37 {8-[(4-hydroxyphenyl)sulfonyl]-3,8-diazabicyclo[3.2.1]oct-3-yl}(1H-1,2,3-triazol-5-yl)methanone
38 {8-[(4-bromophenyl)sulfonyl]-3,8-diazabicyclo[3.2.1]oct-3-yl}(1H-1,2,3-triazol-5-yl)methanone
39 [8-(naphthalen-1-ylsulfonyl)-3,8-diazabicyclo[3.2.1]oct-3-yl](1H-1,2,3-triazol-5-yl)methanone

| | |
|---|---|
| 40 | [8-(quinolin-8-ylsulfonyl)-3,8-diazabicyclo[3.2.1]oct-3-yl](1H-1,2,3-triazol-5-yl)methanone |
| 41 | 1H-1,2,3-triazol-5-yl[8-{[4-(trifluoromethoxy)phenyl]sulfonyl}-3,8-diazabicyclo[3.2.1]oct-3-yl]methanone |
| 42 | 1H-1,2,3-triazol-5-yl[8-{[2-(trifluoromethoxy)phenyl]sulfonyl}-3,8-diazabicyclo[3.2.1]oct-3-yl]methanone |
| 43 | {8-[(4-nitrophenyl)sulfonyl]-3,8-diazabicyclo[3.2.1]oct-3-yl}(1H-1,2,3-triazol-5-yl)methanone |
| 44 | {8-[(3-nitrophenyl)sulfonyl]-3,8-diazabicyclo[3.2.1]oct-3-yl}(1H-1,2,3-triazol-5-yl)methanone |
| 45 | 1H-1,2,3-triazol-5-yl{8-[(2,4,6-trimethylphenyl)sulfonyl]-3,8-diazabicyclo[3.2.1]oct-3-yl}methanone |
| 46 | {8-[(2-nitrophenyl)sulfonyl]-3,8-diazabicyclo[3.2.1]oct-3-yl}(1H-1,2,3-triazol-5-yl)methanone |
| 47 | {8-[(2,5-dimethoxyphenyl)sulfonyl]-3,8-diazabicyclo[3.2.1]oct-3-yl}(1H-1,2,3-triazol-5-yl)methanone |
| 48 | {8-[(3,4-dichlorophenyl)sulfonyl]-3,8-diazabicyclo[3.2.1]oct-3-yl}(1H-1,2,3-triazol-5-yl)methanone |
| 49 | {8-[(4-ethylphenyl)sulfonyl]-3,8-diazabicyclo[3.2.1]oct-3-yl}(1H-1,2,3-triazol-5-yl)methanone |
| 50 | {8-[(2-chloro-4-fluorophenyl)sulfonyl]-3,8-diazabicyclo[3.2.1]oct-3-yl}(1H-1,2,3-triazol-5-yl)methanone |
| 51 | {8-[(2-chloro-6-methylphenyl)sulfonyl]-3,8-diazabicyclo[3.2.1]oct-3-yl}(1H-1,2,3-triazol-5-yl)methanone |
| 52 | {8-[(3,4-dimethoxyphenyl)sulfonyl]-3,8-diazabicyclo[3.2.1]oct-3-yl}(1H-1,2,3-triazol-5-yl)methanone |
| 53 | {(1S)-8-[(2,3-dichlorophenyl)sulfonyl]-3,8-diazabicyclo[3.2.1]oct-3-yl}(1H-1,2,3-triazol-5-yl)methanone |
| 54 | [8-(2,1,3-benzothiadiazol-4-ylsulfonyl)-3,8-diazabicyclo[3.2.1]oct-3-yl](1H-1,2,3-triazol-5-yl)methanone |
| 55 | [8-(2,1,3-benzoxadiazol-4-ylsulfonyl)-3,8-diazabicyclo[3.2.1]oct-3-yl](1H-1,2,3-triazol-5-yl)methanone |
| 56 | 1H-1,2,3-triazol-5-yl{8-[(2,4,6-trichlorophenyl)sulfonyl]-3,8-diazabicyclo[3.2.1]oct-3-yl}methanone |
| 57 | {8-[(5-chloro-2-methoxyphenyl)sulfonyl]-3,8-diazabicyclo[3.2.1]oct-3-yl}(1H-1,2,3-triazol-5-yl)methanone |
| 58 | [8-(2,1,3-benzothiadiazol-5-ylsulfonyl)-3,8-diazabicyclo[3.2.1]oct-3-yl](1H-1,2,3-triazol-5-yl)methanone |
| 59 | 1H-1,2,3-triazol-5-yl{8-[(2,3,4-trifluorophenyl)sulfonyl]-3,8-diazabicyclo[3.2.1]oct-3-yl}methanone |
| 60 | 2-fluoro-5-{[3-(1H-1,2,3-triazol-5-ylcarbonyl)-3,8-diazabicyclo[3.2.1]oct-8-yl]sulfonyl}benzonitrile |
| 61 | {8-[(5-chloro-2-fluorophenyl)sulfonyl]-3,8-diazabicyclo[3.2.1]oct-3-yl}(1H-1,2,3-triazol-5-yl)methanone |
| 62 | 1H-1,2,3-triazol-5-yl{8-[(2,4,5-trifluorophenyl)sulfonyl]-3,8-diazabicyclo[3.2.1]oct-3-yl}methanone |
| 63 | {8-[(5-chloro-2-methylphenyl)sulfonyl]-3,8-diazabicyclo[3.2.1]oct-3-yl}(1H-1,2,3-triazol-5-yl)methanone |
| 64 | {8-[(2-methoxyphenyl)sulfonyl]-3,8-diazabicyclo[3.2.1]oct-3-yl}(1H-1,2,3-triazol-5-yl)methanone |
| 65 | {8-[(5-bromo-2-methylphenyl)sulfonyl]-3,8-diazabicyclo[3.2.1]oct-3-yl}(1H-1,2,3-triazol-5-yl)methanone |
| 66 | [8-(1,3-benzodioxol-5-ylsulfonyl)-3,8-diazabicyclo[3.2.1]oct-3-yl](1H-1,2,3-triazol-5-yl)methanone |
| 67 | {8-[(2-methoxy-4-methylphenyl)sulfonyl]-3,8-diazabicyclo[3.2.1]oct-3-yl}(1H-1,2,3-triazol-5-yl)methanone |
| 68 | 2-chloro-6-{[3-(1H-1,2,3-triazol-5-ylcarbonyl)-3,8-diazabicyclo[3.2.1]oct-8-yl]sulfonyl}benzonitrile |
| 69 | [8-(2,3-dihydro-1-benzofuran-7-ylsulfonyl)-3,8-diazabicyclo[3.2.1]oct-3-yl](1H-1,2,3-triazol-5-yl)methanone |
| 70 | {8-[(2-chloro-5-fluorophenyl)sulfonyl]-3,8-diazabicyclo[3.2.1]oct-3-yl}(1H-1,2,3-triazol-5-yl)methanone |
| 71 | {8-[(2-chloro-3-fluorophenyl)sulfonyl]-3,8-diazabicyclo[3.2.1]oct-3-yl}(1H-1,2,3-triazol-5-yl)methanone |
| 72 | {8-[(4-fluoro-2-methoxyphenyl)sulfonyl]-3,8-diazabicyclo[3.2.1]oct-3-yl}(1H-1,2,3-triazol-5-yl)methanone |
| 73 | 4-methoxy-3-{[3-(1H-1,2,3-triazol-5-ylcarbonyl)-3,8-diazabicyclo[3.2.1]oct-8-yl]sulfonyl}benzonitrile |
| 74 | 4-chloro-3-{[3-(1H-1,2,3-triazol-5-ylcarbonyl)-3,8-diazabicyclo[3.2.1]oct-8-yl]sulfonyl}benzonitrile |
| 75 | sodium 5-({8-[(3,5-difluorophenyl)sulfonyl]-3,8-diazabicyclo[3.2.1]oct-3-yl}carbonyl)-1,2,3-triazol-1-ide |
| 76 | sodium 5-({8-[(3-fluorophenyl)sulfonyl]-3,8-diazabicyclo[3.2.1]oct-3-yl}carbonyl)-1,2,3-triazol-1-ide |

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formulae (IV) or (VIII). The present invention covers the compounds of general formula (I) which are disclosed in the Example Section of this text, infra.

The compounds according to the invention of general formula (I) can be prepared according to the following scheme 1. The scheme and procedures described below illustrate synthetic routes to the compounds of general formula (I) of the invention and are not intended to be limiting. It is clear to the person skilled in the art that the order of transformations as exemplified in scheme 1 can be modified in various ways. The order of transformations exemplified in this scheme is therefore not intended to be limiting. In addition, interconversion of any of the substituents, $R^1$, $R^2$, $R^3$, $R^4$, or $R^5$ can be achieved before and/or after the exemplified transformations. These modifications can be such as the introduction of protecting groups, cleavage of protecting groups, reduction or oxidation of functional groups, halogenation, metallation, substitution or formation and cleavage of ethers known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Two routes for the preparation of compounds of general formula (I) are described in scheme 1.

Scheme 1: Route for the preparation of compounds of general formula (I) in which $R^1$, $R^2$, $R^3$, $R^4$ and $R^5$ have the meaning as given for general formula (I), supra.

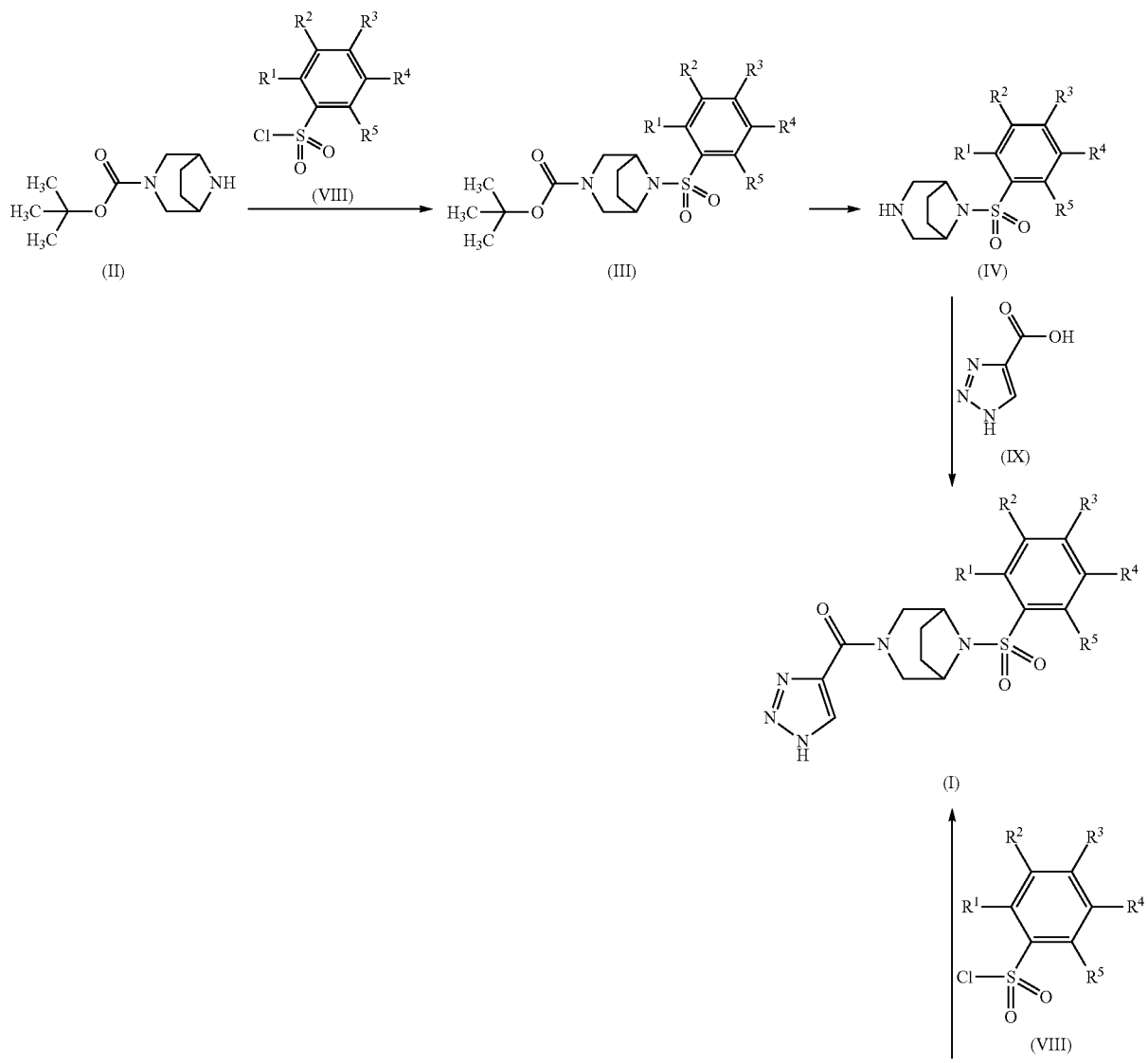

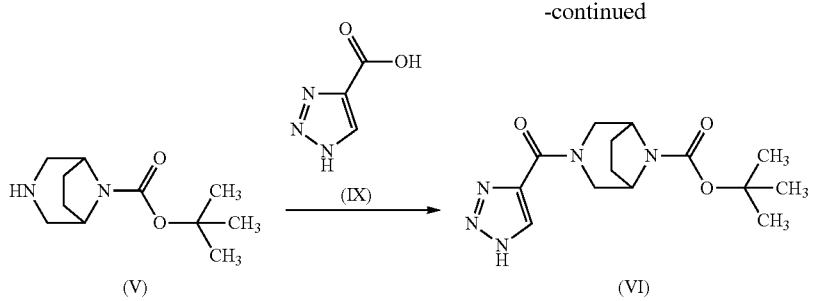

(V) (IX) (VI) (VII)

The starting materials required for the performance of the synthetic sequences outlined in scheme 1, namely tert-butyl-3,8-diazabicyclo[3.2.1]octane-3-carboxylate (formula (II)) and tert-butyl-3,8-diazabicyclo[3.2.1]octane-8-carboxylate (formula (V)) are well known to the person skilled in the art and are commercially available, for instance from Arkpharminc, Achemblock or ASM chemicals.

Compounds of the general formula (I) can be assembled according to Scheme 1 from tert-butyl-3,8-diazabicyclo[3.2.1]octane-3-carboxylate of formula (II) which can be reacted in a suitable solvent like, for example, NMP or DCM at reaction temperatures ranging from room temperature to the boiling point of the solvent, with an appropriate sulfonyl chloride of general formula (VIII) in the presence of a suitable base, for instance DIPEA, to form the Boc-protected sulfonamide intermediate of general formula ((III). The Boc-protected intermediate (III) can be deprotected in the presence of a suitable acid, for instance TFA in a suitable solvent, for instance DCM or DCE, or for instance with HCl in a suitable solvent, like for instance dioxane and optionally in the presence of scavengers like water to form intermediates of general formula (IV). Intermediates of general formula (IV) can be converted to compounds of general formula (I) of the present invention by reaction with 1H-1,2,3-triazole-5-carboxylic acid in the presence of a suitable coupling reagent, like for example HATU, in the presence of a suitable base, like for example DIPEA in an appropriate solvent, like for example NMP, DMF, DCM or THF at reaction temperatures ranging from room temperature to the boiling point of the solvent.

Alternatively, compounds of the general formula (I) can be synthesized starting from tert-butyl-3,8-diazabicyclo[3.2.1]octane-8-carboxylate (formula (V)) by reaction with 1H-1,2,3-triazole-5-carboxylic acid in the presence of a suitable coupling reagent, like for example HATU, in the presence of a suitable base, like for example DIPEA in an appropriate solvent, like for example NMP, DMF, DCM or THF at reaction temperatures ranging from room temperature to the boiling point of the solvent to form intermediate (VI). Deprotection of intermediate (VI) is possible with suitable acids, like for instance TFA, in a suitable solvent, for instance DCM or DCE, or for instance with HCl in a suitable solvent, like for instance dioxane. Intermediates of general formula (VII) can be converted to compounds of general formula (I) of the present invention by reaction with an appropriate sulfonyl chloride of general formula (VIII) in the presence of a suitable base, for instance DIPEA in a suitable solvent like, for example, NMP or DCM at reaction temperatures ranging from room temperature to the boiling point of the solvent.

In accordance with a second aspect, the present invention covers methods of preparing compounds of general formula (I) as defined supra, said methods comprising the step of allowing an intermediate compound of general formula (IV):

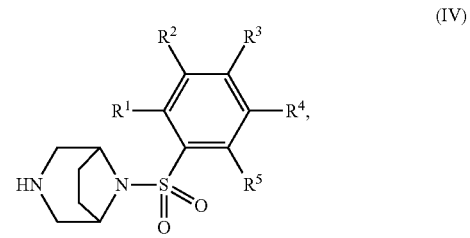

(IV)

in which $R^1$, $R^2$, $R^3$, $R^4$ and $R^5$ are as defined for the compound of general formula (I) as defined supra, to react with a compound of formula (IX):

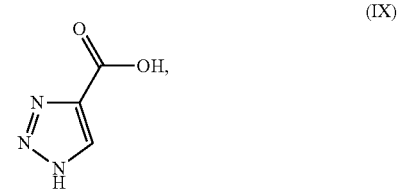

(IX)

thereby giving a compound of general formula (I):

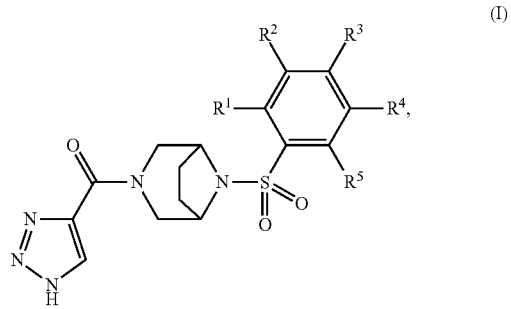

(I)

in which $R^1$, $R^2$, $R^3$, $R^4$ and $R^5$ are as defined supra.

In accordance with a third aspect, the present invention covers methods of preparing compounds of general formula (I) as defined supra, said methods comprising the step of allowing an intermediate compound of formula (VII):

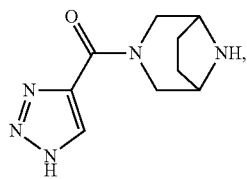

to react with a compound of general formula (VIII):

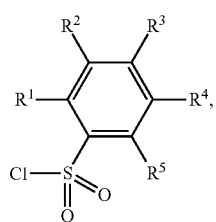

in which $R^1$, $R^2$, $R^3$, $R^4$ and $R^5$ are as defined for the compound of general formula (I) as defined supra,
thereby giving a compound of general formula (I):

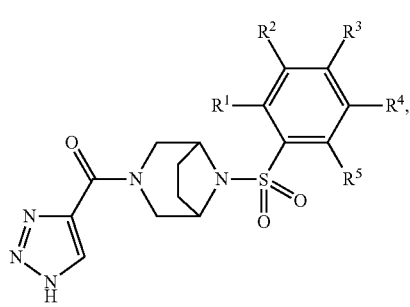

in which $R^1$, $R^2$, $R^3$, $R^4$ and $R^5$ are as defined supra.

The present invention covers methods of preparing compounds of the present invention of general formula (I), said methods comprising the steps as described in the Experimental Section herein.

The present invention covers the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Indications

Compounds of general formula (I) of the present invention demonstrate a valuable pharmacological spectrum of action, which could not have been predicted. Compounds of the present invention have surprisingly been found to effectively inhibit AKR1C3. For the major part of the structural range claimed, these substances show strong inhibition of AKR1C3 in vitro ($IC_{50}$ values of less than 10 nM) and predominantly even $IC_{50}$ around <1 nM.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases.

The term "treating" or "treatment" as stated throughout this document is used conventionally, e.g., the management or care of a subject for the purpose of combating, alleviating, reducing, relieving, improving the condition of, etc., of a disease or disorder, such as gynecological disorders, hyperproliferative disorders, metabolic disorders or inflammatory disorders. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention relates to a method for using the compounds of general formula (I), as described supra, or stereoisomers, tautomers, N-oxides, hydrates, solvates, and salts thereof, particularly pharmaceutically acceptable salts thereof, or mixtures of same thereof, to treat mammalian and human disorders and diseases, which include but are not limited to:
  gynecological disorders,
  metabolic disorders,
  hyperproliferative disorders, and
  inflammation disorders.

Gynecological disorders include any gynecological disease, disorder or condition per se. The term also includes but is not limited to, for example endometriosis-related gynecological disorders, conditions and diseases, polycystic ovary syndrome (PCOS)-related gynecological disorders, conditions and diseases, primary and secondary dysmenorrhea, dyspareunia, premature sexual maturity, uterine fibroids, uterine leiomyomas, and uterine bleeding disorders.

Examples of Endometriosis-related gynecological disorders, conditions and diseases include, but are not limited to: endometriosis as such, adenomyosis; endometriosis-associated pain; endometriosis-associated symptoms, wherein said symptoms are in particular dysmenorrhea, dyspareunia, dysuria, or dyschezia; endometriosis-associated proliferation; and pelvic hypersensitivity.

Examples of Polycystic ovary syndrome (PCOS)-related gynecological disorders, conditions and diseases include, but are not limited to: polycystic ovary syndrome (PCOS) and polycystic ovary associated symptoms wherein said symptoms are in particular hyperandrogenimia, hirsutims, acne, hair loss, metabolic phenotype in PCOS such as obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome type II diabetes, obesity.

Metabolic disorders include, but are not limited to, for example: hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome type II diabetes and obesity, independent of PCOS.

Hyperproliferative disorders, conditions and diseases include, but are not limited to, for example: benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, and ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to testicular cancer and hormone-dependent and hormone-independent prostate cancer including castration resistant prostate cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, and renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Leukemias include, but are not limited to, acute myeloid leukemia, acute lymphoblastic leukemia, chronic lymphocytic leukemia, chronic myelogenous leukemia, and hairy cell leukemia. Sarcomas include, but are not limited to, sarcoma of the soft tissue, osteosarcoma, malignant fibrous histiocytoma, lymphosarcoma, and rhabdomyosarcoma.

Inflammation disorders includes, but is not limited to, for example: any inflammatory disease, disorder or condition per se, any condition that has an inflammatory component associated with it, and/or any condition characterized by inflammation as a symptom, including, inter alia, acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever. The compounds of the present invention may also be useful in the treatment of fibromyalgia, myofascial disorders, viral infections (e.g. influenza, common cold, herpes zoster, hepatitis C and AIDS), bacterial infections, fungal infections, surgical or dental procedures, malignancies (e.g. breast cancer, colon cancer, and prostate cancer), arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, stroke, diabetes mellitus, autoimmune diseases, allergic disorders, rhinitis, ulcers, mild to moderately active ulcerative colitis, familial adenomatous polyposis, coronary heart disease, sarcoidosis, atopic dermatitis and keloids and any other disease with an inflammatory component. Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases.

The present invention preferably relates to a method for using the compounds of general formula (I), as described supra, or stereoisomers, tautomers, N-oxides, hydrates, solvates, and salts thereof, particularly pharmaceutically acceptable salts thereof, or mixtures of same thereof, to treat endometriosis and endometriosis-associated pain and symptomes, polycystic ovary syndrome, atopic dermatitis, keloids and prostate cancer including castration-resistant prostate cancer (CRPC).

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular gynecological disorders, metabolic disorders, hyperproliferative disorders, and inflammation disorders.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular gynecological disorders, metabolic disorders, hyperproliferative disorders, and inflammation disorders.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular gynecological disorders, metabolic disorders, hyperproliferative disorders, and inflammation disorders.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular in particular gynecological disorders, metabolic disorders, hyperproliferative disorders, and inflammation disorders.

In accordance with a further aspect, the present invention covers a method of treatment or prophylaxis of diseases, in particular gynecological disorders, metabolic disorders, hyperproliferative disorders, and inflammation disorders, using an effective amount of a compound of general formula (I), as described supra, or stereoisomers, tautomers, N-oxides, hydrates, solvates, and salts thereof, particularly pharmaceutically acceptable salts thereof, or mixtures of same.

These disorders (in particular gynecological disorders, metabolic disorders, hyperproliferative disorders, and inflammation disorders) have been well characterized in humans, but also exist with a similar etiology in other mammals, and can be treated by administering pharmaceutical compositions of the present invention.

Pharmaceutical Compositions

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Dosage

Based upon standard laboratory techniques known to evaluate compounds useful for the treatment of in particular gynecological disorders, metabolic disorders, hyperproliferative disorders, and inflammation disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combinations

The compounds according to the invention can be used alone or, if required, in combination with other active compounds.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

In accordance with another aspect, the present invention covers pharmaceutical combinations, in particular medicaments, comprising at least one compound of general formula (I) of the present invention and at least one or more further active ingredients, in particular for the treatment and/or prophylaxis the aforementioned disorders. The compounds of the present invention can be administered as the sole pharmaceutical agent or in combination with one or more other pharmaceutically active ingredients where the combination causes no unacceptable adverse effects. The present invention also covers such pharmaceutical combinations.

Particularly, the present invention covers a pharmaceutical combination, which comprises:
one or more first active ingredients, in particular compounds of general formula (I) as defined supra, and
one or more further active ingredients as described below.

In general, further active ingredients include but are not limited to for example: antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (aspirin, ibuprofen, naproxen, etodolac, celecoxib, colchicine).

Furthermore for example, the compounds of the present invention can be combined with known hormonal therapeutic agents.

In particular, the compounds of the present invention can be administered in combination or as co-medication with hormonal contraceptives. Hormonal contraceptives can be administered via oral, subcutaneous, transdermal, intrauterine or intravaginal route, for example as Combined Oral Contraceptives (COCs) or Progestin-Only-Pills (POPs) or hormone-containing devices like implants, patches or intravaginal rings.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate.

Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qlaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; Microlut containing levonorgestrel and Micronor containing norethindrone.

Other Progeston-Only forms are intrauterine devices (IUDs), for example Mirena Jaydess, Kyleeny containing levonorgestrel, or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel, or transdermal systems like contraceptive patches, for example Ortho-Evra containing ethinyl estradiol and norelgestromin or Apleek (Lisvy) containing ethinyl estradiol and gestodene.

A preferred embodiment of the present invention is the administration of a compound of general formula (I) in combination with a COC or a POP or other Progestin-Only forms as well as vaginal rings or contraceptive patches as mentioned above.

In addition to well-known medicaments which are already approved and on the market, the compounds of the present invention can be administered in combination with inhibitors of the P2X purinoceptor family (P2X3, P2X4), with inhibitors of IRAK4 and with antagonists of the prostanoid EP4 receptor.

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of microsomal prostaglandin E synthase (mPGES-1 or PTGES) and with functional blocking antibodies of the prolactin receptor and with inhibitors of chymase.

For tumour therapy further active ingredients include but are not limited to for example: 131I-chTNT, abarelix, abiraterone, aclarubicin, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumabpentetreotide, nilotinib, nilutamide, nimorazole, nimotuzumab, nimustine, nintedanib, nitracrine, nivolumab, obinutuzumab, octreotide, ofatumumab, olaparib, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

For the treatment of prostate cancer the present invention particularly covers a pharmaceutical combination which comprises further active ingredients used for the treatment of prostate cancer including, but not limited to:

anti-androgens for example Flutamide (Eulexin), Bicalutamide (Casodex), Nilutamide (Nilandron), Enzaluatmide (Xtandi), ODM-201.

CYP17A1 inhibitors for example abiraterone and abiraterone metabolites, 5 alpha reductase inhibitors, for example finasteride or dutasteride.

androgen-deprivation therapies (ADT) including GNRHa and GNRH antagonists, LHRHagonists, for example Leuprolide (Lupron, Eligard), Goserelin (Zoladex), Triptorelin (Trelstar), Histrelin (Vantas) or LHRH agonists, for example Degarelix. Androgen-deprivation therapies (ADT) can be administered alone or together with anti-androgens, 5 alpha reductase inhibitors, or CYP17A1 inhibitors.

For the prevention and treatment of cancers which are resistant to chemotherapeutic agents in particular to anthracyclines the present invention particularly covers a pharmaceutical combination, which comprises chemotherapeutic agents comprising an oxo-group, which can be reduced by the enzymatic activity of AKR1C3 as further active ingredient. An example for such chemotherapeutic agents are anthracyclines, such as but not limited to daunorubicin, doxorubicin, epirubicin and idarubicin. According to the invention the compounds of the present invention are administered concomitant with the chemotherapeutic agent in particular with an anthracycline.

For the prevention and treatment side effects related to anthracycline treatments such as cardiomyopathy the present invention particularly covers a pharmaceutical combination, which comprises anthracyclines as further active ingredient.

EXPERIMENTAL SECTION

NMR peak forms are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), $δ_i$ (intensity$_i$), $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

| Abbreviation | Meaning |
| --- | --- |
| Ac$_2$O | acetic anhydride |
| AcOH | acetic acid (ethanoic acid) |
| aq. | aqueous |
| Boc | tert-butoxycarbonyl |
| br | broad ($^1$H-NMR signal) |
| cat. | catalytic |
| conc. | concentrated |
| CI | chemical ionisation |
| d | doublet |
| DAD | diode array detector |
| DBU | 1,8-diazabicyclo(5.4.0)undec-7-ene |
| DCC | N,N'-dicyclohexylcarbodiimide |
| DCM | dichloromethane |
| dd | double-doublet |
| DIC | N,N'-diisopropylcarbodiimide |
| DIPEA | diisopropylethylamine |
| DMA | N,N-dimethylacetamide |
| DMF | N,N-dimethylformamide |
| DMSO | dimethylsulfoxide |
| dt | double-triplet |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour(s) |
| HATU | 1-[bis(dimethylamino)methylene]-1H-1,2,3-triazolo[4,5-b]pyridinium 3-oxid hexafluorophosphate |
| HBTU | (o-benzotriazole-10yl)-N,N,N',N,-tetramethyluronium hexafluorophosphate |
| HCl | hydrochloric acid |
| HPLC | high performance liquid chromatography |
| LC-MS | liquid chromatography mass spectrometry |
| m | multiplet |
| min | minute(s) |
| MeCN | acetonitrile |
| MeOH | methanol |
| MS | mass spectrometry |
| NBS | N-bromosuccinimide |
| NCS | N-chlorosuccinimide |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| Pd/C | palladium on activated charcoal |

TABLE 1-continued

| Abbreviation | Meaning |
| --- | --- |
| PdCl$_2$(dppf) | [1,1'-bis(diphenylphosphino)ferrocene]dichloropalladium(II) |
| Pd(dba)$_2$ | bis(dibenzylideneacetone)palladium |
| q | quartet |
| r.t. or rt or RT | room temperature |
| rac | racemic |
| Rt | retention time (as measured either with HPLC or UPLC) in minutes |
| s | singlet |
| sat. | saturated |
| SIBX | stabilized 2-iodoxybenzoic acid |
| SM | starting material |
| SQD | Single-Quadrupole-Detector |
| t | triplet |
| T3P | propylphosphonic anhydride |
| TBAF | tetra-n-butylammonium fluoride |
| TBDMS | tert-butyldimethylsilyl |
| TBTU | N-[(1H-benzotriazol-1-yloxy)(dimethylamino)methylene]-N-methylmethanaminium tetrafluoroborate |
| td | triple-doublet |
| TEA | triethylamine |
| TFA | trifluoroacetic acid |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Method 1:
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method 3:
Instrument: Waters Acquity UPLCMS SingleQuad; Column: Acquity UPLC BEH C18 1.7 µm 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 4:
System: UPLC Acquity (Waters) with PDA Detector and Waters ZQ mass spectrometer; Column: Acquity BEH C18 1.7 µm 2.1×50 mm; Temperature: 60° C.; Solvent A: Water+0.1% Formic Acid; Solvent B: Acetonitrile; Gradient: 99% A to 1% A (1.6 min) to 1% A (0.4 min); Flow: 0.8 mL/min; Injektion Volume: 1.0 µl (0.1 mg-1 mg/mL Sample Concentration); Detection: PDA Scan Region 210-400 nm—plus fixed wavelength 254 nm; MS ESI (+), Scan region 170-800 m/z Method 5:
System: Waters Aqcuity UPC2: Solvent Manager, Sample Manager, Column Manager, PDA, QDa MS; Column: Viridis BEH 2-EP 5 µm 100×4.6 mm; Solvent: A=CO2 B=Methanol+0.5% Vol. NH3 (32%); Flow: 4.0 mL/min; Gradient: 0-7 min 5-55% B; Pressure: 100 bar; Temperature: 40° C.; Detection: DAD 254 nm Preparative Chromatography on HPLC Systems:
For the purification of some intermediates and examples preparative reversed phase or normal phase systems were used. Available systems were:

Labomatic, Pump: HD-5000, Fraction Collector: LABOCOL Vario-4000, UV-Detector: Knauer UVD 2.1S; Column: Chromatorex RP C18 10 µm 125×30 mm, eluent: A: water+0.1 vol % formic acid (99%), eluent B: acetonitrile; detection: UV 254 nm; software: SCPA PrepCon5.

Waters autopurification system: Pump 2545, Sample Manager 2767, CFO, DAD 2996, ELSD 2424, SQD; Column: XBrigde C18 5 µm 100×30 mm; eluent A: water+0.1% Vol. formic acid, eluent B: acetonitrile; flow: 50 mL/min; temperature: room temperature; detection: DAD scan range 210-400 nm; MS ESI+, ESI−, scan range 160-1000 m/z.

Waters autopurification system: Pump 2545, Sample Manager 2767, CFO, DAD 2996, ELSD 2424, SQD; Column: XBrigde C18 5 µm 100×30 mm; eluent A: water+0.2 vol % aqueous ammonia (32%), eluent B: acetonitrile; flow: 50 mL/min; temperature: room temperature; detection: DAD scan range 210-400 nm; MS ESI+, ESI−, scan range 160-1000 m/z.

Column Chromatography on Silica Gel:
For the purification of some intermediates and examples a column chromatography ("flash chromatography") on silica gel was performed using devices (Isolera®) from the company Biotage. Cartridges prefilled with silica gel in different sizes were used, for example "SNAP Cartridge, KP_SIL" from the company Biotage or "Interchim Puriflash Silica HP 15UM flash column" from the company Interchim.

EXPERIMENTAL SECTION—INTERMEDIATES

Intermediate 1

3,8-diazabicyclo[3.2.1]oct-3-yl(1H-1,2,3-triazol-4-yl)methanone

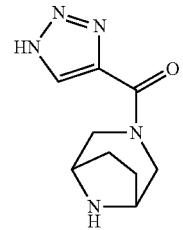

Step 1.1: tert-butyl 3-(1H-1,2,3-triazol-4-ylcarbonyl)-3,8-diazabicyclo[3.2.1]octane-8-carboxylate

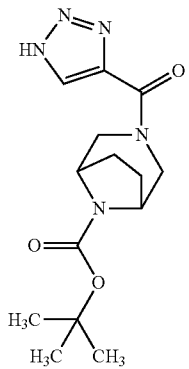

To a stirred solution of 500 mg (2.36 mmol) tert-butyl 3,8-diazabicyclo[3.2.1]octane-8-carboxylate in 12 mL NMP were added 532 mg 1H-1,2,3-triazole-4-carboxylic acid (4.71 mmol, 2 eq), 1.23 mL DIPEA (7.07 mmol, 3 eq) and 1.791 g HATU (4.71 mmol, 2 eq). After stirring overnight at RT, the solution was subjected to preparative HPLC to yield 378 mg (52%) tert-butyl 3-(1H-1,2,3-triazol-4-ylcarbonyl)-3,8-diazabicyclo[3.2.1]octane-8-carboxylate.

LC-MS (Method 3): Rt=0.91 min; MS (ESIpos): m/z=308 [M+H]+

¹H-NMR (500 MHz, DMSO-d6) δ[ppm]: 1.43 (9H), 1.53-1.72 (2H), 1.83 (2H), 2.92 (1H), 3.33 (1H), 4.14 (1H), 4.21 (1H), 4.30 (1H), 4.40 (1H), 8.29 (1H), 15.22 (1H).

Step 2: 3,8-diazabicyclo[3.2.1]oct-3-yl(1H-1,2,3-triazol-4-yl)methanone

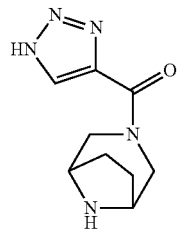

To a stirred and cooled (ice-bath) solution of 272 mg (887 µmol) tert-butyl-3-(1H-1,2,3-triazol-4-ylcarbonyl)-3,8-diazabicyclo[3.2.1]octane-8-carboxylate in 6 mL DCM were added 0.3 mL water and 3 mL TFA. After 3 h, the mixture was evaporated in vacuo, triturated with toluene and reevaporated to yield 376 mg (200%) crude 3,8-diazabicyclo[3.2.1]oct-3-yl(1H-1,2,3-triazol-4-yl)methanone as TFA adduct which was used without further purification in the next step.

SFC-MS (Method 5): Rt=1.74 min; MS (ESIpos): m/z=208 [M+H]+

¹H-NMR (500 MHz, DMSO-d6) δ[ppm]: 1.67-2.00 (4H), 3.19 (1H), 3.61 (1H), 4.11 (2H), 4.40 (1H), 4.70 (1H), 8.40 (1H).

Intermediate 2

8-(phenylsulfonyl)-3,8-diazabicyclo[3.2.1]octane

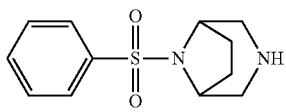 [SMILES: O=S(=O)(c1ccccc1)N1C2CCC1CNC2]

Step 2.1: tert-butyl-8-(phenylsulfonyl)-3,8-diazabicyclo[3.2.1]octane-3-carboxylate

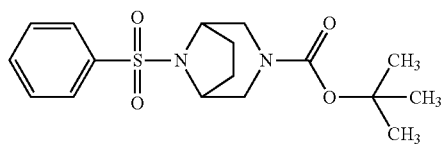 [SMILES: CC(C)(C)OC(=O)N1CC2CCC(C1)N2S(=O)(=O)c1ccccc1]

To a stirred solution of 100 mg (0.47 mmol) tert-butyl-3,8-diazabicyclo[3.2.1]octane-3-carboxylate in 2 ml DCE were added at RT 246 µL DIPEA (1.41 mmol, 3 eq) and 90 µL benzenesulfonyl chloride (125 mg, 0.71 mmol, 1.5 eq) and the mixture was stirred overnight at RT. The organic phase was washed three times with aqueous NaHCO3 solution (10%) and two times with water, dried and evaporated to yield 168 mg (101%) of the title compound.

LC-MS (Method 3): Rt=1.26 min; MS (ESIpos): m/z=353 [M+H]+

¹H-NMR (500 MHz, DMSO-d6) δ[ppm]: 1.19 (2H), 1.36 (11H), 2.87 (1H), 3.01 (1H), 3.75 (2H), 4.19 (2H), 7.60 (2H), 7.70 (1H), 7.87 (2H).

Step 2.2: 8-(phenylsulfonyl)-3,8-diazabicyclo[3.2.1]octane

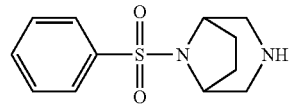

To a stirred solution of 166 mg (0.47 mmol) tert-butyl-8-(phenylsulfonyl)-3,8-diazabicyclo[3.2.1]octane-3-carboxylate in 1 mL DCM were added at RT 0.1 mL water and 3 mL TFA. After 3 h, the mixture was evaporated in vacuo, redissolved in tert-butanol and freeze-dried to yield 171 mg (143%) crude 8-(phenylsulfonyl)-3,8-diazabicyclo[3.2.1]octane as TFA-adduct which was used without further purification in the next step.

LC-MS (Method 1): Rt=0.54 min; MS (ESIpos): m/z=253 [M+H]+

¹H-NMR (500 MHz, DMSO-d6) δ[ppm]: 1.40 (2H), 1.77 (2H), 3.19-3.51 (4H), 4.37 (2H), 7.55-7.66 (2H), 7.74 (1H), 7.90 (1H), 8.25-9.50 (2H).

Intermediate 3

8-{[2-(trifluoromethyl)phenyl]sulfonyl}-3,8-diazabicyclo[3.2.1]octane

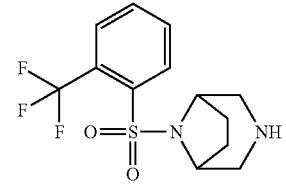 [SMILES: O=S(=O)(c1ccccc1C(F)(F)F)N1C2CCC1CNC2]

Step 3.1: tert-butyl-8-{[2-(trifluoromethyl)phenyl]sulfonyl}-3,8-diazabicyclo[3.2.1]octane-3-carboxylate

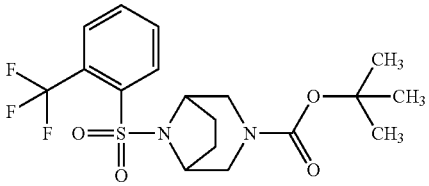 [SMILES: CC(C)(C)OC(=O)N1CC2CCC(C1)N2S(=O)(=O)c1ccccc1C(F)(F)F]

To a stirred solution of 4.246 g (20 mmol) tert-butyl-3,8-diazabicyclo[3.2.1]octane-3-carboxylate in 100 ml DCM were added 14 ml DIPEA (80 mmol, 4 eq) and 9.78 g 2-(trifluoromethyl)benzenesulfonyl chloride (40.0 mmol, 2 eq) and the mixture was stirred overnight at RT. The organic phase was removed in vacuo and the residue was subjected to flash chromatography (ethyl acetate/hexane) to yield 8.18 g (97%) of the title compound.

LC-MS (Method 1): Rt=1.36 min; MS (ESIpos): m/z=365 [M-tBu+H]$^+$ $^1$H-NMR (500 MHz, DMSO-d6) δ[ppm]: 1.38 (9H), 1.51-1.71 (4H), 2.83 (1H), 3.01 (1H), 3.76 (2H), 4.23 (2H), 7.91 (2H), 8.05 (1H), 8.27 (1H).

Step 3.2: 8-{[2-(trifluoromethyl)phenyl]sulfonyl}-3,8-diazabicyclo[3.2.1]octane

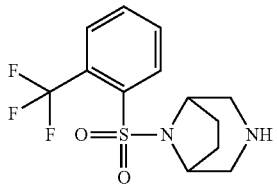 [SMILES: O=S(=O)(c1ccccc1C(F)(F)F)N1C2CCC1CNC2]

To a stirred solution of 8 g (19.45 mmol) tert-buty-8-{[2-(trifluoromethyl)phenyl]sulfonyl}-3,8-diazabicyclo[3.2.1]octane-3-carboxylate in 64 mL DCM were added 3.3 mL water and 64 mL TFA. After 3 h, the mixture was evaporated in vacuo, triturated with toluene and reevaporated. The residue was redissolved in DCM, washed with aqueous NaHCO$_3$ solution (10%) and water and the organic phase was dried and evaporated to yield 6.20 g (95%) of the title compound 8-{[2-(trifluoromethyl)phenyl]sulfonyl}-3,8-diazabicyclo[3.2.1]octane.

LC-MS (Method 1): Rt=0.69 min; MS (ESIpos): m/z=321 [M+H]$^+$ $^1$H-NMR (500 MHz, DMSO-d6) δ[ppm]: 1.54 (2H), 1.79 (2H), 2.60 (2H), 2.71 (2H), 4.02 (2H), 7.90 (2H), 8.03 (1H), 8.27 (1H).

Intermediate 4

8-[(3,5-difluorophenyl)sulfonyl]-3,8-diazabicyclo[3.2.1]octane hydrochloride (1:1)

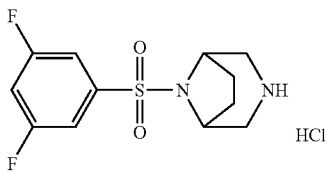 [SMILES: O=S(=O)(c1cc(F)cc(F)c1)N1C2CCC1CNC2 ; Cl]

Step 4.1: tert-butyl-8-[(3,5-difluorophenyl)sulfonyl]-3,8-diazabicyclo[3.2.1]octane-3-carboxylate

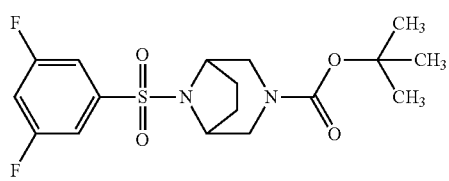 [SMILES: CC(C)(C)OC(=O)N1CC2CCC(C1)N2S(=O)(=O)c1cc(F)cc(F)c1]

To a stirred solution of 100 mg (0.47 mmol) tert-butyl-3,8-diazabicyclo[3.2.1]octane-3-carboxylate in 2 ml DCE were added at RT 246 μL DIPEA (1.41 mmol, 3 eq) and 150 mg 3,5-difluorobenzenesulfonyl chloride (0.71 mmol, 1.5 eq) and the mixture was stirred overnight at RT. The organic phase was washed three times with aqueous NaHCO$_3$ solution (10%) and one time with water, dried and evaporated to yield 188 mg (103%) of the title compound.

LC-MS (Method 1): Rt=1.34 min; MS (ESIpos): m/z=389 [M+H]$^+$ $^1$H-NMR (500 MHz, DMSO-d6) δ[ppm]: 1.30 (2H), 1.38 (9H), 1.45 (2H), 2.89 (1H), 3.03 (1H), 3.76 (2H), 4.29 (2H), 7.68 (3H).

Step 4.2: 8-[(3,5-difluorophenyl)sulfonyl]-3,8-diazabicyclo[3.2.1]octane hydrochloride (1:1)

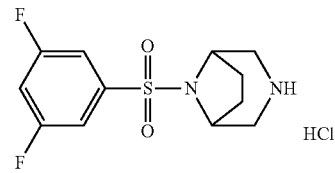

To a stirred solution of 183 mg (0.47 mmol) tert-butyl 8-[(3,5-difluorophenyl)sulfonyl]-3,8-diazabicyclo[3.2.1]octane-3-carboxylate in 3 mL ethanol were added with ice-cooling 1.8 mL HCl 4M in dioxane (7 mmol, 15 eq) and the mixture was stirred for 2 h at RT. Another 1 mL HCl 4M in dioxane were added and after 3 h stirring at RT, the mixture was evaporated in vacuo and freeze-dried from tert-butanol to yield 157 mg (103%) of the title compound 8-[(3,5-difluorophenyl)sulfonyl]-3,8-diazabicyclo[3.2.1]octane hydrochloride (1:1).

LC-MS (Method 2): R$_t$=0.64 min; MS (ESIpos): m/z=289 [M+H]$^+$ $^1$H-NMR (400 MHz, DMSO-d6) δ[ppm]: 1.54 (2H) 1.94 (2H) 3.11 (2H) 3.18 (2H), 4.45 (2H) 7.72 (3H), 8.87-9.92 (2H)

Intermediate 5

8-[(3-fluorophenyl)sulfonyl]-3,8-diazabicyclo[3.2.1]octane hydrochloride (1:1)

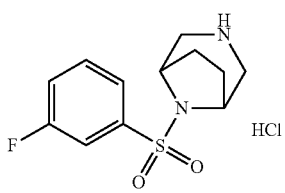 [SMILES: O=S(=O)(c1cccc(F)c1)N1C2CCC1CNC2 ; Cl]

Step 5.1: tert-butyl-8-[(3-fluorophenyl)sulfonyl]-3,8-diazabicyclo[3.2.1]octane-3-carboxylate

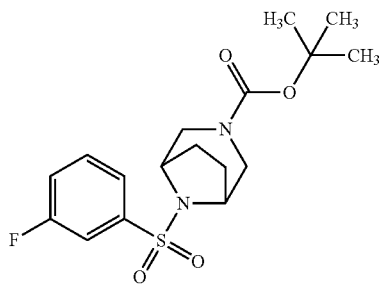 [SMILES: CC(C)(C)OC(=O)N1CC2CCC(C1)N2S(=O)(=O)c1cccc(F)c1]

To a stirred solution of 500 mg (2.36 mmol) tert-butyl 3,8-diazabicyclo[3.2.1]octane-3-carboxylate in DCM were added 1.6 ml DIPEA (9.4 mmol, 4 eq) and 380 μL 3-fluorobenzenesulfonyl chloride (2.82 mmol, 1.2 eq) and the mixture was stirred overnight at RT. The organic phase was removed in vacuo and the residue was subjected to flash chromatography (ethyl acetate/hexane) to yield 844 mg (97%) of the title compound.

LC-MS (Method 2): $R_t$=1.28 min; MS (ESIpos): m/z=315 M-t-Bu$^+$ $^1$H-NMR (400 MHz, CHLOROFORM-d) δ [ppm]: 7.68 (1H), 7.58 (1H), 7.51 (1H), 7.35-7.28 (1H), 4.19 (2H), 3.93 (1H), 3.77 (1H), 3.19-2.96 (2H), 1.69-1.54 (4H), 1.44 (s, 9H)

Step 5.2: 8-[(3-fluorophenyl)sulfonyl]-3,8-diazabicyclo[3.2.1]octane hydrochloride (1:1)

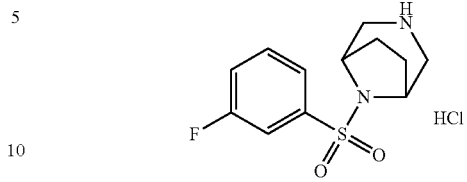

To a stirred solution of 840 mg (2.27 mmol) 8-[(3-fluorophenyl)sulfonyl]-3,8-diazabicyclo[3.2.1]octane-3-carboxylate in 10 mL ethanol were added 8.5 mL HCl 4M in dioxane (34 mmol, 15 eq) and the mixture was stirred for 72 h at RT. The mixture was evaporated in vacuo, triturated with diethylether, filtered and dried in vacuo to yield 735 mg (105%) of the title compound 8-[(3-fluorophenyl)sulfonyl]-3,8-diazabicyclo[3.2.1]octane hydrochloride (1:1).

LC-MS (Method 2): $R_t$=0.84 min; MS (ESIpos): m/z=271 [M+H]$^+$ $^1$H-NMR (400 MHz, DMSO-d6) δ[ppm]: 1.36-1.54 (2H) 1.81-1.97 (2H) 2.98-3.13 (2H) 3.13-3.25 (2H), 4.40 (2H) 7.57-7.65 (1H), 7.66-7.73 (1H) 7.73-7.83 (2H), 9.10-9.90 (1H)

The following intermediates were synthesized in analogy to procedures given for intermediates 2 to 5 using the appropriate sulfonyl chloride.

| Intermediate | Structure IUPAC-Name | LC-MS |
|---|---|---|
| 6 | 8-[(2-chlorophenyl)sulfonyl]-3,8-diazabicyclo[3.2.1]octane | LC-MS (Method 1): $R_t$ = 0.56 min; MS (ESIpos): m/z = 288 [M + H]$^+$ |
| 7 | 8-{[3-(pentafluoro-lambda$^6$-sulfanyl)phenyl]sulfonyl}-3,8-diazabicyclo[3.2.1]octane | LC-MS (Method 4): $R_t$ = 0.77 min; MS (ESIpos): m/z = 379 [M + H]$^+$ |
| 8 | 8-[(3,5-dichlorophenyl)sulfonyl]-3,8-diazabicyclo[3.2.1]octane | LC-MS (Method 4): $R_t$ = 0.75 min; MS (ESIpos): m/z = 322 [M + H]$^+$ |

| Intermediate | Structure IUPAC-Name | LC-MS |
|---|---|---|
| 9 | 8-{[3,5-bis(trifluoromethyl)phenyl]sulfonyl}-3,8-diazabicyclo[3.2.1]octane | LC-MS (Method 1): Rt = 0.92 min; MS (ESIpos): m/z = 389 [M + H]$^+$ |
| 10 | 8-[(5-chlorothiophen-2-yl)sulfonyl]-3,8-diazabicyclo[3.2.1]octane | LC-MS (Method 1): Rt = 0.61 min; MS (ESIpos): m/z = 293 [M + H]$^+$ |
| 11 | 8-[(2,5-difluorophenyl)sulfonyl]-3,8-diazabicyclo[3.2.1]octane | LC-MS (Method 1): Rt = 0.97 min; MS (ESIpos): m/z = 289 [M + H]$^+$ |
| 12 | 8-[(3-methylphenyl)sulfonyl]-3,8-diazabicyclo[3.2.1]octane | LC-MS (Method 1): Rt = 0.72 min; MS (ESIpos): m/z = 268 [M + H]$^+$ |
| 13 | 8-[(4-methylphenyl)sulfonyl]-3,8-diazabicyclo[3.2.1]octane | LC-MS (Method 1): Rt = 0.72 min; MS (ESIpos): m/z = 268 [M + H]$^+$ |

| Intermediate | Structure IUPAC-Name | LC-MS |
|---|---|---|
| 14 | 8-[(2-fluorophenyl)sulfonyl]-3,8-diazabicyclo[3.2.1]octane | LC-MS (Method 1): Rt = 0.66 min; MS (ESIpos): m/z = 271 [M + H]$^+$ |
| 15 | 8-[(4-fluorophenyl)sulfonyl]-3,8-diazabicyclo[3.2.1]octane | LC-MS (Method 1): Rt = 0.66 min; MS (ESIpos): m/z = 272 [M + H]$^+$ |
| 16 | 8-[3,8-diazabicyclo[3.2.1]oct-8-ylsulfonyl]benzonitrile | LC-MS (Method 1): Rt = 0.63 min; MS (ESIpos): m/z = 278 [M + H]$^+$ |
| 17 | 8-[(3,5-dimethylphenyl)sulfonyl]-3,8-diazabicyclo[3.2.1]octane | LC-MS (Method 1): Rt = 0.80 min; MS (ESIpos): m/z = 281 [M + H]$^+$ |
| 18 | 8-[(2,5-dimethylphenyl)sulfonyl]-3,8-diazabicyclo[3.2.1]octane | LC-MS (Method 1): Rt = 0.66 min; MS (ESIpos): m/z = 281 [M + H]$^+$ |

-continued

| Intermediate | Structure IUPAC-Name | LC-MS |
|---|---|---|
| 19 | 8-[(3-methoxyphenyl)sulfonyl]-3,8-diazabicyclo[3.2.1]octane | LC-MS (Method 1): Rt = 0.69 min; MS (ESIpos): m/z = 284 [M + H]$^+$ |
| 20 | 8-[(4-methoxyphenyl)sulfonyl]-3,8-diazabicyclo[3.2.1]octane | LC-MS (Method 1): Rt = 0.68 min; MS (ESIpos): m/z = 283 [M + H]$^+$ |
| 21 | 8-[(4-chlorophenyl)sulfonyl]-3,8-diazabicyclo[3.2.1]octane | LC-MS (Method 1): Rt = 0.77 min; MS (ESIpos): m/z = 287 [M + H]$^+$ |
| 22 | 8-[(3,4-difluorophenyl)sulfonyl]-3,8-diazabicyclo[3.2.1]octane | LC-MS (Method 1): Rt = 0.72 min; MS (ESIpos): m/z = 290 [M + H]$^+$ |
| 23 | 8-[(2,6-difluorophenyl)sulfonyl]-3,8-diazabicyclo[3.2.1]octane | LC-MS (Method 1): Rt = 0.64 min; MS (ESIpos): m/z = 289 [M + H]$^+$ |

-continued

| Intermediate | Structure IUPAC-Name | LC-MS |
|---|---|---|
| 24 | 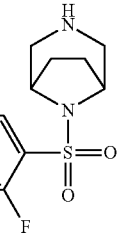<br>8-[(2,4-difluorophenyl)sulfonyl]-3,8-diazabicyclo[3.2.1]octane | LC-MS (Method 1): Rt = 0.69 min; MS (ESIpos): m/z = 289 [M + H]$^+$ |
| 25 | 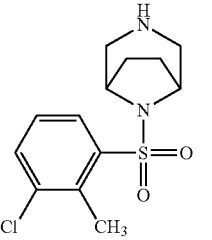<br>8-[(3-chloro-2-methylphenyl)sulfonyl]-3,8-diazabicyclo[3.2.1]octane | LC-MS (Method 1): Rt = 0.82 min; MS (ESIpos): m/z = 301 [M + H]$^+$ |
| 26 | 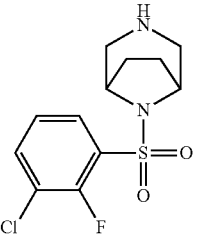 [SMILES: O=S(=O)(c1cccc(Cl)c1F)N1C2CCC1CNC2]<br>8-[(3-chloro-2-fluorophenyl)sulfonyl]-3,8-diazabicyclo[3.2.1]octane | LC-MS (Method 1): Rt = 0.76 min; MS (ESIpos): m/z = 305 [M + H]$^+$ |
| 27 | 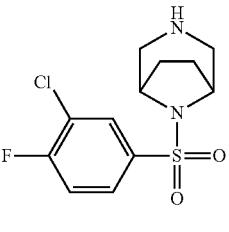<br>8-[(3-chloro-4-fluorophenyl)sulfonyl]-3,8-diazabicyclo[3.2.1]octane | LC-MS (Method 1): Rt = 0.78 min; MS (ESIpos): m/z = 305 [M + H]$^+$ |
| 28 | 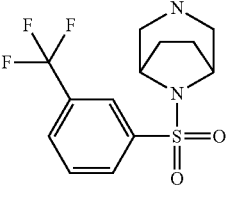<br>8-{[3-(trifluoromethyl)phenyl]sulfonyl}-3,8-diazabicyclo[3.2.1]octane | LC-MS (Method 1): Rt = 0.76 min; MS (ESIpos): m/z = 321 [M + H]$^+$ |

-continued

| Intermediate | Structure IUPAC-Name | LC-MS |
|---|---|---|
| 29 | 8-[(2,5-dichlorophenyl)sulfonyl]-3,8-diazabicyclo[3.2.1]octane | LC-MS (Method 1): Rt = 0.80 min; MS (ESIpos): m/z = 321 [M + H]$^+$ |
| 30 | 8-[(3-bromophenyl)sulfonyl]-3,8-diazabicyclo[3.2.1]octane | LC-MS (Method 1): Rt = 0.66 min; MS (ESIpos): m/z = 331 [M + H]$^+$ |
| 31 | 8-[(2-bromophenyl)sulfonyl]-3,8-diazabicyclo[3.2.1]octane | LC-MS (Method 1): Rt = 0.70 min; MS (ESIpos): m/z = 331 [M + H]$^+$ |
| 32 | 8-{[3-(trifluoromethoxy)phenyl]sulfonyl}-3,8-diazabicyclo[3.2.1]octane | LC-MS (Method 1): Rt = 0.80 min; MS (ESIpos): m/z = 338 [M + H]$^+$ |
| 33 | 8-{[5-chloro-2-(trifluoromethyl)phenyl]sulfonyl}-3,8-diazabicyclo[3.2.1]octane | LC-MS (Method 1): Rt = 0.80 min; MS (ESIpos): m/z = 355 [M + H]$^+$ |

-continued

| Intermediate | Structure IUPAC-Name | LC-MS |
|---|---|---|
| 34 | 3-[3,8-diazabicyclo[3.2.1]oct-8-ylsulfonyl]benzonitrile | LC-MS (Method 1): Rt = 0.54 min; MS (ESIpos): m/z = 278 [M + H]⁺ |
| 35 | 8-{[4-(trifluoromethyl)phenyl]sulfonyl}-3,8-diazabicyclo[3.2.1]octane | LC-MS (Method 1): Rt = 0.72 min; MS (ESIpos): m/z = 321 [M + H]⁺ |
| 36 | 4-[3,8-diazabicyclo[3.2.1]oct-8-ylsulfonyl]phenol | LC-MS (Method 1): Rt = 0.48 min; MS (ESIpos): m/z = 269 [M + H]⁺ |

EXPERIMENTAL SECTION—EXAMPLES

Example 1

[8-(phenylsulfonyl)-3,8-diazabicyclo[3.2.1]oct-3-yl](1H-1,2,3-triazol-4-yl)methanone

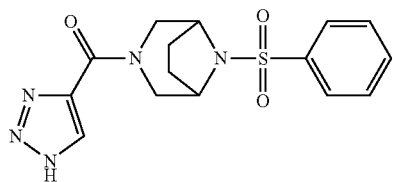 [SMILES: O=C(c1c[nH]nn1)N1CC2CCC(C1)N2S(=O)(=O)c1ccccc1]

Procedure 1.1:

To a stirred and cooled solution of 1.87 g (57% purity, 5.11 mmol)-3,8-diazabicyclo[3.2.1]oct-3-yl(1H-1,2,3-triazol-4-yl)methanone (Intermediate 1) in 25 mL NMP were added at 0° C. 4.45 mL (5 eq, 25.5 mmol) DIPEA and 0.63 g (0.7 eq, 3.57 mmol) benzenesulfonyl chloride and the mixture was stirred for 1 h at 0° C. After stirring overnight at RT, the mixture was subjected to preparative HPLC to yield 215 mg (0.61 mmol, 12%) of the title compound 3,8-diazabicyclo[3.2.1]oct-3-yl(1H-1,2,3-triazol-4-yl)methanone.

LC-MS (Method 1): Rt=0.85 min; MS (ESIpos): m/z=348 [M+H]⁺

¹H-NMR (400 MHz, DMSO-d6) δ[ppm]: 1.193 (3.38), 1.211 (5.65), 1.228 (4.02), 1.262 (0.76), 1.382 (1.39), 1.406 (3.26), 1.427 (1.85), 1.510 (1.94), 2.323 (0.45), 2.327 (0.62), 2.331 (0.43), 2.518 (2.26), 2.523 (1.43), 2.665 (0.45), 2.669 (0.63), 2.673 (0.45), 2.963 (3.11), 2.992 (3.35), 3.397 (2.90), 4.282 (3.57), 4.337 (7.53), 4.368 (3.35), 7.593 (6.59), 7.597 (2.73), 7.611 (16.00), 7.631 (11.11), 7.690 (3.31), 7.693 (6.32), 7.696 (3.91), 7.707 (2.79), 7.711 (8.65), 7.716 (2.33), 7.727 (1.88), 7.730 (2.99), 7.885 (11.98), 7.889 (15.82), 7.894 (4.11), 7.907 (12.63).

Procedure 1.2:

To a stirred solution of 504 mg (2 mmol) 8-(phenylsulfonyl)-3,8-diazabicyclo[3.2.1]octane (Intermediate 2) in 6 mL NMP were added at RT 452 mg (2 eq, 4 mmol) 1H-1,2,3-triazole-5-carboxylic acid, 1045 µL (3 eq, 6 mmol) DIPEA and 1.52 g (2 eq, 4 mmol) HATU and the mixture was stirred for 6 h. The mixture was taken up in ethyl acetate, washed with water, dried with sodium sulfate, evaporated and the residue was subjected to flash chromatography using ethyl acetate and hexane to yield 787 mg (1.93 mmol, 96%) of the title compound 3,8-diazabicyclo[3.2.1]oct-3-yl(1H-1,2,3-triazol-4-yl)methanone.

Procedure 1.3:

To a solution of tert-butyl-3,8-diazabicyclo[3.2.1]octane-3-carboxylate (0.3 mmol, 750 µL, 0.4 M) in DCE were added benzenesulfonyl chloride (0.45 mmol, 900 µL, 0.5M, 1.5 eq) in DCE and 0.9 mmol DIPEA (156 µL, 3 eq) and the mixture was shaken overnight at RT. 2 mL TFA/DCE 3:1 were added and the mixture was shaken at RT for 3 h. After evaporation of the solvent, 1H-1,2,3-triazole-5-carboxylic acid (0.6 mmol, 1.2 mL, 2 eq, 0.5M) in NMP, 928 µL DIPEA (3.6 mmol, 12 eq; adjustment of pH to 8) and HATU (0.6 mmol, 1.2 mL, 2 eq, 0.5 M) in NMP were added and the mixture was shaken overnight to yield after preparative HPLC 26 mg (25%) of the title compound 3,8-diazabicyclo[3.2.1]oct-3-yl(1H-1,2,3-triazol-4-yl)methanone.

Example 2

1H-1,2,3-triazol-4-yl[8-{[2-(trifluoromethyl)phenyl]sulfonyl}-3,8-diazabicyclo[3.2.1]oct-3-yl]methanone

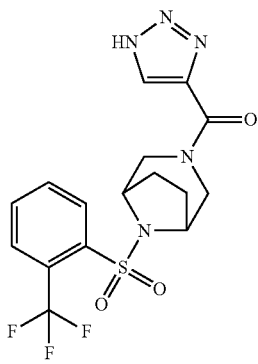 [SMILES: O=C(c1c[nH]nn1)N1CC2CCC(C1)N2S(=O)(=O)c1ccccc1C(F)(F)F]

1.92 g (50% purity, 3.00 mmol) 8-{[2-(trifluoromethyl)phenyl]sulfonyl}-3,8-diazabicyclo[3.2.1]octane (Intermediate 3) were reacted in analogy to example 1, procedure 1.2 with 0.678 g (6 mmol, 2 eq) 1H-1,2,3-triazole-5-carboxylic acid to yield after work-up and purification 792 mg (62%) of the title compound 1H-1,2,3-triazol-4-yl[(8-{[2-(trifluoromethyl)phenyl]sulfonyl}-3,8-diazabicyclo[3.2.1]oct-3-yl]methanone.

LC-MS (Method 1): Rt=0.96 min; MS (ESIpos): m/z=416 [M+H]$^+$ $^1$H-NMR (400 MHz, DMSO-d6) δ[ppm]: 1.602 (2.82), 1.629 (2.52), 1.689 (12.16), 1.980 (0.53), 2.073 (1.54), 2.327 (1.17), 2.669 (1.20), 2.673 (0.87), 2.934 (3.84), 2.964 (4.10), 3.379 (5.16), 4.293 (5.08), 4.355 (9.64), 4.386 (4.07), 4.519 (0.72), 7.890 (1.47), 7.908 (5.87), 7.913 (7.23), 7.920 (16.00), 7.927 (6.81), 7.932 (7.53), 7.936 (7.64), 7.950 (2.37), 7.955 (1.54), 8.018 (0.79), 8.030 (7.57), 8.037 (6.89), 8.053 (5.61), 8.295 (7.27), 8.311 (6.51), 8.317 (6.21), 15.524 (0.53).

Example 3

{8-[(3,5-difluorophenyl)sulfonyl]-3,8-diazabicyclo[3.2.1]oct-3-yl}(1H-1,2,3-triazol-5-yl)methanone

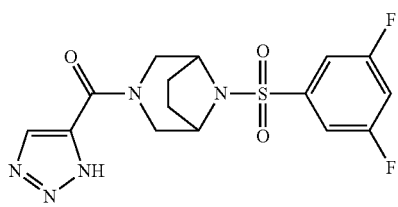 [SMILES: O=C(c1cnn[nH]1)N1CC2CCC(C1)N2S(=O)(=O)c1cc(F)cc(F)c1]

3.46 g (12.00 mmol) 8-[(3,5-difluorophenyl)sulfonyl]-3,8-diazabicyclo[3.2.1]octane (Intermediate 4) were reacted in analogy to example 1, procedure 1.2 with 2.714 g (12 mmol, 2 eq) 1H-1,2,3-triazole-5-carboxylic acid to yield after work-up and purification 1.93 g (42%) of the title compound {8-[(3,5-difluorophenyl)sulfonyl]-3,8-diazabicyclo[3.2.1]oct-3-yl}(1H-1,2,3-triazol-5-yl)methanone.

LC-MS (Method 1): Rt=0.93 min; MS (ESIpos): m/z=384 [M+H]$^+$ $^1$H-NMR (400 MHz, DMSO-d6) δ[ppm]: 1.106 (1.26), 1.153 (0.74), 1.171 (1.48), 1.188 (0.74), 1.317 (4.22), 1.336 (6.93), 1.352 (4.93), 1.384 (1.15), 1.452 (1.67), 1.475 (4.11), 1.496 (2.26), 1.539 (1.26), 1.561 (1.63), 1.619 (1.48), 1.979 (1.26), 1.986 (2.74), 2.322 (1.07), 2.326 (1.48), 2.331 (1.04), 2.518 (6.26), 2.522 (4.19), 2.664 (1.07), 2.668 (1.52), 2.673 (1.07), 2.685 (0.59), 2.692 (1.00), 2.982 (3.59), 3.014 (3.67), 3.282 (0.52), 3.301 (1.00), 3.382 (3.74), 3.412 (3.81), 4.016 (0.63), 4.034 (0.59), 4.345 (6.04), 4.374 (8.00), 4.432 (4.74), 4.739 (1.33), 4.770 (1.26), 7.678 (12.00), 7.694 (15.93), 7.698 (16.00), 7.716 (4.00), 7.722 (3.56), 7.727 (1.59), 8.084 (3.89), 8.541 (4.07), 15.373 (1.67), 15.690 (1.00).

Example 4

{8-[(3-fluorophenyl)sulfonyl]-3,8-diazabicyclo[3.2.1]oct-3-yl}(1H-1,2,3-triazol-5-yl)methanone

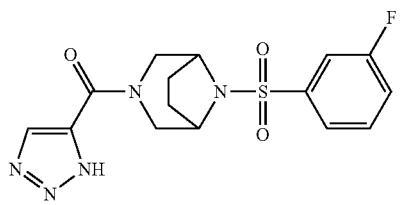 [SMILES: O=C(c1cnn[nH]1)N1CC2CCC(C1)N2S(=O)(=O)c1cccc(F)c1]

3.24 g (12.00 mmol) 8-[(3-fluorophenyl)sulfonyl]-3,8-diazabicyclo[3.2.1]octane (Intermediate 5) were reacted in analogy to example 1, procedure 1.2 with 2.714 g (12 mmol, 2 eq) 1H-1,2,3-triazole-5-carboxylic acid to yield after work-up and purification 1.15 g (26%) of the title compound {8-[(3-fluorophenyl)sulfonyl]-3,8-diazabicyclo[3.2.1]oct-3-yl}(1H-1,2,3-triazol-5-yl)methanone.

LC-MS (Method 1): Rt=0.89 min; MS (ESIpos): m/z=366 [M+H]$^+$ $^1$H-NMR (400 MHz, DMSO-d6) δ[ppm]: 1.154 (1.28), 1.172 (2.67), 1.189 (3.43), 1.205 (2.55), 1.217 (0.78), 1.248 (4.37), 1.269 (6.76), 1.284 (4.95), 1.316 (1.10), 1.419 (1.60), 1.442 (3.75), 1.463 (2.05), 1.532 (2.35), 1.552 (3.45), 1.578 (1.30), 1.987 (4.67), 2.074 (0.74), 2.323 (0.84), 2.327 (1.16), 2.331 (0.86), 2.523 (3.65), 2.665 (0.90), 2.669 (1.20), 2.673 (0.90), 2.686 (2.75), 2.972 (3.99), 3.003 (4.11), 3.376 (4.95), 3.409 (4.43), 4.016 (1.08), 4.034 (1.00), 4.342 (7.38), 4.377 (7.64), 4.524 (1.96), 4.552 (1.84), 7.563 (1.84), 7.568 (2.49), 7.573 (2.29), 7.587 (4.79), 7.591 (5.25), 7.606 (2.93), 7.609 (3.27), 7.612 (3.43), 7.615 (3.09), 7.650 (2.65), 7.666 (3.73), 7.671 (5.97), 7.685 (5.69), 7.692 (3.89), 7.705 (3.25), 7.749 (16.00), 7.752 (13.33), 7.758 (4.71), 7.769 (11.91), 8.307 (5.49).

The following examples were prepared in analogy to Example 1, Procedure 1.1 using 3,8-diazabicyclo[3.2.1]oct-3-yl(1H-1,2,3-triazol-4-yl)methanone (Intermediate 1):

| Example | Structure IUPAC-Name LC-MS | NMR Data |
|---|---|---|
| 5 | {8-[(3-chlorophenyl)sulfonyl]-3,8-diazabicyclo[3.2.1]oct-3-yl}(1H-1,2,3-triazol-4-yl)methanone<br>LC-MS (Method 1): Rt = 0.98 min; MS (ESIpos): m/z = 382 [M + H]⁺ | ¹H-NMR (400 MHz, DMSO-d6) δ [ppm]: 1.237 (4.68), 1.257 (6.72), 1.273 (5.06), 1.306 (1.07), 1.429 (1.44), 1.450 (3.48), 1.463 (2.18), 1.471 (2.09), 1.541 (2.27), 1.563 (3.29), 1.587 (1.30), 1.693 (0.46), 2.074 (7.65), 2.322 (1.95), 2.327 (2.69), 2.331 (1.86), 2.518 (11.08), 2.523 (6.82), 2.539 (2.04), 2.664 (1.95), 2.669 (2.69), 2.674 (1.95), 2.693 (0.74), 2.966 (3.62), 2.998 (3.76), 3.369 (5.38), 3.402 (4.36), 4.344 (7.51), 4.377 (4.87), 4.542 (2.13), 4.573 (2.04), 5.758 (0.60), 7.628 (6.68), 7.649 (15.95), 7.668 (9.97), 7.786 (6.45), 7.788 (7.47), 7.791 (7.23), 7.793 (7.14), 7.806 (5.29), 7.808 (5.29), 7.811 (6.03), 7.814 (5.01), 7.865 (6.31), 7.870 (7.74), 7.872 (6.26), 7.885 (5.24), 7.889 (6.77), 7.892 (5.19), 7.939 (10.30), 7.944 (16.00), 7.949 (8.26), 8.042 (0.46), 8.153 (1.21), 8.294 (8.67). |
| 6 | {8-[(2-methylphenyl)sulfonyl]-3,8-diazabicyclo[3.2.1]oct-3-yl}(1H-1,2,3-triazol-4-yl)methanone<br>LC-MS (Method 1): Rt = 0.95 min; MS (ESIpos): m/z = 362 [M + H]⁺ | ¹H-NMR (400 MHz, DMSO-d6) δ [ppm]: 1.226 (0.70), 1.463 (0.43), 1.586 (0.92), 1.652 (0.45), 1.673 (0.87), 1.714 (1.78), 1.731 (1.23), 2.397 (6.30), 2.518 (1.40), 2.523 (0.86), 2.539 (1.46), 2.614 (0.41), 2.633 (16.00), 2.900 (0.94), 2.933 (0.99), 3.353 (1.88), 3.390 (0.64), 4.176 (1.13), 4.221 (1.14), 4.299 (0.42), 4.337 (1.10), 4.370 (1.04), 4.466 (0.55), 4.497 (0.68), 7.401 (1.30), 7.413 (1.11), 7.421 (1.57), 7.432 (2.04), 7.453 (2.41), 7.474 (2.30), 7.578 (1.43), 7.582 (1.45), 7.597 (2.19), 7.600 (2.10), 7.616 (0.92), 7.619 (0.88), 7.762 (1.92), 7.783 (1.67), 7.934 (2.18), 7.937 (2.13), 7.954 (2.09), 7.957 (1.94), 8.300 (2.03). |

The following examples were prepared in analogy to Example 1, Procedure 1.2 using the given intermediate:

| Example Intermediate | Structure IUPAC-Name LC-MS | NMR Data |
|---|---|---|
| 7<br>Int 6 | {8-[(2-chlorophenyl)sulfonyl]-3,8-diazabicyclo[3.2.1]oct-3-yl}(1H-1,2,3-triazol-4-yl)methanone<br>LC-MS (Method 1): Rt = 0.88 min; MS (ESIpos): m/z = 383 [M + H]⁺ | ¹H-NMR (400 MHz, DMSO-d6) δ [ppm]: 0.850 (0.59), 1.232 (1.37), 1.238 (1.54), 1.261 (0.82), 1.603 (0.66), 1.688 (2.17), 2.083 (16.00), 2.326 (0.41), 2.518 (1.70), 2.522 (1.21), 2.668 (0.42), 2.942 (0.79), 2.972 (0.86), 3.353 (0.84), 3.385 (0.79), 4.305 (1.06), 4.365 (2.21), 4.397 (0.92), 7.557 (1.21), 7.561 (1.27), 7.574 (1.87), 7.577 (1.68), 7.578 (1.97), 7.581 (1.45), 7.593 (1.65), 7.598 (1.78), 7.672 (0.92), 7.677 (0.88), 7.693 (2.48), 7.696 (2.69), 7.710 (2.67), 7.713 (5.88), 7.717 (3.44), 7.733 (1.12), 7.738 (0.62), 8.070 (2.34), 8.073 (2.38), 8.090 (2.05), 8.093 (2.07), 8.132 (1.08). |

-continued

| Example Intermediate | Structure IUPAC-Name LC-MS | NMR Data |
|---|---|---|
| 8 Int 7 | 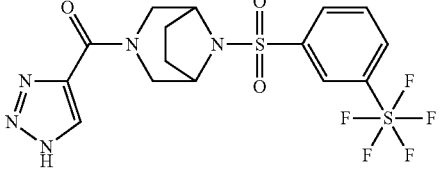<br>[8-{[3-(pentafluoro-lambda⁶-sulfanyl)phenyl]sulfonyl}-3,8-diazabicyclo[3.2.1]oct-3-yl](1H-1,2,3-triazol-4-yl)methanone<br>LC-MS (Method 1): Rt = 1.08 min; MS (ESIpos): m/z = 474 [M + H]⁺ | ¹H-NMR (400 MHz, DMSO-d6) δ [ppm]: 1.190 (1.84), 1.209 (2.91), 1.227 (2.25), 1.258 (0.47), 1.449 (0.63), 1.470 (1.62), 1.494 (0.92), 1.567 (0.92), 1.587 (1.36), 1.974 (0.57), 2.074 (16.00), 2.323 (0.61), 2.327 (0.92), 2.332 (0.68), 2.518 (4.49), 2.523 (3.22), 2.665 (0.65), 2.669 (0.94), 2.673 (0.66), 2.978 (1.63), 3.010 (1.70), 3.378 (1.50), 3.410 (1.50), 4.350 (1.65), 4.383 (1.68), 4.405 (2.02), 4.447 (1.96), 7.877 (1.60), 7.898 (3.30), 7.919 (1.79), 8.134 (0.69), 8.245 (3.64), 8.255 (4.12), 8.260 (7.74), 8.264 (10.21), 8.290 (3.80), 8.292 (3.68), 8.296 (3.09), 8.298 (2.75), 8.311 (3.35), 8.314 (3.20), 8.319 (2.49). |
| 9 Int 8 | 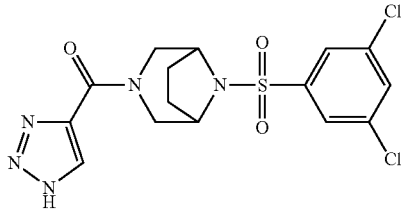 [SMILES: O=C(c1c[nH]nn1)N1CC2CCC(C1)N2S(=O)(=O)c1cc(Cl)cc(Cl)c1]<br>{8-[(3,5-dichlorophenyl)sulfonyl]-3,8-diazabicyclo[3.2.1]oct-3-yl}(1H-1,2,3-triazol-4-yl)methanone<br>LC-MS (Method 1): Rt = 1.08 min; MS (ESIpos): m/z = 416 [M + H]⁺ | ¹H-NMR (400 MHz, DMSO-d6) δ [ppm]: 1.290 (1.08), 1.309 (1.71), 1.326 (1.24), 1.485 (0.95), 1.508 (0.51), 1.582 (0.56), 1.603 (0.79), 1.980 (0.41), 2.075 (9.23), 2.322 (0.44), 2.327 (0.65), 2.332 (0.47), 2.518 (2.54), 2.523 (1.80), 2.665 (0.47), 2.669 (0.66), 2.673 (0.47), 2.979 (0.98), 3.011 (1.00), 3.381 (0.90), 3.412 (0.90), 4.340 (0.94), 4.371 (0.92), 4.413 (1.12), 4.465 (1.12), 7.955 (13.36), 7.959 (16.00), 8.027 (4.22), 8.031 (6.43), 8.306 (3.12). |
| 10 Int 9 | 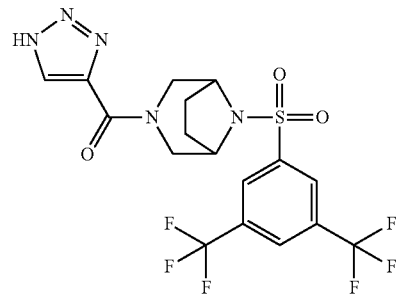 [SMILES: O=C(c1c[nH]nn1)N1CC2CCC(C1)N2S(=O)(=O)c1cc(C(F)(F)F)cc(C(F)(F)F)c1]<br>[8-{[(3,5-bis(trifluoro-methyl)phenyl]sulfonyl}-3,8-diazabicyclo[3.2.1]oct-3-yl](1H-1,2,3-triazol-4-yl)methanone<br>LC-MS (Method 1): Rt = 1.18 min; MS (ESIpos): m/z = 484 [M + H]⁺ | ¹H-NMR (400 MHz, DMSO-d6) δ [ppm]: 1.220 (1.32), 1.238 (2.15), 1.256 (1.44), 1.467 (0.46), 1.488 (1.15), 1.511 (0.63), 1.592 (0.70), 1.614 (1.05), 1.636 (0.40), 2.518 (0.53), 2.992 (1.21), 3.024 (1.25), 3.389 (1.39), 3.420 (1.32), 4.340 (1.13), 4.372 (1.06), 4.526 (1.52), 4.564 (1.82), 8.317 (1.07), 8.540 (16.00). |
| 11 Int 10 | 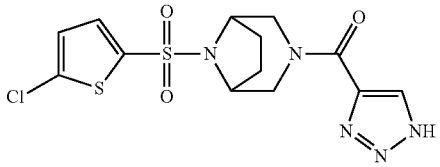 [SMILES: O=C(c1c[nH]nn1)N1CC2CCC(C1)N2S(=O)(=O)c1ccc(Cl)s1]<br>{8-[(5-chlorothiophen-2-yl)sulfonyl]-3,8-diazabicyclo[3.2.1]oct-3-yl}(1H-1,2,3-triazol-4-yl)methanone<br>LC-MS (Method 1): Rt = 0.88 min; MS (ESIpos): m/z = 388 [M + H]⁺ | ¹H-NMR (400 MHz, DMSO-d6) δ [ppm]: 1.232 (0.44), 1.492 (6.67), 1.520 (2.33), 1.575 (0.52), 1.622 (2.01), 2.074 (4.86), 2.327 (0.43), 2.518 (1.79), 2.523 (1.25), 2.669 (0.43), 2.985 (2.56), 3.016 (2.78), 3.389 (2.17), 3.422 (2.24), 4.318 (3.06), 4.376 (5.63), 4.409 (2.51), 4.582 (0.42), 7.328 (16.00), 7.338 (15.97), 7.691 (14.95), 7.702 (14.38). |

| Example Intermediate | Structure IUPAC-Name LC-MS | NMR Data |
|---|---|---|
| 12<br>Int 11 | 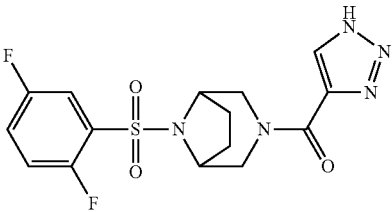 [SMILES: O=C(c1c[nH]nn1)N1CC2CCC(C1)N2S(=O)(=O)c1cc(F)ccc1F]<br>{8-[(2,5-difluorophenyl)sulfonyl]-3,8-diazabicyclo[3.2.1]oct-3-yl}(1H-1,2,3-triazol-4-yl)methanone<br>LC-MS (Method 1): Rt = 0.89 min;<br>MS (ESIpos): m/z = 384 [M + H]⁺ | ¹H-NMR (400 MHz, DMSO-d6) δ [ppm]:<br>0.833 (0.69), 0.851 (1.87), 0.868 (0.59), 1.233 (4.47), 1.469 (6.63), 1.489 (9.77), 1.507 (10.60), 1.558 (6.43), 1.581 (2.94), 1.662 (5.84), 1.986 (1.47), 2.005 (1.28), 2.024 (0.69), 2.323 (2.21), 2.327 (3.14), 2.331 (2.16), 2.518 (11.39), 2.523 (7.90), 2.665 (2.26), 2.669 (3.09), 2.674 (2.16), 2.955 (6.82), 2.985 (6.92), 3.362 (6.72), 3.394 (6.48), 4.356 (8.49), 4.384 (8.29), 4.414 (16.00), 4.561 (1.82), 5.321 (0.79), 5.333 (0.44), 7.552 (4.76), 7.562 (5.06), 7.575 (11.48), 7.585 (11.29), 7.599 (8.74), 7.608 (8.10), 7.633 (3.83), 7.642 (7.75), 7.651 (7.26), 7.662 (8.83), 7.670 (6.43), 7.674 (5.60), 7.683 (11.44), 7.690 (7.41), 7.693 (7.61), 7.696 (8.98), 7.702 (10.50), 7.710 (6.38), 7.715 (7.90), 7.723 (5.15), 8.054 (0.39), 8.316 (2.11), 15.545 (1.62). |
| 13<br>Int 12 | 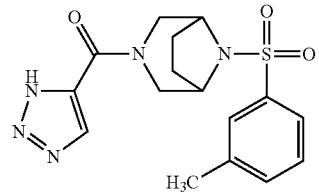 [SMILES: Cc1cccc(S(=O)(=O)N2C3CCC2CN(C(=O)c2cnn[nH]2)C3)c1]<br>{8-[(3-methylphenyl)sulfonyl]-3,8-diazabicyclo[3.2.1]oct-3-yl}(1H-1,2,3-triazol-5-yl)methanone<br>LC-MS (Method 3): R$_t$ = 0.89 min;<br>MS (ESIpos): m/z = 362 [M + H]⁺ | ¹H-NMR (400 MHz, DMSO-d6) δ [ppm]:<br>1.211 (1.02), 1.231 (1.82), 1.247 (1.28), 1.404 (0.96), 1.425 (0.52), 1.494 (0.57), 1.513 (0.81), 1.964 (0.61), 2.073 (1.98), 2.396 (16.00), 2.518 (1.22), 2.522 (0.82), 2.959 (0.96), 2.989 (1.06), 3.362 (1.33), 3.395 (1.01), 4.274 (1.08), 4.330 (2.12), 4.362 (0.93), 7.468 (0.85), 7.487 (2.90), 7.504 (4.50), 7.509 (3.02), 7.525 (0.56), 7.529 (0.67), 7.669 (0.99), 7.672 (1.86), 7.676 (1.23), 7.685 (0.71), 7.690 (1.43), 7.694 (0.98), 7.714 (2.15), 7.718 (2.97). |
| 14<br>Int 13 | 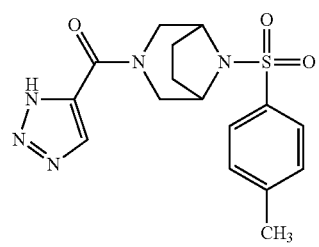 [SMILES: Cc1ccc(S(=O)(=O)N2C3CCC2CN(C(=O)c2cnn[nH]2)C3)cc1]<br>{8-[(4-methylphenyl)sulfonyl]-3,8-diazabicyclo[3.2.1]oct-3-yl}(1H-1,2,3-triazol-5-yl)methanone<br>LC-MS (Method 3): R$_t$ = 0.88 min;<br>MS (ESIpos): m/z = 362 [M + H]⁺ | ¹H-NMR (400 MHz, DMSO-d6) δ [ppm]:<br>1.204 (1.02), 1.222 (1.75), 1.238 (1.24), 1.373 (0.42), 1.399 (0.95), 1.420 (0.52), 1.485 (0.59), 1.502 (0.81), 1.963 (1.05), 2.074 (1.96), 2.397 (16.00), 2.518 (1.22), 2.523 (0.84), 2.952 (1.01), 2.982 (1.03), 3.359 (1.49), 3.391 (1.02), 4.257 (1.10), 4.301 (1.13), 4.329 (1.02), 4.362 (0.91), 7.401 (4.07), 7.421 (4.45), 7.749 (0.41), 7.72 (5.95), 7.766 (2.00), 7.783 (5.21). |
| 15<br>Int 14 | 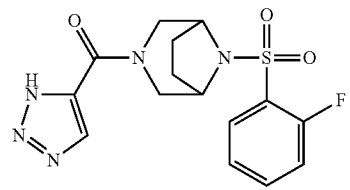 [SMILES: O=C(c1cnn[nH]1)N1CC2CCC(C1)N2S(=O)(=O)c1ccccc1F]<br>{8-[(2-fluorophenyl)sulfonyl]-3,8-diazabicyclo[3.2.1]oct-3-yl}(1H-1,2,3-triazol-5-yl)methanone<br>LC-MS (Method 3): R$_t$ = 0.82 min;<br>MS (ESIpos): m/z = 366 [M + H]⁺ | ¹H-NMR (400 MHz, DMSO-d6) δ [ppm]:<br>1.231 (0.88), 1.416 (5.63), 1.436 (9.87), 1.452 (7.25), 1.467 (2.57), 1.481 (3.45), 1.531 (5.52), 1.553 (2.82), 1.614 (3.34), 1.632 (4.73), 1.977 (4.35), 2.074 (0.44), 2.322 (1.26), 2.326 (1.70), 2.331 (1.18), 2.336 (0.55), 2.518 (6.86), 2.522 (4.51), 2.659 (0.63), 2.664 (1.26), 2.668 (1.81), 2.673 (1.45), 2.949 (5.61), 2.979 (6.13), 3.251 (0.49), 3.357 (6.51), 3.390 (5.55), 3.902 (0.68), 4.313 (6.56), 4.378 (12.88), 4.410 (5.55), 4.550 (1.50), 7.403 (9.14), 7.406 (10.53), 7.422 (15.29), 7.425 (16.00), 7.441 (11.51), 7.444 (11.19), 7.463 (7.19), 7.466 (7.00), 7.484 (9.52), 7.486 (8.78), 7.490 (7.90), 7.493 (7.25), 7.511 (8.45), 7.514 (7.38), 7.739 (4.10), 7.743 (4.54), 7.752 (4.59), 7.756 (6.26), 7.760 (5.88), 7.762 (5.44), 7.764 (5.58), 7.770 (5.28), 7.773 (5.58), 7.774 (5.61), 7.777 (5.85), 7.783 (3.94), 7.791 (3.64), 7.795 (3.45), |

| Example Intermediate | Structure IUPAC-Name LC-MS | NMR Data |
|---|---|---|
| | | 7.867 (7.36), 7.781 (7.11), 7.886 (12.28), 7.890 (11.41), 7.905 (6.62), 7.909 (5.91), 8.308 (1.72), 15.533 (1.18). |
| 16 Int 15 | {8-[(4-fluorophenyl)sulfonyl]-3,8-diazabicyclo[3.2.1]oct-3-yl}(1H-1,2,3-triazol-5-yl)methanone<br>LC-MS (Method 3): R$_t$ = 0.84 min; MS (ESIpos): m/z = 366 [M + H]$^+$ | $^1$H-NMR (400 MHz, DMSO-d6) δ [ppm]: 1.228 (2.98), 1.247 (4.48), 1.263 (3.30), 1.281 (0.72), 1.296 (0.66), 1.411 (1.02), 1.434 (2.49), 1.455 (1.38), 1.522 (1.37), 1.541 (1.95), 1.564 (0.76), 1.970 (2.03), 2.074 (6.02), 2.322 (0.64), 2.326 (0.86), 2.331 (0.59), 2.518 (3.54), 2.522 (2.37), 2.664 (0.64), 2.668 (0.88), 2.673 (0.59), 2.966 (2.36), 2.994 (2.49), 3.369 (2.19), 3.402 (2.19), 4.288 (2.75), 4.339 (5.75), 4.370 (2.46), 4.529 (0.52), 7.424 (1.17), 7.432 (7.92), 7.438 (2.71), 7.449 (3.40), 7.454 (16.00), 7.459 (3.06), 7.471 (2.78), 7.476 (8.63), 7.485 (0.88), 7.949 (1.13), 7.957 (8.22), 7.962 (3.81), 7.970 (9.09), 7.975 (4.36), 7.980 (9.17), 7.987 (3.32), 7.992 (7.75), 8.000 (0.76), 8.309 (0.54), 15.529 (0.49). |
| 17 Int 16 | 3-{[3-(1H-1,2,3-triazol-5-ylcarbonyl)-3,8-diazabicyclo[3.2.1]oct-8-yl]sulfonyl}benzonitrile<br>LC-MS (Method 3): R$_t$ = 0.78 min; MS (ESIpos): m/z = 373 [M + H]$^+$ | $^1$H-NMR (400 MHz, DMSO-d6) δ [ppm]: 1.203 (0.53), 1.235 (3.02), 1.251 (4.12), 1.272 (2.87), 1.303 (0.63), 1.389 (0.44), 1.434 (0.89), 1.455 (2.20), 1.478 (1.22), 1.548 (1.33), 1.571 (1.86), 1.976 (1.59), 2.074 (16.00), 2.323 (0.52), 2.327 (0.73), 2.331 (0.50), 2.518 (3.20), 2.523 (2.15), 2.665 (0.55), 2.669 (0.74), 2.673 (0.53), 2.984 (2.25), 3.016 (2.33), 3.387 (2.13), 3.419 (2.14), 4.341 (2.38), 4.370 (4.44), 4.420 (2.57), 4.546 (0.59), 7.800 (4.00), 7.813 (0.77), 7.821 (8.61), 7.832 (0.55), 7.840 (4.82), 8.134 (0.78), 8.174 (3.83), 8.177 (5.89), 8.180 (4.75), 8.193 (3.95), 8.197 (5.19), 8.200 (4.10), 8.209 (4.24), 8.212 (4.44), 8.214 (4.75), 8.217 (3.93), 8.229 (3.90), 8.232 (3.84), 8.234 (4.37), 8.237 (3.30), 8.315 (0.74), 8.418 (6.16), 8.422 (9.48), 8.425 (5.35). |
| 18 Int 17 | {8-[(3,5-dimethylphenyl)sulfonyl]-3,8-diazabicyclo[3.2.1]oct-3-yl}(1H-1,2,3-triazol-5-yl)methanone<br>LC-MS (Method 3): R$_t$ = 0.97 min; MS (ESIpos): m/z = 376 [M + H]$^+$ | $^1$H-NMR (400 MHz, DMSO-d6) δ [ppm]: 1.232 (0.63), 1.252 (0.93), 1.269 (0.68), 1.405 (0.52), 1.518 (0.47), 2.074 (7.89), 2.350 (16.00), 2.518 (0.55), 2.957 (0.54), 2.987 (0.56), 3.333 (0.42), 3.359 (0.64), 3.391 (0.56), 4.265 (0.59), 4.323 (0.91), 4.356 (0.48), 7.329 (1.72), 7.503 (3.49), 7.505 (3.63), 7.507 (3.35). |
| 19 Int 18 | {8-[(2,5-dimethylphenyl)sulfonyl]-3,8-diazabicyclo[3.2.1]oct-3-yl}(1H-1,2,3-triazol-5-yl)methanone<br>LC-MS (Method 3): R$_t$ = 0.97 min; MS (ESIpos): m/z = 376 [M + H]$^+$ | $^1$H-NMR (400 MHz, DMSO-d6) δ [ppm]: 1.142 (0.79), 1.158 (0.79), 1.580 (1.03), 1.604 (0.56), 1.650 (0.49), 1.671 (0.98), 1.712 (1.93), 1.734 (1.37), 2.322 (0.40), 2.326 (0.54), 2.331 (0.50), 2.356 (15.66), 2.518 (1.64), 2.522 (1.12), 2.557 (0.67), 2.575 (16.00), 2.668 (0.43), 2.886 (1.07), 2.917 (1.11), 3.307 (1.44), 4.174 (1.32), 4.211 (1.30), 4.333 (0.98), 4.364 (0.95), 4.465 (0.59), 4.496 (0.56), 7.330 (2.18), 7.350 (3.92), 7.393 (2.38), 7.395 (2.33), 7.412 (1.30), 7.415 (1.26), 7.752 (3.55), 7.755 (3.39), 8.296 (2.10). |

| Example Intermediate | Structure IUPAC-Name LC-MS | NMR Data |
| --- | --- | --- |
| 20 Int 19 | {8-[(3-methoxyphenyl)sulfonyl]-3,8-diazabicyclo[3.2.1]oct-3-yl}(1H-1,2,3-triazol-5-yl)methanone<br>LC-MS (Method 3): $R_t$ = 0.84 min;<br>MS (ESIpos): m/z = 378 [M + H]$^+$ | $^1$H-NMR (400 MHz, DMSO-d6) δ [ppm]: 0.852 (0.44), 1.158 (1.64), 1.174 (1.64), 1.237 (6.74), 1.256 (9.43), 1.272 (6.45), 1.305 (1.46), 1.390 (2.10), 1.413 (4.70), 1.434 (2.69), 1.503 (3.12), 1.521 (4.41), 1.546 (1.66), 1.968 (2.60), 2.074 (16.00), 2.327 (1.66), 2.669 (1.72), 2.962 (4.41), 2.991 (4.64), 3.334 (5.43), 3.365 (6.95), 3.397 (5.75), 3.655 (0.64), 4.018 (0.47), 4.311 (6.07), 4.339 (6.80), 4.366 (9.96), 4.514 (2.57), 4.544 (2.45), 7.257 (6.07), 7.263 (6.45), 7.277 (6.77), 7.281 (7.50), 7.352 (13.23), 7.357 (9.87), 7.446 (6.86), 7.466 (11.15), 7.510 (9.87), 7.530 (12.96), 7.550 (5.17), 8.035 (0.41), 8.144 (1.11), 8.299 (7.47), 15.425 (0.47). |
| 21 Int 20 | {8-[(4-methoxyphenyl)sulfonyl]-3,8-diazabicyclo[3.2.1]oct-3-yl}(1H-1,2,3-triazol-5-yl)methanone<br>LC-MS (Method 3): $R_t$ = 0.82 min;<br>MS (ESIpos): m/z = 378 [M + H]$^+$ | $^1$H-NMR (400 MHz, DMSO-d6) δ [ppm]: 1.139 (1.54), 1.156 (1.61), 1.209 (2.16), 1.228 (3.78), 1.244 (2.56), 1.275 (0.56), 1.379 (0.86), 1.403 (1.94), 1.424 (1.07), 1.455 (0.41), 1.489 (1.25), 1.507 (1.84), 1.532 (0.68), 1.964 (1.26), 2.074 (1.53), 2.322 (0.52), 2.326 (0.74), 2.331 (0.51), 2.518 (2.92), 2.522 (1.96), 2.664 (0.55), 2.668 (0.74), 2.673 (0.53), 2.948 (2.05), 2.979 (2.12), 3.355 (2.79), 3.387 (2.50), 3.823 (1.50), 4.238 (2.27), 4.282 (2.29), 4.328 (1.90), 4.360 (1.79), 4.496 (1.16), 4.528 (1.08), 7.095 (1.84), 7.102 (14.27), 7.108 (4.04), 7.120 (4.38), 7.125 (15.44), 7.132 (1.43), 7.788 (0.81), 7.792 (1.82), 7.800 (16.00), 7.805 (4.27), 7.810 (1.12), 7.817 (4.41), 7.822 (14.12), 7.830 (1.30), 8.292 (4.44). |
| 22 Int 21 | {8-[(4-chlorophenyl)sulfonyl]-3,8-diazabicyclo[3.2.1]oct-3-yl}(1H-1,2,3-triazol-5-yl)methanone<br>LC-MS (Method 3): $R_t$ = 0.93 min;<br>MS (ESIpos): m/z = 382 [M + H]$^+$ | $^1$H-NMR (400 MHz, DMSO-d6) δ [ppm]: 1.246 (2.01), 1.265 (3.06), 1.282 (2.27), 1.314 (0.47), 1.420 (0.72), 1.443 (1.71), 1.465 (0.95), 1.531 (0.95), 1.550 (1.36), 1.971 (1.42), 2.074 (3.53), 2.322 (0.54), 2.326 (0.76), 2.331 (0.53), 2.518 (2.88), 2.522 (1.95), 2.664 (0.57), 2.668 (0.72), 2.673 (0.53), 2.965 (1.64), 2.994 (1.70), 3.369 (1.51), 3.401 (1.50), 4.295 (1.95), 4.342 (4.14), 4.372 (1.75), 7.671 (1.93), 7.677 (12.56), 7.682 (3.62), 7.694 (4.82), 7.699 (16.00), 7.705 (1.68), 7.894 (1.10), 7.898 (2.17), 7.904 (15.64), 7.909 (4.34), 7.915 (1.11), 7.922 (3.92), 7.927 (12.07), 7.933 (1.28). |

-continued

| Example Intermediate | Structure IUPAC-Name LC-MS | NMR Data |
|---|---|---|
| 23 Int 22 | {8-[(3,4-difluorophenyl)sulfonyl]-3,8-diazabicyclo[3.2.1]oct-3-yl}(1H-1,2,3-triazol-5-yl)methanone<br>LC-MS (Method 3): R$_t$ = 0.89 min;<br>MS (ESIpos): m/z = 384 [M + H]$^+$ | $^1$H-NMR (400 MHz, DMSO-d6) δ [ppm]: 1.241 (0.53), 1.267 (0.85), 1.294 (3.22), 1.315 (4.82), 1.330 (3.56), 1.361 (0.83), 1.437 (1.14), 1.458 (2.75), 1.481 (1.45), 1.551 (1.65), 1.571 (2.32), 1.594 (0.86), 1.978 (1.95), 2.074 (16.00), 2.323 (0.86), 2.327 (1.20), 2.331 (0.85), 2.518 (4.64), 2.523 (3.18), 2.665 (0.86), 2.669 (1.18), 2.674 (0.83), 2.977 (2.87), 3.007 (2.87), 3.380 (2.67), 3.412 (2.65), 4.341 (5.31), 4.377 (4.86), 4.542 (0.77), 7.668 (1.85), 7.690 (3.42), 7.693 (2.56), 7.709 (3.54), 7.715 (3.36), 7.735 (2.95), 7.784 (2.87), 7.789 (3.18), 7.792 (2.79), 7.795 (2.79), 7.798 (2.48), 7.806 (1.99), 7.809 (2.02), 7.816 (1.61), 7.819 (1.32), 8.038 (2.52), 8.044 (2.85), 8.057 (2.97), 8.063 (4.58), 8.069 (2.65), 8.082 (2.63), 8.087 (2.42), 8.135 (1.02), 8.320 (1.00), 15.535 (0.43). |
| 24 Int 23 | {8-[(2,6-difluorophenyl)sulfonyl]-3,8-diazabicyclo[3.2.1]oct-3-yl}(1H-1,2,3-triazol-5-yl)methanone<br>LC-MS (Method 3): R$_t$ = 0.82 min;<br>MS (ESIpos): m/z = 384 [M + H]$^+$ | $^1$H-NMR (400 MHz, DMSO-d6) δ [ppm]: 1.232 (0.63), 1.445 (1.09), 1.472 (4.23), 1.492 (6.66), 1.508 (5.24), 1.522 (2.73), 1.576 (3.93), 1.597 (1.94), 1.678 (3.17), 1.983 (2.89), 2.074 (0.96), 2.322 (1.23), 2.326 (1.69), 2.331 (1.17), 2.518 (6.28), 2.522 (4.31), 2.664 (1.26), 2.668 (1.69), 2.673 (1.20), 2.959 (3.93), 2.988 (4.01), 3.365 (3.69), 3.397 (3.52), 4.374 (4.94), 4.402 (5.00), 4.433 (9.50), 4.561 (0.85), 7.322 (10.62), 7.344 (16.00), 7.367 (12.10), 7.747 (2.16), 7.762 (5.35), 7.768 (4.10), 7.777 (2.92), 7.783 (8.44), 7.789 (2.87), 7.799 (4.01), 7.804 (4.61), 7.819 (2.02), 8.055 (0.41), 8.133 (1.06), 8.315 (0.74), 15.546 (0.71). |
| 25 Int 24 | {8-[(2,4-difluorophenyl)sulfonyl]-3,8-diazabicyclo[3.2.1]oct-3-yl}(1H-1,2,3-triazol-5-yl)methanone<br>LC-MS (Method 3): R$_t$ = 0.87 min;<br>MS (ESIpos): m/z = 384 [M + H]$^+$ | $^1$H-NMR (400 MHz, DMSO-d6) δ [ppm]: 0.850 (0.59), 1.208 (1.00), 1.225 (1.59), 1.232 (1.48), 1.425 (1.95), 1.452 (8.09), 1.472 (12.93), 1.489 (11.39), 1.501 (6.61), 1.550 (7.91), 1.571 (3.90), 1.594 (1.89), 1.651 (7.56), 1.981 (5.43), 2.075 (9.86), 2.323 (2.48), 2.327 (3.54), 2.332 (2.48), 2.336 (1.06), 2.518 (12.04), 2.523 (9.21), 2.665 (2.60), 2.669 (3.84), 2.673 (2.72), 2.947 (8.56), 2.977 (9.09), 3.248 (0.83), 3.331 (16.00), 3.354 (10.92), 3.387 (8.86), 3.563 (0.47), 4.304 (9.86), 4.375 (15.47), 4.409 (7.85), 4.530 (2.89), 7.302 (6.55), 7.306 (6.79), 7.309 (6.85), 7.322 (13.17), 7.329 (13.52), 7.344 (6.97), 7.349 (7.08), 7.351 (6.79), 7.582 (8.56), 7.587 (9.03), 7.604 (10.51), 7.610 (12.87), 7.615 (10.21), 7.631 (8.80), 7.637 (8.68), 7.931 (8.50), 7.946 (9.74), 7.952 (15.11), 7.968 (15.00), 7.974 (9.15), 7.989 (8.09), 8.051 (1.06), 8.136 (0.53), 8.313 (5.43), 15.539 (1.65). |
| 26 Int 25 | {8-[(3-chloro-2-methylphenyl)sulfonyl]-3,8-diazabicyclo[3.2.1]oct-3-yl}(1H-1,2,3-triazol-5-yl)methanone<br>LC-MS (Method 3): R$_t$ = 1.02 min;<br>MS (ESIpos): m/z = 396 [M + H]$^+$ | $^1$H-NMR (400 MHz, DMSO-d6) δ [ppm]: 1.624 (0.77), 1.643 (0.52), 1.687 (0.43), 1.710 (0.72), 1.760 (0.51), 1.789 (0.99), 1.804 (1.40), 1.975 (0.63), 2.075 (2.60), 2.518 (1.36), 2.523 (1.06), 2.647 (0.60), 2.654 (0.43), 2.674 (16.00), 2.916 (0.82), 2.948 (0.86), 3.366 (0.81), 4.190 (0.96), 4.240 (0.95), 4.339 (0.79), 4.371 (0.77), 7.450 (1.25), 7.470 (2.72), 7.490 (1.47), 7.805 (2.09), 7.808 (2.14), 7.825 (1.90), 7.827 (1.81), 7.964 (2.13), 7.967 (2.07), 7.984 (1.97), 7.987 (1.82). |

| Example Intermediate | Structure IUPAC-Name LC-MS | NMR Data |
|---|---|---|
| 27 Int 26 | {8-[(3-chloro-2-fluorophenyl)sulfonyl]-3,8-diazabicyclo[3.2.1]oct-3-yl}(1H-1,2,3-triazol-5-yl)methanone<br>LC-MS (Method 3): $R_t$ = 0.94 min; MS (ESIpos): m/z = 398 [M − H]⁻ | ¹H-NMR (400 MHz, DMSO-d6) δ [ppm]: 1.183 (2.18), 1.199 (2.26), 1.232 (0.78), 1.426 (1.52), 1.452 (5.02), 1.470 (8.37), 1.485 (5.96), 1.517 (2.80), 1.568 (4.75), 1.591 (2.53), 1.651 (3.04), 1.670 (4.48), 1.983 (4.79), 2.075 (3.04), 2.318 (0.74), 2.323 (1.60), 2.327 (2.37), 2.332 (1.64), 2.336 (0.70), 2.518 (7.51), 2.523 (5.96), 2.660 (0.78), 2.665 (1.67), 2.669 (2.41), 2.673 (1.79), 2.678 (0.86), 2.959 (4.48), 2.989 (4.71), 3.230 (0.51), 3.263 (0.97), 3.368 (6.35), 3.400 (5.53), 4.338 (5.80), 4.388 (8.99), 4.413 (7.20), 4.539 (2.26), 4.568 (2.10), 7.435 (7.44), 7.437 (7.44), 7.455 (15.57), 7.457 (16.00), 7.475 (8.88), 7.478 (8.72), 7.834 (0.82), 7.844 (6.31), 7.848 (7.86), 7.855 (2.06), 7.860 (7.28), 7.863 (12.34), 7.868 (6.77), 7.880 (6.23), 7.884 (6.19), 7.950 (7.40), 7.954 (7.32), 7.967 (8.60), 7.971 (11.64), 7.974 (7.24), 7.988 (7.28), 7.991 (6.00), 8.053 (1.05), 8.140 (1.83), 8.314 (5.64), 15.463 (0.55). |
| 28 Int 27 | {8-[(3-chloro-4-fluorophenyl)sulfonyl]-3,8-diazabicyclo[3.2.1]oct-3-yl}(1H-1,2,3-triazol-5-yl)methanone<br>LC-MS (Method 3): $R_t$ = 0.96 min; MS (ESIpos): m/z = 400 [M + H]⁺ | ¹H-NMR (400 MHz, DMSO-d6) δ [ppm]: 1.232 (1.29), 1.278 (4.18), 1.298 (6.56), 1.315 (4.88), 1.345 (1.09), 1.442 (1.48), 1.464 (3.67), 1.486 (1.95), 1.556 (2.15), 1.579 (3.08), 1.977 (1.95), 2.075 (4.72), 2.323 (1.52), 2.327 (2.22), 2.332 (1.60), 2.450 (0.43), 2.455 (0.43), 2.460 (0.43), 2.465 (0.51), 2.469 (0.82), 2.518 (9.01), 2.523 (6.52), 2.665 (1.60), 2.669 (2.30), 2.673 (1.64), 2.976 (3.71), 3.007 (3.82), 3.378 (3.63), 3.410 (3.51), 4.343 (6.28), 4.367 (4.76), 4.408 (4.25), 4.547 (1.01), 7.648 (8.08), 7.660 (0.82), 7.670 (16.00), 7.693 (9.33), 7.927 (4.49), 7.933 (5.23), 7.938 (5.27), 7.944 (5.15), 7.949 (4.84), 7.955 (5.23), 7.960 (4.33), 7.966 (4.57), 8.149 (9.09), 8.155 (8.94), 8.166 (9.01), 8.172 (8.55), 8.312 (1.33), 15.548 (0.86). |
| 29 Int 28 | 1H-1,2,3-triazol-5-yl[8-{[3-(trifluoromethyl)phenyl]sulfonyl}-3,8-diazabicyclo[3.2.1]oct-3-yl]methanone<br>LC-MS (Method 3): $R_t$ = 0.98 min; MS (ESIpos): m/z = 416 [M + H]⁺ | ¹H-NMR (400 MHz, DMSO-d6) δ [ppm]: 1.160 (0.71), 1.190 (4.10), 1.209 (6.50), 1.227 (5.17), 1.258 (1.02), 1.430 (1.40), 1.452 (3.57), 1.475 (2.00), 1.547 (2.14), 1.568 (3.07), 1.591 (1.19), 1.972 (2.57), 2.074 (16.00), 2.323 (0.93), 2.327 (1.36), 2.332 (0.98), 2.518 (5.12), 2.523 (3.76), 2.665 (0.98), 2.669 (1.38), 2.673 (1.02), 2.977 (3.64), 3.009 (3.79), 3.378 (3.57), 3.411 (3.52), 4.343 (3.57), 4.380 (5.60), 4.439 (4.21), 4.551 (1.02), 7.858 (4.26), 7.878 (9.43), 7.898 (5.38), 8.107 (6.95), 8.109 (6.52), 8.127 (5.90), 8.129 (5.64), 8.135 (1.93), 8.176 (11.55), 8.235 (6.88), 8.255 (6.21), 8.312 (1.48), 15.535 (0.67). |
| 30 Int 29 | {8-[(2,5-dichlorophenyl)sulfonyl]-3,8-diazabicyclo[3.2.1]oct-3-yl}(1H-1,2,3-triazol-5-yl)methanone<br>LC-MS (Method 3): $R_t$ = 1.01 min; MS (ESIpos): m/z = 417 [M + H]⁺ | ¹H-NMR (400 MHz, DMSO-d6) δ [ppm]: 1.625 (1.41), 1.642 (1.09), 1.720 (6.67), 1.985 (1.48), 2.075 (1.38), 2.323 (0.54), 2.327 (0.79), 2.332 (0.54), 2.518 (2.73), 2.523 (2.02), 2.665 (0.56), 2.669 (0.83), 2.673 (0.65), 2.941 (1.96), 2.973 (2.03), 3.330 (6.60), 3.352 (2.10), 3.385 (1.84), 4.364 (4.33), 4.398 (2.42), 4.421 (2.49), 4.525 (0.51), 7.753 (4.52), 7.765 (0.74), 7.768 (0.82), 7.775 (16.00), 7.781 (0.83), 7.788 (13.35), 7.794 (11.03), 7.810 (3.16), 7.815 (4.37), 8.025 (0.90), 8.031 (10.47), 8.038 (9.75), 8.321 (0.62), 15.535 (0.46). |

| Example Intermediate | Structure IUPAC-Name LC-MS | NMR Data |
|---|---|---|
| 31<br>Int 30 | 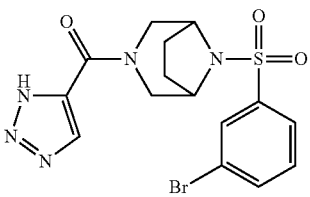 [SMILES: O=C(c1cnn[nH]1)N1CC2CCC(C1)N2S(=O)(=O)c1cccc(Br)c1]<br>{8-[(3-bromophenyl)sulfonyl]-3,8-diazabicyclo[3.2.1]oct-3-yl}(1H-1,2,3-triazol-5-yl)methanone<br>LC-MS (Method 1): Rt = 1.07 min; MS (ESIpos): m/z = 426 [M + H]⁺ | $^1$H-NMR (400 MHz, DMSO-d6) δ [ppm]: 0.884 (0.78), 0.901 (0.81), 0.931 (0.78), 0.947 (0.75), 1.065 (0.75), 1.082 (0.78), 1.165 (0.84), 1.178 (1.50), 1.194 (1.47), 1.233 (4.99), 1.252 (6.52), 1.270 (4.76), 1.302 (1.10), 1.428 (1.38), 1.451 (3.43), 1.472 (1.96), 1.541 (2.10), 1.563 (3.08), 1.586 (1.18), 1.972 (1.85), 2.074 (6.08), 2.323 (1.12), 2.327 (1.64), 2.332 (1.21), 2.518 (7.09), 2.523 (4.87), 2.665 (1.18), 2.669 (1.70), 2.673 (1.21), 2.967 (3.55), 2.997 (3.66), 3.371 (4.21), 3.403 (3.81), 3.488 (0.40), 4.343 (7.18), 4.376 (4.61), 4.530 (1.47), 7.557 (7.18), 7.577 (16.00), 7.596 (9.08), 7.678 (0.46), 7.906 (7.73), 7.911 (7.78), 7.916 (7.64), 7.918 (6.69), 7.920 (8.33), 7.924 (8.45), 7.926 (6.80), 7.928 (6.49), 7.931 (6.31), 7.936 (6.23), 7.938 (5.56), 7.941 (6.98), 7.943 (4.87), 8.052 (9.69), 8.056 (15.83), 8.060 (8.16), 8.140 (0.43), 8.307 (3.66), 15.519 (0.52). |
| 32<br>Int 31 | 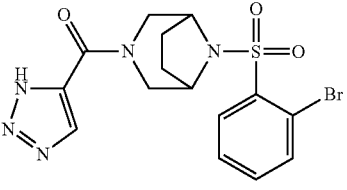 [SMILES: O=C(c1cnn[nH]1)N1CC2CCC(C1)N2S(=O)(=O)c1ccccc1Br]<br>{8-[(2-bromophenyl)sulfonyl]-3,8-diazabicyclo[3.2.1]oct-3-yl}(1H-1,2,3-triazol-5-yl)methanone<br>LC-MS (Method 3): R$_t$ = 0.90 min; MS (ESIpos): m/z = 427 [M + H]⁺ | $^1$H-NMR (400 MHz, DMSO-d6) δ [ppm]: 1.232 (0.53), 1.620 (2.72), 1.644 (1.64), 1.703 (3.09), 1.730 (7.39), 1.754 (2.60), 1.983 (2.19), 2.075 (4.93), 2.323 (0.81), 2.327 (1.16), 2.332 (0.83), 2.518 (4.22), 2.523 (3.19), 2.665 (0.85), 2.669 (1.20), 2.673 (0.85), 2.976 (2.84), 3.007 (3.05), 3.392 (3.09), 3.425 (3.01), 4.284 (3.55), 4.355 (5.28), 4.389 (2.66), 4.487 (1.22), 4.515 (1.16), 7.567 (2.33), 7.572 (3.37), 7.586 (8.20), 7.591 (8.69), 7.597 (1.12), 7.604 (14.44), 7.610 (16.00), 7.623 (8.99), 7.628 (8.16), 7.642 (3.43), 7.646 (2.66), 7.890 (0.73), 7.896 (9.58), 7.900 (11.17), 7.908 (0.79), 7.913 (5.81), 7.915 (5.81), 7.919 (8.12), 8.096 (0.53), 8.107 (8.69), 8.112 (6.25), 8.114 (6.40), 8.120 (0.75), 8.126 (9.10), 8.131 (7.90), 8.140 (0.49), 8.314 (3.05). |
| 33<br>Int 32 | 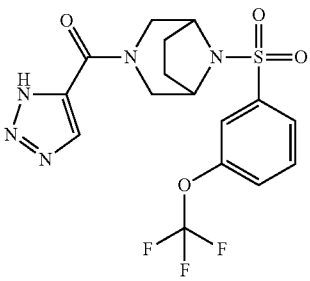 [SMILES: O=C(c1cnn[nH]1)N1CC2CCC(C1)N2S(=O)(=O)c1cccc(OC(F)(F)F)c1]<br>1H-1,2,3-triazol-5-yl[8-{[3-(trifluoromethoxy)phenyl]sulfonyl}-3,8-diazabicyclo[3.2.1]oct-3-yl]methanone<br>LC-MS (Method 3): R$_t$ = 1.01 min; MS (ESIpos): m/z = 432 [M + H]⁺ | $^1$H-NMR (400 MHz, DMSO-d6) δ [ppm]: 0.851 (0.43), 1.176 (0.79), 1.206 (3.76), 1.227 (6.47), 1.242 (4.88), 1.274 (1.12), 1.423 (1.23), 1.447 (3.11), 1.470 (1.84), 1.541 (1.91), 1.562 (2.82), 1.584 (1.08), 2.075 (4.05), 2.323 (1.44), 2.327 (2.09), 2.332 (1.41), 2.518 (7.37), 2.523 (5.60), 2.665 (1.52), 2.669 (2.13), 2.673 (1.48), 2.678 (0.65), 2.973 (3.25), 3.005 (3.32), 3.375 (3.83), 3.407 (3.43), 4.347 (6.18), 4.378 (3.86), 4.406 (3.68), 4.535 (1.23), 7.765 (16.00), 7.770 (5.74), 7.772 (5.13), 7.780 (10.47), 7.799 (2.56), 7.874 (9.86), 7.944 (0.69), 7.954 (5.60), 7.958 (7.48), 7.965 (3.72), 7.970 (5.06), 7.974 (4.55), 7.976 (4.73), 7.980 (4.01), 8.038 (0.76), 8.139 (0.43), 8.307 (2.71), 15.529 (0.51). |

| Example Intermediate | Structure IUPAC-Name LC-MS | NMR Data |
|---|---|---|
| 34 Int 33 | [8-{[5-chloro-2-(trifluoromethyl)phenyl]sulfonyl}-3,8-diazabicyclo[3.2.1]oct-3-yl](1H-1,2,3-triazol-5-yl)methanone<br>LC-MS (Method 3): $R_t$ = 1.05 min;<br>MS (ESIpos): m/z = 450 [M + H]$^+$ | $^1$H-NMR (400 MHz, DMSO-d6) δ [ppm]: 1.130 (3.10), 1.147 (3.21), 1.622 (2.14), 1.650 (2.03), 1.710 (10.01), 1.983 (2.20), 2.323 (0.77), 2.327 (1.13), 2.332 (0.81), 2.518 (3.94), 2.523 (2.80), 2.665 (0.83), 2.669 (1.26), 2.673 (0.94), 2.910 (3.02), 2.943 (3.10), 3.239 (0.49), 3.354 (3.94), 4.358 (5.67), 4.385 (3.74), 4.422 (3.76), 4.516 (1.90), 4.546 (1.78), 7.995 (3.40), 7.999 (3.31), 8.017 (6.85), 8.020 (7.14), 8.054 (16.00), 8.076 (7.46), 8.256 (11.08), 8.261 (10.74), 8.311 (8.19). |
| 35 Int 34 | 2-{[3-(1H-1,2,3-triazol-5-ylcarbonyl)-3,8-diazabicyclo[3.2.1]oct-8-yl]sulfonyl}benzonitrile<br>LC-MS (Method 1): $R_t$ = 0.82 min;<br>MS (ESIpos): m/z = 373 [M + H]$^+$ | $^1$H-NMR (400 MHz, DMSO-d6) δ [ppm]: 1.005 (0.44), 1.169 (0.64), 1.184 (0.88), 1.201 (0.81), 1.238 (2.92), 1.254 (1.49), 1.268 (1.12), 1.345 (2.44), 1.348 (2.44), 1.424 (0.47), 1.593 (14.27), 1.680 (2.17), 1.703 (3.29), 1.985 (3.32), 2.074 (13.69), 2.322 (1.49), 2.326 (2.10), 2.332 (1.46), 2.336 (0.68), 2.518 (6.88), 2.522 (4.81), 2.535 (0.75), 2.539 (1.53), 2.664 (1.53), 2.668 (2.00), 2.673 (1.49), 2.685 (0.61), 2.692 (1.59), 2.807 (0.41), 2.837 (0.41), 3.000 (4.00), 3.030 (4.03), 3.265 (0.41), 3.282 (0.51), 3.300 (1.12), 3.318 (0.54), 3.328 (0.64), 3.413 (4.51), 3.445 (4.68), 3.578 (0.78), 3.606 (0.81), 3.694 (0.71), 3.724 (0.75), 4.015 (0.68), 4.052 (0.61), 4.155 (0.41), 4.192 (0.44), 4.275 (0.92), 4.323 (5.66), 4.375 (9.36), 4.402 (4.98), 4.542 (0.98), 7.884 (5.15), 7.888 (5.39), 7.903 (13.25), 7.906 (13.66), 7.922 (13.12), 7.925 (11.97), 7.932 (10.61), 7.936 (11.46), 7.943 (1.46), 7.947 (2.71), 7.951 (13.08), 7.956 (14.37), 7.966 (1.15), 7.971 (6.51), 7.975 (5.42), 8.052 (1.53), 8.132 (0.78), 8.148 (1.73), 8.150 (1.90), 8.157 (13.90), 8.159 (13.12), 8.161 (11.80), 8.167 (14.07), 8.171 (16.00), 8.176 (14.03), 8.179 (11.66), 8.184 (10.88), 8.189 (11.53), 8.320 (0.61). |
| 36 Int 35 | 1H-1,2,3-triazol-5-yl[8-{[4-(trifluoromethyl)phenyl]sulfonyl}-3,8-diazabicyclo[3.2.1]oct-3-yl]methanone<br>LC-MS (Method 1): $R_t$ = 1.04 min;<br>MS (ESIpos): m/z = 416 [M + H]$^+$ | 1H-NMR (400 MHz, DMSO-d6) δ [ppm]: 1.239 (1.00), 1.256 (2.51), 1.273 (3.57), 1.289 (2.61), 1.440 (0.85), 1.464 (2.07), 1.485 (1.23), 1.546 (0.79), 1.974 (1.43), 2.074 (16.00), 2.322 (0.60), 2.326 (0.80), 2.332 (0.57), 2.518 (2.64), 2.523 (1.84), 2.664 (0.60), 2.669 (0.83), 2.673 (0.60), 2.980 (1.98), 3.011 (1.98), 3.382 (1.91), 3.413 (1.79), 4.353 (3.63), 4.387 (3.81), 4.737 (0.43), 7.987 (8.02), 8.008 (10.70), 8.043 (0.52), 8.080 (1.13), 8.124 (7.69), 8.145 (5.57), 8.535 (0.82), 15.366 (0.65). |

| Example Intermediate | Structure IUPAC-Name LC-MS | NMR Data |
|---|---|---|
| 37 Int 36 | 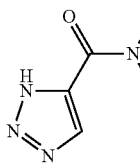 {8-[(4-hydroxyphenyl)sulfonyl]-3,8-diazabicyclo[3.2.1]oct-3-yl}(1H-1,2,3-triazol-5-yl)methanone LC-MS (Method 1): $R_t$ = 0.70 min; MS (ESIpos): m/z = 364 [M + H]$^+$ | $^1$H-NMR (400 MHz, DMSO-d6) δ [ppm]: 1.213 (2.75), 1.231 (5.23), 1.250 (3.61), 1.268 (1.28), 1.281 (0.72), 1.371 (1.08), 1.394 (2.58), 1.415 (1.42), 1.495 (1.58), 2.074 (3.20), 2.174 (0.43), 2.323 (0.67), 2.327 (0.95), 2.331 (0.70), 2.518 (3.95), 2.523 (2.61), 2.539 (2.53), 2.665 (0.68), 2.669 (0.95), 2.673 (0.70), 2.692 (2.05), 2.943 (2.68), 2.974 (2.75), 3.282 (0.67), 3.300 (0.85), 3.317 (0.75), 3.350 (2.90), 3.381 (3.16), 3.447 (1.10), 4.193 (2.90), 4.245 (3.06), 4.323 (2.66), 4.354 (2.58), 6.894 (15.38), 6.899 (4.63), 6.912 (5.13), 6.916 (16.00), 6.924 (1.78), 6.932 (0.65), 6.954 (0.45), 7.536 (0.42), 7.558 (0.43), 7.624 (0.48), 7.646 (0.50), 7.671 (1.83), 7.678 (15.20), 7.695 (4.58), 7.700 (13.69), 7.707 (1.47), 10.561 (4.60). |

The following examples were prepared in analogy to Example 1, Procedure 1.3 using tert-butyl-3,8-diazabicyclo[3.2.1]octane-3-carboxylate:

| Example | Structure IUPAC-Name | LC-MS Data |
|---|---|---|
| 38 | 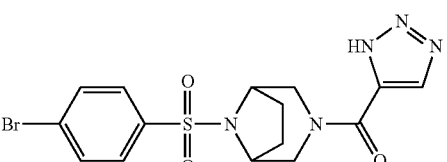 {8-[(4-bromophenyl)sulfonyl]-3,8-diazabicyclo[3.2.1]oct-3-yl}(1H-1,2,3-triazol-5-yl)methanone | LC-MS (Method 4): $R_t$ = 1.02 min; MS (ESIpos): m/z = 427 [M + H]$^+$ |
| 39 | 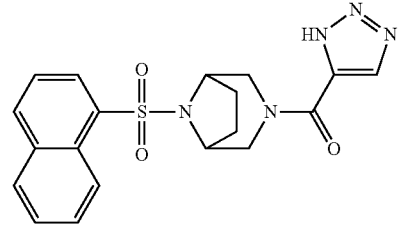 [8-(naphthalen-1-ylsulfonyl)-3,8-diazabicyclo[3.2.1]oct-3-yl](1H-1,2,3-triazol-5-yl)methanone | LC-MS (Method 4): $R_t$ = 1.04 min; MS (ESIpos): m/z = 398 [M + H]$^+$ |
| 40 | 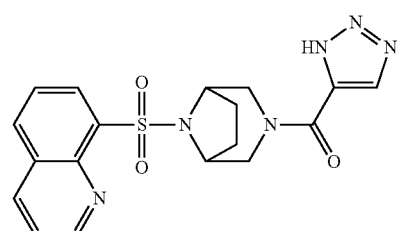 [8-(quinolin-8-ylsulfonyl)-3,8-diazabicyclo[3.2.1]oct-3-yl](1H-1,2,3-triazol-5-yl)methanone | LC-MS (Method 4): $R_t$ = 0.85 min; MS (ESIpos): m/z = 399 [M + H]$^+$ |

| Example | Structure IUPAC-Name | LC-MS Data |
|---|---|---|
| 41 | 1H-1,2,3-triazol-5-yl[8-{[4-trifluoromethoxy)phenyl]sulfonyl}-3,8-diazabicyclo[3.2.1]oct-3-yl]methanone | LC-MS (Method 4): $R_t$ = 1.10 min; MS (ESIpos): m/z = 432 $[M + H]^+$ |
| 42 | 1H-1,2,3-triazol-5-yl[8-{[2-(trifluoromethoxy)phenyl]sulfonyl}-3,8-diazabicyclo[3.2.1]oct-3-yl]methanone | LC-MS (Method 4): $R_t$ = 1.05 min; MS (ESIpos): m/z = 432 $[M + H]^+$ |
| 43 | {8-[(4-nitrophenyl)sulfonyl]-3,8-diazabicyclo[3.2.1]oct-3-yl}(1H-1,2,3-triazol-5-yl)methanone | LC-MS (Method 4): $R_t$ = 0.89 min; MS (ESIpos): m/z = 393 $[M + H]^+$ |
| 44 | {8-[(3-nitrophenyl)sulfonyl]-3,8-diazabicyclo[3.2.1]oct-3-yl}(1H-1,2,3-triazol-5-yl)methanone | LC-MS (Method 4): $R_t$ = 0.88 min; MS (ESIpos): m/z = 393 $[M + H]^+$ |
| 45 | 1H-1,2,3-triazol-5-yl{8-[(2,4,6-trimethylphenyl)sulfonyl]-3,8-diazabicyclo[3.2.1]oct-3-yl}methanone | LC-MS (Method 4): $R_t$ = 1.09 min; MS (ESIpos): m/z = 390 $[M + H]^+$ |

-continued

| Example | Structure IUPAC-Name | LC-MS Data |
|---|---|---|
| 46 | 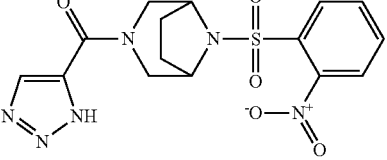<br>{8-[(2-nitrophenyl)sulfonyl]-3,8-diazabicyclo[3.2.1]oct-3-yl}(1H-1,2,3-triazol-5-yl)methanone | LC-MS (Method 4): $R_t$ = 0.87 min; MS (ESIpos): m/z = 393 $[M + H]^+$ |
| 47 | 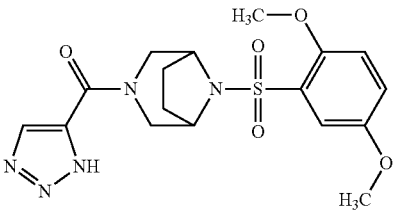<br>{8-[(2,5-dimethoxyphenyl)sulfonyl]-3,8-diazabicyclo[3.2.1]oct-3-yl}(1H-1,2,3-triazol-5-yl)methanone | LC-MS (Method 4): $R_t$ = 0.86 min; MS (ESIpos): m/z = 408 $[M + H]^+$ |
| 48 | 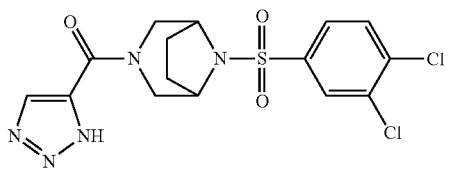<br>{8-[(3,4-dichlorophenyl)sulfonyl]-3,8-diazabicyclo[3.2.1]oct-3-yl}(1H-1,2,3-triazol-5-yl)methanone | LC-MS (Method 4): $R_t$ = 1.08 min; MS (ESIpos): m/z = 417 $[M + H]^+$ |
| 49 | 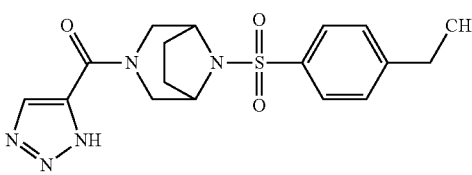<br>{8-[(4-ethylphenyl)sulfonyl]-3,8-diazabicyclo[3.2.1]oct-3-yl}(1H-1,2,3-triazol-5-yl)methanone | LC-MS (Method 4): $R_t$ = 1.01 min; MS (ESIpos): m/z = 376 $[M + H]^+$ |
| 50 | 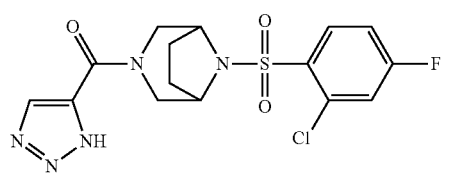<br>{8-[(2-chloro-4-fluorophenyl)sulfonyl]-3,8-diazabicyclo[3.2.1]oct-3-yl}(1H-1,2,3-triazol-5-yl)methanone | LC-MS (Method 4): $R_t$ = 0.97 min; MS (ESIpos): m/z = 401 $[M + H]^+$ |

-continued

| Example | Structure IUPAC-Name | LC-MS Data |
|---|---|---|
| 51 | 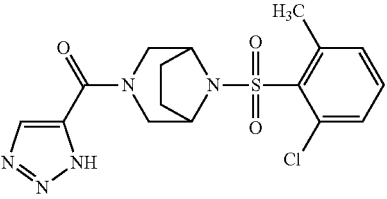 {8-[(2-chloro-6-methylphenyl)sulfonyl]-3,8-diazabicyclo[3.2.1]oct-3-yl}(1H-1,2,3-triazol-5-yl)methanone | LC-MS (Method 4): $R_t$ = 0.99 min; MS (ESIpos): m/z = 397 [M + H]$^+$ |
| 52 | 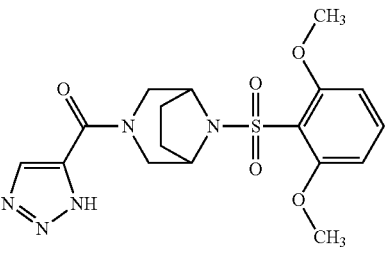 {8-[(3,4-dimethoxyphenyl)sulfonyl]-3,8-diazabicyclo[3.2.1]oct-3-yl}(1H-1,2,3-triazol-5-yl)methanone | LC-MS (Method 4): $R_t$ = 0.81 min; MS (ESIpos): m/z = 408 [M + H]$^+$ |
| 53 | 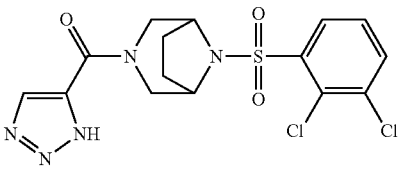 {(1S)-8-[(2,3-dichlorophenyl)sulfonyl]-3,8-diazabicyclo[3.2.1]oct-3-yl}(1H-1,2,3-triazol-5-yl)methanone | LC-MS (Method 4): $R_t$ = 1.03 min; MS (ESIpos): m/z = 417 [M + H]$^+$ |
| 54 | 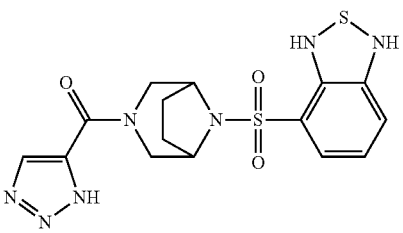 [8-(2,1,3-benzothiadiazol-4-ylsulfonyl)-3,8-diazabicyclo[3.2.1]oct-3-yl](1H-1,2,3-triazol-5-yl)methanone | LC-MS (Method 4): $R_t$ = 0.83 min; MS (ESIpos): m/z = 406 [M + H]$^+$ |
| 55 | 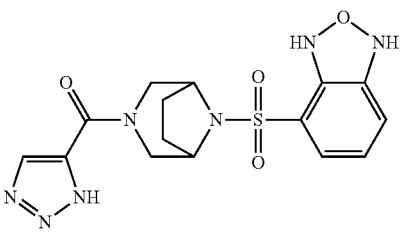 [8-(2,1,3-benzoxadiazol-4-ylsulfonyl)-3,8-diazabicyclo[3.2.1]oct-3-yl](1H-1,2,3-triazol-5-yl)methanone | LC-MS (Method 4): $R_t$ = 0.85 min; MS (ESIpos): m/z = 390 [M + H]$^+$ |

| Example | Structure IUPAC-Name | LC-MS Data |
|---|---|---|
| 56 | 1H-1,2,3-triazol-5-yl{8-[(2,4,6-trichlorophenyl)sulfonyl]-3,8-diazabicyclo[3.2.1]oct-3-yl}methanone | LC-MS (Method 4): $R_t$ = 1.13 min; MS (ESIpos): m/z = 452 $[M + H]^+$ |
| 57 | {8-[(5-chloro-2-methoxyphenyl)sulfonyl]-3,8-diazabicyclo[3.2.1]oct-3-yl}(1H-1,2,3-triazol-5-yl)methanone | LC-MS (Method 4): $R_t$ = 0.97 min; MS (ESIpos): m/z = 413 $[M + H]^+$ |
| 58 | [8-(2,1,3-benzothiadiazol-5-ylsulfonyl)-3,8-diazabicyclo[3.2.1]oct-3-yl](1H-1,2,3-triazol-5-yl)methanone | LC-MS (Method 4): $R_t$ = 0.88 min; MS (ESIpos): m/z = 406 $[M + H]^+$ |
| 59 | 1H-1,2,3-triazol-5-yl{8-[(2,3,4-trifluorophenyl)sulfonyl]-3,8-diazabicyclo[3.2.1]oct-3-yl}methanone | LC-MS (Method 4): $R_t$ = 0.97 min; MS (ESIpos): m/z = 402 $[M + H]^+$ |
| 60 | 2-fluoro-5-{[3-(1H-1,2,3-triazol-5-ylcarbonyl)-3,8-diazabicyclo[3.2.1]oct-8-yl]sulfonyl}benzonitrile | LC-MS (Method 4): $R_t$ = 0.88 min; MS (ESIpos): m/z = 391 $[M + H]^+$ |

| Example | Structure IUPAC-Name | LC-MS Data |
|---|---|---|
| 61 | {8-[(5-chloro-2-fluorophenyl)sulfonyl]-3,8-diazabicyclo[3.2.1]oct-3-yl}(1H-1,2,3-triazol-5-yl)methanone | LC-MS (Method 4): $R_t$ = 0.99 min; MS (ESIpos): m/z = 401 $[M + H]^+$ |
| 62 | 1H-1,2,3-triazol-5-yl{8-[(2,4,5-trifluorophenyl)sulfonyl]-3,8-diazabicyclo[3.2.1]oct-3-yl}methanone | LC-MS (Method 4): $R_t$ = 0.96 min; MS (ESIpos): m/z = 402 $[M + H]^+$ |
| 63 | {8-[(5-chloro-2-methylphenyl)sulfonyl]-3,8-diazabicyclo[3.2.1]oct-3-yl}(1H-1,2,3-triazol-5-yl)methanone | LC-MS (Method 4): $R_t$ = 1.06 min; MS (ESIpos): m/z = 397 $[M + H]^+$ |
| 64 | {8-[(2-methoxyphenyl)sulfonyl]-3,8-diazabicyclo[3.2.1]oct-3-yl}(1H-1,2,3-triazol-5-yl)methanone | LC-MS (Method 4): $R_t$ = 0.83 min; MS (ESIpos): m/z = 378 $[M + H]^+$ |
| 65 | {8-[(5-bromo-2-methylphenyl)sulfonyl]-3,8-diazabicyclo[3.2.1]oct-3-yl}(1H-1,2,3-triazol-5-yl)methanone | LC-MS (Method 4): $R_t$ = 1.08 min; MS (ESIpos): m/z = 441 $[M + H]^+$ |

| Example | Structure IUPAC-Name | LC-MS Data |
|---|---|---|
| 66 | [8-(1,3-benzodioxol-5-ylsulfonyl)-3,8-diazabicyclo[3.2.1]oct-3-yl](1H-1,2,3-triazol-5-yl)methanone | LC-MS (Method 4): $R_t$ = 0.83 min; MS (ESIpos): m/z = 392 [M + H]$^+$ |
| 67 | {8-[(2-methoxy-4-methylphenyl)sulfonyl]-3,8-diazabicyclo[3.2.1]oct-3-yl}(1H-1,2,3-triazol-5-yl)methanone | LC-MS (Method 4): $R_t$ = 0.91 min; MS (ESIpos): m/z = 392 [M + H]$^+$ |
| 68 | 2-chloro-6-{[3-(1H-1,2,3-triazol-5-ylcarbonyl)-3,8-diazabicyclo[3.2.1]oct-8-yl]sulfonyl}benzonitrile | LC-MS (Method 4): $R_t$ = 0.93 min; MS (ESIpos): m/z = 408 [M + H]$^+$ |
| 69 | [8-(2,3-dihydro-1-benzofuran-7-ylsulfonyl)-3,8-diazabicyclo[3.2.1]oct-3-yl](1H-1,2,3-triazol-5-yl)methanone | LC-MS (Method 4): $R_t$ = 0.84 min; MS (ESIpos): m/z = 390 [M + H]$^+$ |
| 70 | {8-[(2-chloro-5-fluorophenyl)sulfonyl]-3,8-diazabicyclo[3.2.1]oct-3-yl}(1H-1,2,3-triazol-5-yl)methanone | LC-MS (Method 4): $R_t$ = 0.97 min; MS (ESIpos): m/z = 401 [M + H]$^+$ |

-continued

| Example | Structure IUPAC-Name | LC-MS Data |
|---|---|---|
| 71 | {8-[(2-chloro-3-fluorophenyl)sulfonyl]-3,8-diazabicyclo[3.2.1]oct-3-yl}(1H-1,2,3-triazol-5-yl)methanone | LC-MS (Method 4): $R_t$ = 0.96 min; MS (ESIpos): m/z = 401 [M + H]$^+$ |
| 72 | {8-[(4-fluoro-2-methoxyphenyl)sulfonyl]-3,8-diazabicyclo[3.2.1]oct-3-yl}(1H-1,2,3-triazol-5-yl)methanone | LC-MS (Method 4): $R_t$ = 0.88 min; MS (ESIpos): m/z = 396 [M + H]$^+$ |
| 73 | 4-methoxy-3-{[3-(1H-1,2,3-triazol-5-ylcarbonyl)-3,8-diazabicyclo[3.2.1]oct-8-yl]sulfonyl}benzonitrile | LC-MS (Method 4): $R_t$ = 0.81 min; MS (ESIpos): m/z = 403 [M + H]$^+$ |
| 74 | 4-chloro-3-{[3-(1H-1,2,3-triazol-5-ylcarbonyl)-3,8-diazabicyclo[3.2.1]oct-8-yl]sulfonyl}benzonitrile | LC-MS (Method 4): $R_t$ = 0.90 min; MS (ESIpos): m/z = 408 [M + H]$^+$ |

Example 75 sodium 5-({8-[(3,5-difluorophenyl)sulfonyl]-3,8-diazabicyclo[3.2.1]oct-3-yl}carbonyl)-1,2,3-triazol-1-ide

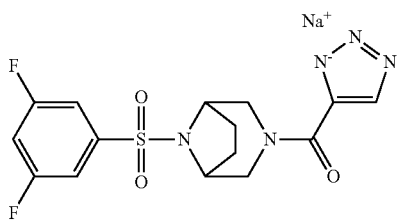 [SMILES: [Na+] ; O=C(c1cnn[n-]1)N1CC2CCC(C1)N2S(=O)(=O)c1cc(F)cc(F)c1]

To a stirred solution of 6.16 g (16 mmol) {8-[(3,5-difluorophenyl)sulfonyl]-3,8-diazabicyclo[3.2.1]oct-3-yl}(1H-1,2,3-triazol-5-yl)methanone in 170 mL MeOH and 70 mL THF were added a solution of sodium methanolate (16 mmol, 1 eq, 30% in MeOH) at RT. After stirring for 2 h at RT, 250 mL diethylether were added to precipitate the product. After cooling and filtration, the solid was dried in vacuo to yield 4.88 g (13 mmol, 87%) of the title compound sodium 5-({8-[(3,5-difluorophenyl)sulfonyl]-3,8-diazabicyclo[3.2.1]oct-3-yl}carbonyl)-1,2,3-triazol-1-ide.

LC-MS (Method 1): Rt=0.93 min; MS (ESIpos): m/z=384 [M-Na$^+$+H]$^+$ $^1$H-NMR (500 MHz, DMSO-d6) δ[ppm]: 1.088 (0.43), 1.255 (3.70), 1.426 (0.96), 1.623 (0.98), 2.361 (0.88), 2.634 (0.81), 2.838 (0.93), 3.172 (0.95), 3.373 (0.48), 4.349 (7.53), 5.654 (0.91), 7.582 (16.00), 7.655 (1.88), 7.660 (1.72), 7.673 (3.97), 7.677 (4.37), 7.690 (7.92), 7.699 (8.03).

Example 76 sodium 5-({8-[(3-fluorophenyl)sulfonyl]-3,8-diazabicyclo[3.2.1]oct-3-yl}carbonyl)-1,2,3-triazol-1-ide

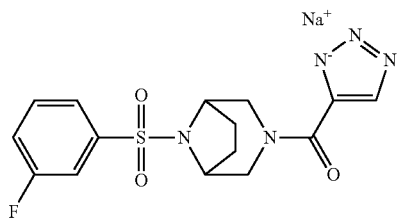 [SMILES: [Na+] ; O=C(c1cnn[n-]1)N1CC2CCC(C1)N2S(=O)(=O)c1cccc(F)c1]

A stirred solution of 4.99 g (13.7 mmol) {8-[(3-fluorophenyl)sulfonyl]-3,8-diazabicyclo[3.2.1]oct-3-yl}(1H-1,2,3-triazol-5-yl)methanone was reacted in analogy to example 75 with sodium methanolate to yield 4.89 g (12.5 mmol, 92%) of the title compound sodium 5-({8-[(3-fluorophenyl)sulfonyl]-3,8-diazabicyclo[3.2.1]oct-3-yl}carbonyl)-1,2,3-triazol-1-ide.

LC-MS: R$_t$=0.88 min; MS (ESIpos): m/z=365 [M-Na$^+$+H]$^+$ $^1$H-NMR (600 MHz, METHANOL-d4) δ [ppm]: −0.005 (1.50), 0.006 (1.47), 1.177 (0.54), 1.442 (3.45), 1.450 (3.48), 1.614 (2.20), 1.628 (3.21), 1.635 (3.51), 1.648 (1.93), 3.055 (1.86), 3.077 (1.92), 3.481 (0.45), 3.493 (0.93), 3.502 (1.89), 3.523 (1.92), 4.253 (2.38), 4.363 (2.38), 4.537 (1.86), 4.558 (2.10), 4.586 (2.10), 4.607 (1.77), 7.409 (1.86), 7.410 (2.05), 7.414 (2.17), 7.415 (2.18), 7.424 (4.26), 7.428 (4.51), 7.429 (4.41), 7.439 (2.31), 7.442 (2.45), 7.443 (2.31), 7.593 (3.06), 7.602 (3.24), 7.607 (5.51), 7.616 (5.57), 7.621 (3.33), 7.630 (3.16), 7.671 (3.28), 7.675 (4.38), 7.678 (3.52), 7.685 (3.35), 7.687 (4.35), 7.692 (3.33), 7.749 (5.52), 7.751 (6.36), 7.754 (5.22), 7.762 (4.66), 7.764 (5.38), 7.765 (5.31), 7.766 (4.19), 7.802 (15.79), 7.803 (16.00), 7.892 (1.93).

EXPERIMENTAL SECTION—BIOLOGICAL ASSAYS

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

AKR1C3-Inhibitory Activity Assay

The AKR1C3-inhibitory activity of the substances of the present invention was measured in the AKR1C3 assay described in the paragraphs below.

Essentially, the enzyme activity is measured by quantification of the generation of Coumberol from Coumberone (Halim et al. J. AM. CHEM. SOC. 2008, 130:14123-14128 and Yee et al. Proc. Natl. Acad. Sci. USA 2006, 103:13304-13309). In this test, the increase of the highly fluorescent Coumberol by NADPH—(nicotinamide adenine dinucleotide phosphate)-dependent reduction of the non-fluorescent Coumberone by AKR1C3 was determined.

The enzyme used was recombinant human AKR1C3 (Aldo-keto reductase family 1 member C3; GenBank Accession No. NM_003739). This was expressed in E. coli as GST (glutathione S transferase) fusion protein and purified by glutathione Sepharose affinity chromatography. The GST was removed by digestion with thrombin and subsequent size exclusion chromatography (Dufort, I., Rheault, P., Huang, X F., Soucy, P., and Luu-The, V., Endocrinology 140, 568-574 (1999)).

For the assay, 50 nl of a 100-fold concentrated solution of the test substance in DMSO were pipetted into a black low-volume 384-well microtiter plate (Greiner Bio-One, Frickenhausen, Germany), 2.5 µl of a solution of AKR1C3 in assay buffer [50 mM potassium phosphate buffer pH 7, 1 mM DTT, 0.0022% (w/v) Pluronic F-127, 0.01% BSA (w/v) and protease inhibitor cocktail (Complete, EDTA-free Protease Inhibitor Cocktail from Roche)] were added and the mixture was incubated for 15 min to allow pre-binding of the substances to the enzyme prior to the enzyme reaction. The enzyme reaction was then started by addition of 2.5 µl of a solution of NADPH (20 µM→final concentration in 5 µl of assay volume is 10 µM) and Coumberone (0.6 µM→final concentration in 5 µl of assay volume is 0.3 µM) in assay buffer, and the resulting mixture was incubated at 22° C. for the reaction time of typically 90 min. The concentration of the AKR1C3 and the reaction time was adapted to the respective activity of the enzyme preparation and adjusted such that the assay was carried out in the linear range. Typical AKR1C3 concentrations were in the region of 1 nM. The reaction was stopped by addition of 2.5 µl of a stop solution consisting of 3 µM EM-1404 as inhibitor (U.S. Pat. No. 6,541,463) in 50 mM HEPES pH7.5 (3 µM EM-1404→final concentration in 7.5 µl of assay volume is 1 µM). The fluorescence of the Coumberole was then measured at 520 nm (excitation at 380 nm) using a suitable measuring instrument (Pherastar from BMG Labtechnologies). The intensity of the fluorescence was used as a measure of the amount of Coumberole formed and thus of the enzyme activity of AKR1C3. The data were normalized (enzyme reaction without inhibitor=0% inhibition; all other assay components, but no enzyme=100% inhibition). Usually, the test substances were tested on the same microtiter plate at 11 different concentrations in the range from 20 µM to 73 pM (20 µM, 5.7 µM, 1.6 µM, 0.47 µM, 0.13 µM, 38 nM, 10.9 nM, 3.1 nM, 0.9 nM, 0.25 nM and 73 pM, the dilution series were prepared prior to the assay on the level of the 100-fold concentrated solution by serial 1:3 dilutions with 100% DMSO) in duplicates for each concentration, and the $IC_{50}$ values were calculated using a 4-parameter fit.

As described, the pharmacological substances claimed were examined for their inhibitory activity on the AKR1C3 enzyme (see table 2). For the major part of the structural range claimed, these substances show strong inhibition of AKR1C3 in vitro with $IC_{50}$ values of less than 10 nM and predominantly even with $IC_{50}$ values around 1 nM.

TABLE 2

AKR1C3-inhibitory activity: $IC_{50}$ values of examples

| Example | $IC_{50}$ human AKR1C3 [nM] |
|---|---|
| 1 | 3.7 |
| 2 | 1.0 |
| 3 | 1.4 |
| 4 | 1.2 |
| 5 | 1.2 |
| 6 | 1.7 |
| 7 | 1.4 |
| 8 | 1.3 |
| 9 | 0.9 |
| 10 | 7.3 |
| 11 | 1.1 |
| 12 | 1.1 |
| 13 | 1.4 |
| 14 | 1.9 |
| 15 | 1.5 |
| 16 | 2.2 |
| 17 | 2.9 |
| 18 | 1.0 |
| 19 | 1.1 |
| 20 | 1.0 |
| 21 | 2.0 |
| 22 | 1.5 |
| 23 | 2.2 |
| 24 | 1.8 |
| 25 | 2.6 |
| 26 | 1.1 |
| 27 | 0.9 |
| 28 | 1.2 |
| 29 | 0.9 |
| 30 | 0.6 |
| 31 | 0.5 |
| 32 | 0.7 |
| 33 | 1.8 |
| 34 | 1.9 |
| 35 | 6.0 |
| 36 | 3.3 |
| 37 | 2.8 |

TABLE 2-continued

AKR1C3-inhibitory activity: $IC_{50}$ values of examples

| Example | $IC_{50}$ human AKR1C3 [nM] |
|---|---|
| 38 | 1.5 |
| 39 | 1.3 |
| 40 | 3.4 |
| 41 | 6.5 |
| 42 | 1.1 |
| 43 | 9.1 |
| 44 | 1.9 |
| 45 | 1.4 |
| 46 | 0.9 |
| 47 | 29.8 |
| 48 | 1.1 |
| 49 | 1.2 |
| 50 | 0.9 |
| 51 | 0.8 |
| 52 | 2.5 |
| 53 | 0.8 |
| 54 | 1.2 |
| 55 | 2.7 |
| 56 | 1.4 |
| 57 | 9.7 |
| 58 | 1.2 |
| 59 | 2.2 |
| 60 | 28.4 |
| 61 | 1.5 |
| 62 | 2.8 |
| 63 | 1.7 |
| 64 | 1.3 |
| 65 | 0.5 |
| 66 | 0.9 |
| 67 | 1.0 |
| 68 | 1.3 |
| 69 | 0.6 |
| 70 | 0.5 |
| 71 | 0.8 |
| 72 | 1.1 |
| 73 | 28.0 |
| 74 | 5.5 |
| 75 | 0.7 |
| 76 | 1.1 |

Compound number 4 in table 1 of WO 2007/111921 (comparative example) was analysed in the same assay to determine the AKR1C3-inhibitory activity of this compound. The $IC_{50}$ of compound number 4 in table 1 of WO 2007/111921 was 1810 nM.

Inhibition of Testosterone Formation from Androstenedione in Human Primary Adipocytes Human primary preadipocytes from 2 donors with a Body Mass Index (BMI) of 26 and 30, respectively were differentiated into mature adipocytes (ordered by ZenBio, Cat# SA-1012-2 12 well Platte; Cat# SA-1012-3 12 well Platte). Adipocytes were incubated in Adipocyte Basal Medium (Fa. ZenBio, Cat# BM-1)+1% FCS+2.5 µg/ml Amphotericin B (Fa. Sigma, Cat# A2942) supplemented with 1 µM androstenedione and 1 µM, 10 µM compound 76 or vehicle for 48 h. Androstenedione served as a substrate for the formation into testosterone. After the incubation adipocytes were collected and testosterone and androstenedione concentrations were determined by LC/MS at the "Bioanalytical Service and research provider Pharm-Analyt". Inhibition of the conversion of androstenedione to testosterone by compound 76 is determined as Testosterone/Androstenedione ratio [%]. That shows that the formation of testosterone from androstenedione is inhibited in human primary adipocytes by compound 76 (see FIG. 1).

*Callithrix jacchus* Endometriosis Model

The in vivo efficacy of compound 76 was tested in a non-human primate endometriosis model in marmoset monkeys.

Marmoset monkeys (*Callithrix jacchus*) are non-menstruating species in which endometriosis was induced by injection of endometrial tissue into the peritoneal cavity (Einspanier, Lieder et al, 2006). 6-12 year old female common marmosets with established endometriosis were employed (body weight between 358 g and 520 g) and distributed into 2 groups, with a size of n=5 animals per group. Prior to the actual start of the treatment, the animals were subjected to a laparotomy and examined for the presence of endometriotic lesions on the bladder, the uterus and the ovaries to measure each lesion's area. The randomization of animals into the two treatment groups was performed with respect to the initial lesion status at the first laparotomy. The endometriosis severity based on total lesion area per animal was distributed similarly across the groups.

For both the treatment group (5 mg/kg of compound 76) and vehicle treated group, the sum of total lesion area/size [cm²] per animal, with respect to lesion area and lesion number, was determined and defined as pre-treatment status. 6 weeks later the treatment was started. The test compounds were administered orally once per day in capsules (PC Caps® capsules, Capsugel). To adapt for the intended dose, a trituration of the active compound with lactose was prepared and the exact dose was filled into the individual capsules. Each capsule was separately coated with *salvia* resistant coating (Eudragit EPO; Evonik). After the end of a 6 weeks treatment period, a second laparotomy was carried out and the number and size of the lesions on uterus, ovaries and bladder was determined with respect to total lesion size/area and defined as post-treatment status.

Total lesion size/area pre-treatment and post-treatment is shown in FIG. 2A. In the vehicle group total lesion size [cm²] increased during the study, while total lesion size was strongly reduced in all animals after 6 weeks treatment with 5 mg/kg of compound 76.

The reduction of total lesion size after treatment is visualized as ratio of total lesion size/area post-versus pre-treatment in the two groups (vehicle group, 5 mg/kg example 76 group). A ratio of 1, corresponds to a stable lesion size. Ratios above 1 show an increase in total lesion size over the course of the experiment, while ratios below 1 show a decrease in total lesion size. The results displayed in FIG. 2A are mirrored in FIG. 2B: All vehicle animals have ratios above 1, while all animals treated with compound 76 have ratios that are below 1. The mean reduction of the total lesion size in the compound 76 treated animals compared to baseline is 68.9%, while there is an increase in the total lesion size compared to baseline in the vehicle treated animals.

Interference with Anthracycline Resistance in Cancer Cells by AKR1C3 Inhibition

A549 lung cancer cells are expressing AKR1C3. A549 cells are plated 24 h prior the start of the experiment. After 24 h the medium is replaced with fresh medium, which contains 1, 10, 50, 100, 200, 500, and 1000 nM daunorubicin, doxorubicin and idarubicin, with or without 1 µM, 10 µM, 30 µM of compound 76. Cell viability is determined following 72 h of incubation at standard conditions (37° C., 5% CO₂). Cell viability is measured by MTT (3-(4,5-Dimethylthiazol-2-yl)-2,5-diphenyltetrazolium-bromid; Sigma-Aldrich) solution in PBS is added to the cells to a final concentration of 1 mg/ml, and the cells are subsequently incubated at standard conditions for 4 h. The medium is aspirated and the cells are lysed with dimethyl sulfoxide on an automatic shaker for 15 min. Absorbance is measured at 570 nm and 690 nm using a microplate reader.

Figure 1:
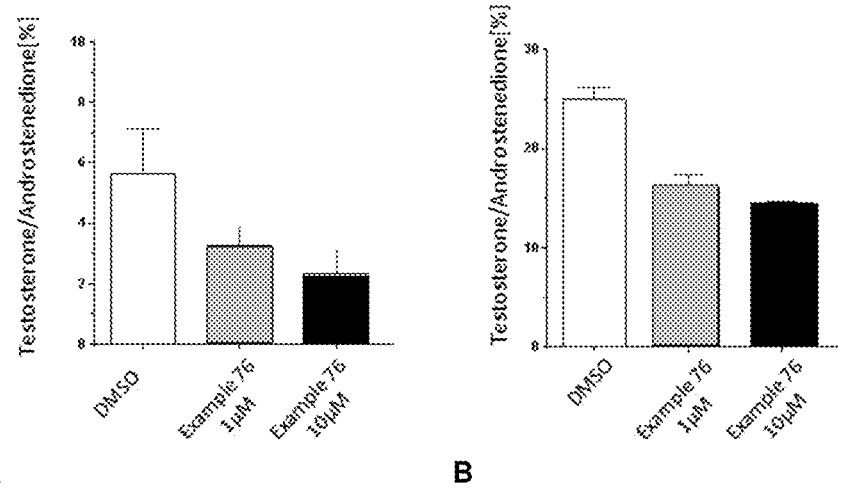
FIG. 1: Conversion of 1 µM androstenedione to testosterone in human primary adipocytes from a donor with a BMI of 26 (A) and a donor with a BMI of 30 (B) after incubation with vehicle (white column), 1 µM compound 76 (grey column), or 10 µM compound 76 (black column). The testosterone/androstenedione ratio [%] is shown.
Figure 2:
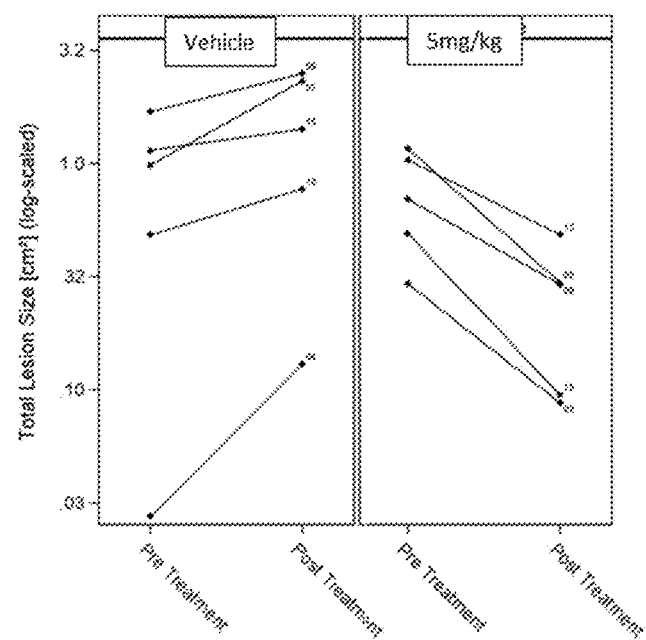
FIG. 2.
Figure 2:
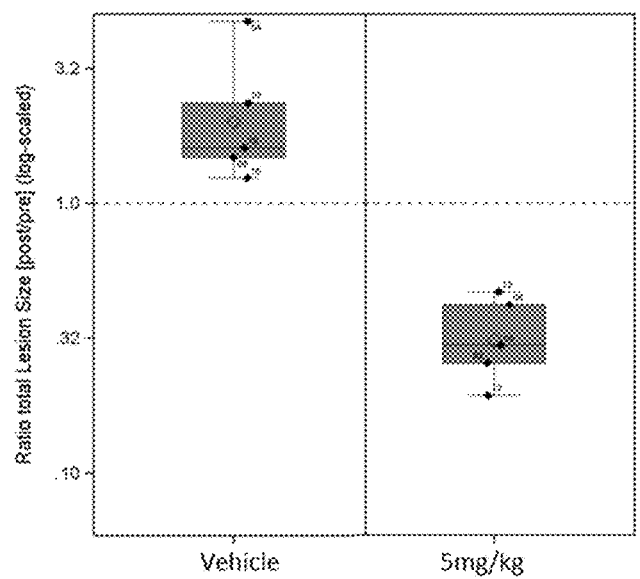

(A) The pre-treatment and post treatment total lesion size of individual marmosets with established endometriosis (n=5) at bladder, ovaries and uterus of the vehicle treated group (left box) and the compound (5 mg/kg of example 76) treated group (right box) is shown.

(B) The ratio of post-/pre-treatment total lesion size at bladder, ovaries and uterus in marmosets with established endometriosis treated with vehicle (left box) or 5 mg/kg of example 76 (right box) is shown. The dotted line represents status at the beginning of the study (first laparotomy).

The invention claimed is:

1. A compound of general formula (I):

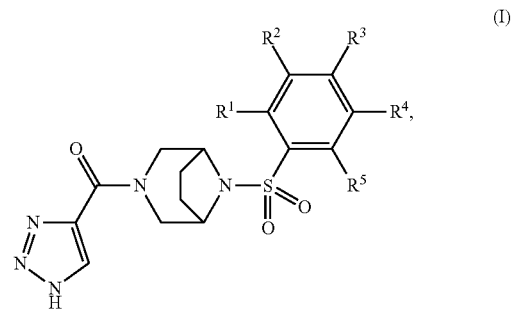

in which:
$R^1$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
$R^2$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
$R^3$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or hydroxy;
$R^4$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;
$R^5$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
wherein $R^1$ and $R^2$ or $R^2$ and $R^3$ are optionally linked to one another in such a way that they jointly form a methylenedioxy, ethylenedioxy, ethyleneoxy, trimethyleneoxy or a group selected from:

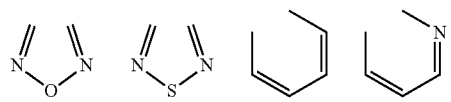

or a stereoisomer, a tautomer, an N-oxide, or a salt thereof, or a mixture of same.

2. The compound according to claim 1, wherein:
$R^1$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro or cyano;
$R^2$ represents hydrogen, halogen, $C_1$-$C_3$-alkyl, $C_1$-$C_3$-haloalkyl, $C_1$-$C_3$-alkoxy, $C_1$-$C_3$-haloalkoxy, nitro, cyano or $SF_5$;

R³ represents hydrogen, halogen, C₁-C₃-alkyl, C₁-C₃-haloalkyl, C₁-C₃-alkoxy, C₁-C₃-haloalkoxy, nitro or hydroxy;

R⁴ represents hydrogen, halogen, C₁-C₃-alkyl, C₁-C₃-haloalkyl, C₁-C₃-alkoxy, C₁-C₃-haloalkoxy, nitro, cyano or SF₅;

R⁵ represents hydrogen, halogen, C₁-C₃-alkyl, C₁-C₃-haloalkyl, C₁-C₃-alkoxy, C₁-C₃-haloalkoxy, nitro or cyano;

or a stereoisomer, a tautomer, an N-oxide, or a salt thereof, or a mixture of same.

3. The compound according to claim 1, wherein:

R¹ represents hydrogen, fluoro, chloro, bromo, methyl, trifluoromethyl, methoxy, trifluoromethoxy or cyano;

R² represents hydrogen, fluoro, chloro, bromo, methyl, trifluoromethyl, methoxy, trifluoromethoxy, cyano or SF₅;

R³ represents hydrogen;

R⁴ represents hydrogen, fluoro, chloro, bromo, methyl, trifluoromethyl, methoxy, trifluoromethoxy, cyano or SF₅;

R⁵ represents hydrogen, fluoro, chloro, bromo, methyl, trifluoromethyl, methoxy, trifluoromethoxy or cyano;

or a stereoisomer, a tautomer, an N-oxide, or a salt thereof, or a mixture of same.

4. The compound according to claim 1, wherein:

R¹ represents hydrogen, fluoro, chloro, bromo, methyl or trifluoromethyl;

R² represents hydrogen, fluoro, chloro, bromo, methyl, trifluoromethyl or SF₅;

R³ represents hydrogen;

R⁴ represents hydrogen, fluoro, chloro, bromo, methyl, trifluoromethyl or SF₅;

R⁵ represents hydrogen, fluoro, chloro, bromo, methyl or trifluoromethyl;

or a stereoisomer, a tautomer, an N-oxide, or a salt thereof, or a mixture of same.

5. The compound according to claim 1, which is selected from the group consisting of:

1  [8-(phenylsulfonyl)-3,8-diazabicyclo[3.2.1]oct-3-yl](1H-1,2,3-triazol-4-yl)methanone;

2  1H-1,2,3-triazol-4-yl[8-{[2-(trifluoromethyl)phenyl]sulfonyl}-3,8-diazabicyclo[3.2.1]oct-3-yl]methanone;

3  {8-[(3,5-difluorophenyl)sulfonyl]-3,8-diazabicyclo[3.2.1]oct-3-yl}(1H-1,2,3-triazol-5-yl)methanone;

4  {8-[(3-fluorophenyl)sulfonyl]-3,8-diazabicyclo[3.2.1]oct-3-yl}(1H-1,2,3-triazol-5-yl)methanone;

5  {8-[(3-chlorophenyl)sulfonyl]-3,8-diazabicyclo[3.2.1]oct-3-yl}(1H-1,2,3-triazol-5-yl)methanone;

6  {8-[(2-methylphenyl)sulfonyl]-3,8-diazabicyclo[3.2.1]oct-3-yl}(1H-1,2,3-triazol-4-yl)methanone;

7  {8-[(2-chlorophenyl)sulfonyl]-3,8-diazabicyclo[3.2.1]oct-3-yl}(1H-1,2,3-triazol-4-yl)methanone;

8  [8-{[3-(pentafluoro-λ⁵-sulfanyl) phenyl]sulfonyl}-3,8-diazabicyclo[3.2.1]oct-3-yl](1H-1,2,3-triazol-4-yl)methanone;

9  {8-[(3,5-dichlorophenyl)sulfonyl]-3,8-diazabicyclo[3.2.1]oct-3-yl}(1H-1,2,3-triazol-4-yl)methanone;

10 [8-{[3,5-bis(trifluoromethyl)phenyl]sulfonyl}-3,8-diazabicyclo[3.2.1]oct-3-yl](1H-1,2,3-triazol-5-yl)methanone;

11 {8-[(5-chlorothiophen-2-yl)sulfonyl]-3,8-diazabicyclo[3.2.1]oct-3-yl}(1H-1,2,3-triazol-4-yl)methanone;

12 {8-[(2,5-difluorophenyl)sulfonyl]-3,8-diazabicyclo[3.2.1]oct-3-yl}(1H-1,2,3-triazol-4-yl)methanone;

13 {8-[(3-methylphenyl)sulfonyl]-3,8-diazabicyclo[3.2.1]oct-3-yl}(1H-1,2,3-triazol-5-yl)methanone;

14 {8-[(4-methylphenyl)sulfonyl]-3,8-diazabicyclo[3.2.1]oct-3-yl}(1H-1,2,3-triazol-5-yl)methanone;

15 {8-[(2-fluorophenyl)sulfonyl]-3,8-diazabicyclo[3.2.1]oct-3-yl}(1H-1,2,3-triazol-5-yl)methanone;

16 {8-[(4-fluorophenyl)sulfonyl]-3,8-diazabicyclo[3.2.1]oct-3-yl}(1H-1,2,3-triazol-5-yl)methanone;

17 3-{[3-(1H-1,2,3-triazol-5-ylcarbonyl)-3,8-diazabicyclo[3.2.1]oct-8-yl]sulfonyl}benzonitrile;

18 {8-[(3,5-dimethylphenyl)sulfonyl]-3,8-diazabicyclo[3.2.1]oct-3-yl}(1H-1,2,3-triazol-5-yl)methanone;

19 {8-[(2,5-dimethylphenyl)sulfonyl]-3,8-diazabicyclo[3.2.1]oct-3-yl}(1H-1,2,3-triazol-5-yl)methanone;

20 {8-[(3-methoxyphenyl)sulfonyl]-3,8-diazabicyclo[3.2.1]oct-3-yl}(1H-1,2,3-triazol-5-yl)methanone;

21 {8-[(4-methoxyphenyl)sulfonyl]-3,8-diazabicyclo[3.2.1]oct-3-yl}(1H-1,2,3-triazol-5-yl)methanone;

22 {8-[(4-chlorophenyl)sulfonyl]-3,8-diazabicyclo[3.2.1]oct-3-yl}(1H-1,2,3-triazol-5-yl)methanone;

23 {8-[(3,4-difluorophenyl)sulfonyl]-3,8-diazabicyclo[3.2.1]oct-3-yl}(1H-1,2,3-triazol-5-yl)methanone;

24 {8-[(2,6-difluorophenyl)sulfonyl]-3,8-diazabicyclo[3.2.1]oct-3-yl}(1H-1,2,3-triazol-5-yl)methanone;

25 {8-[(2,4-difluorophenyl)sulfonyl]-3,8-diazabicyclo[3.2.1]oct-3-yl}(1H-1,2,3-triazol-5-yl)methanone;

26 {8-[(3-chloro-2-methylphenyl)sulfonyl]-3,8-diazabicyclo[3.2.1]oct-3-yl}(1H-1,2,3-triazol-5-yl)methanone;

27 {8-[(3-chloro-2-fluorophenyl)sulfonyl]-3,8-diazabicyclo[3.2.1]oct-3-yl}(1H-1,2,3-triazol-5-yl)methanone;

28 {8-[(3-chloro-4-fluorophenyl)sulfonyl]-3,8-diazabicyclo[3.2.1]oct-3-yl}(1H-1,2,3-triazol-5-yl)methanone;

29 1H-1,2,3-triazol-5-yl[8-{[3-(trifluoromethyl)phenyl]sulfonyl}-3,8-diazabicyclo[3.2.1]oct-3-yl]methanone;

30 {8-[(2,5-dichlorophenyl)sulfonyl]-3,8-diazabicyclo[3.2.1]oct-3-yl}(1H-1,2,3-triazol-5-yl)methanone;

31 {8-[(3-bromophenyl)sulfonyl]-3,8-diazabicyclo[3.2.1]oct-3-yl}(1H-1,2,3-triazol-5-yl)methanone;

32 {8-[(2-bromophenyl)sulfonyl]-3,8-diazabicyclo[3.2.1]oct-3-yl}(1H-1,2,3-triazol-5-yl)methanone;

33 1H-1,2,3-triazol-5-yl[8-{[3-(trifluoromethoxy)phenyl]sulfonyl}-3,8-diazabicyclo[3.2.1]oct-3-yl]methanone;

34 [8-{[5-chloro-2-(trifluoromethyl)phenyl]sulfonyl}-3,8-diazabicyclo [3.2.1]oct-3-yl](1H-1,2,3-triazol-5-yl)methanone;

35 2-{[3-(1H-1,2,3-triazol-5-ylcarbonyl)-3,8-diazabicyclo[3.2.1]oct-8-yl]sulfonyl}benzonitrile;

36 1H-1,2,3-triazol-5-yl[8-{[4-(trifluoromethyl)phenyl]sulfonyl}-3,8-diazabicyclo[3.2.1]oct-3-yl]methanone;

37 {8-[(4-hydroxyphenyl)sulfonyl]-3,8-diazabicyclo[3.2.1]oct-3-yl}(1H-1,2,3-triazol-5-yl)methanone;

38 {8-[(4-bromophenyl)sulfonyl]-3,8-diazabicyclo[3.2.1]oct-3-yl}(1H-1,2,3-triazol-5-yl)methanone;

39 [8-(naphthalen-1-ylsulfonyl)-3,8-diazabicyclo[3.2.1]oct-3-yl](1H-1,2,3-triazol-5-yl)methanone;

40 [8-(quinolin-8-ylsulfonyl)-3,8-diazabicyclo[3.2.1]oct-3-yl](1H-1,2,3-triazol-5-yl)methanone;

41 1H-1,2,3-triazol-5-yl[8-{[4-(trifluoromethoxy)phenyl]sulfonyl}-3,8-diazabicyclo[3.2.1]oct-3-yl]methanone;

42 1H-1,2,3-triazol-5-yl[8-{[2-(trifluoromethoxy)phenyl]sulfonyl}-3,8-diazabicyclo[3.2.1]oct-3-yl]methanone;

43 {8-[(4-nitrophenyl)sulfonyl]-3,8-diazabicyclo[3.2.1]oct-3-yl}(1H-1,2,3-triazol-5-yl)methanone;

44 {8-[(3-nitrophenyl)sulfonyl]-3,8-diazabicyclo[3.2.1]oct-3-yl}(1H-1,2,3-triazol-5-yl)methanone;

45 1H-1,2,3-triazol-5-yl{8-[(2,4,6-trimethylphenyl)sulfonyl]-3,8-diazabicyclo[3.2.1]oct-3-yl}methanone;

46 {8-[(2-nitrophenyl)sulfonyl]-3,8-diazabicyclo[3.2.1]oct-3-yl}(1H-1,2,3-triazol-5-yl)methanone;
47 {8-[(2,5-dimethoxyphenyl)sulfonyl]-3,8-diazabicyclo[3.2.1]oct-3-yl}(1H-1,2,3-triazol-5-yl)methanone;
48 {8-[(3,4-dichlorophenyl)sulfonyl]-3,8-diazabicyclo[3.2.1]oct-3-yl}(1H-1,2,3-triazol-5-yl)methanone;
49 {8-[(4-ethylphenyl)sulfonyl]-3,8-diazabicyclo[3.2.1]oct-3-yl}(1H-1,2,3-triazol-5-yl)methanone;
50 {8-[(2-chloro-4-fluorophenyl)sulfonyl]-3,8-diazabicyclo[3.2.1]oct-3-yl}(1H-1,2,3-triazol-5-yl)methanone;
51 {8-[(2-chloro-6-methylphenyl)sulfonyl]-3,8-diazabicyclo[3.2.1]oct-3-yl}(1H-1,2,3-triazol-5-yl)methanone;
52 {8-[(3,4-dimethoxyphenyl)sulfonyl]-3,8-diazabicyclo[3.2.1]oct-3-yl}(1H-1,2,3-triazol-5-yl)methanone;
53 {(1S)-8-[(2,3-dichlorophenyl)sulfonyl]-3,8-diazabicyclo[3.2.1]oct-3-yl}(1H-1,2,3-triazol-5-yl)methanone;
54 [8-(2,1,3-benzothiadiazol-4-ylsulfonyl)-3,8-diazabicyclo[3.2.1]oct-3-yl](M1H-1,2,3-triazol-5-yl)methanone;
55 [8-(2,1,3-benzoxadiazol-4-ylsulfonyl)-3,8-diazabicyclo[3.2.1]oct-3-yl](1H-1,2,3-triazol-5-yl)methanone;
56 1H-1,2,3-triazol-5-yl{8-[(2,4,6-trichlorophenyl)sulfonyl]-3,8-diazabicyclo[3.2.1]oct-3-yl}methanone;
57 {8-[(5-chloro-2-methoxyphenyl)sulfonyl]-3,8-diazabicyclo[3.2.1]oct-3-yl}(1H-1,2,3-triazol-5-yl)methanone;
58 [8-(2,1,3-benzothiadiazol-5-ylsulfonyl)-3,8-diazabicyclo[3.2.1]oct-3-yl](1H-1,2,3-triazol-5-yl)methanone;
59 1H-1,2,3-triazol-5-yl{8-[(2,3,4-trifluorophenyl)sulfonyl]-3,8-diazabicyclo [3.2.1]oct-3-yl}methanone;
60 2-fluoro-5-{[3-(1H-1,2,3-triazol-5-ylcarbonyl)-3,8-diazabicyclo [3.2.1]oct-8-yl]sulfonyl}benzonitrile;
61 {8-[(5-chloro-2-fluorophenyl)sulfonyl]-3,8-diazabicyclo[3.2.1]oct-3-yl}(1H-1,2,3-triazol-5-yl)methanone;
62 1H-1,2,3-triazol-5-yl{8-[(2,4,5-trifluorophenyl)sulfonyl]-3,8-diazabicyclo[3.2.1]oct-3-yl}methanone;
63 {8-[(5-chloro-2-methylphenyl)sulfonyl]-3,8-diazabicyclo[3.2.1]oct-3-yl}(1H-1,2,3-triazol-5-yl)methanone;
64 {8-[(2-methoxyphenyl)sulfonyl]-3,8-diazabicyclo[3.2.1]oct-3-yl}(1H-1,2,3-triazol-5-yl)methanone;
65 {8-[(5-bromo-2-methylphenyl)sulfonyl]-3,8-diazabicyclo[3.2.1]oct-3-yl}(1H-1,2,3-triazol-5-yl)methanone;
66 [8-(1,3-benzodioxol-5-ylsulfonyl)-3,8-diazabicyclo[3.2.1]oct-3-yl](1H-1,2,3-triazol-5-yl)methanone;
67 {8-[(2-methoxy-4-methylphenyl)sulfonyl]-3,8-diazabicyclo[3.2.1]oct-3-yl}(1H-1,2,3-triazol-5-yl)methanone;
68 2-chloro-6-{[3-(1H-1,2,3-triazol-5-ylcarbonyl)-3,8-diazabicyclo [3.2.1]oct-8-yl]sulfonyl}benzonitrile;
69 [8-(2,3-dihydro-1-benzofuran-7-ylsulfonyl)-3,8-diazabicyclo[3.2.1]oct-3-yl](1H-1,2,3-triazol-5-yl)methanone;
70 {8-[(2-chloro-5-fluorophenyl)sulfonyl]-3,8-diazabicyclo[3.2.1]oct-3-yl}(1H-1,2,3-triazol-5-yl)methanone;
71 {8-[(2-chloro-3-fluorophenyl)sulfonyl]-3,8-diazabicyclo[3.2.1]oct-3-yl}(1H-1,2,3-triazol-5-yl)methanone;
72 {8-[(4-fluoro-2-methoxyphenyl)sulfonyl]-3,8-diazabicyclo[3.2.1]oct-3-yl}(1H-1,2,3-triazol-5-yl)methanone;
73 4-methoxy-3-{[3-(1H-1,2,3-triazol-5-ylcarbonyl)-3,8-diazabicyclo [3.2.1]oct-8-yl]sulfonyl}benzonitrile;
74 4-chloro-3-{[3-(1H-1,2,3-triazol-5-ylcarbonyl)-3,8-diazabicyclo [3.2.1]oct-8-yl]sulfonyl}benzonitrile;
75 sodium 5-({8-[(3,5-difluorophenyl)sulfonyl]-3,8-diazabicyclo[3.2.1]oct-3-yl}carbonyl)-1,2,3-triazol-1-ide; and
76 sodium 5-({8-[(3-fluorophenyl)sulfonyl]-3,8-diazabicyclo[3.2.1]oct-3-yl}carbonyl)-1,2,3-triazol-1-ide;

or a stereoisomer, a tautomer, an N-oxide, or a salt thereof, or a mixture of same.

6. A method of preparing a compound of general formula (I) according to claim 1, said method comprising the step of allowing an intermediate compound of general formula (IV):

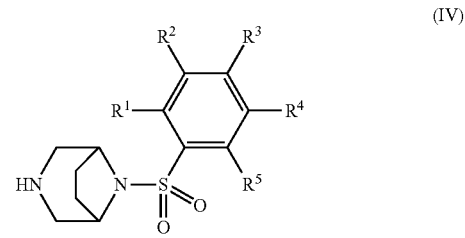

(IV)

in which $R^1$, $R^2$, $R^3$, $R^4$ and $R^5$ are as defined for the compound of general formula (I), to react with a compound of formula (IX):

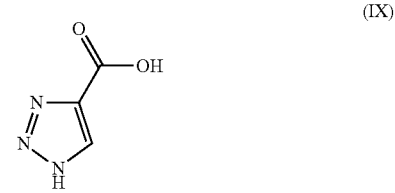

(IX)

thereby giving a compound of general formula (I):

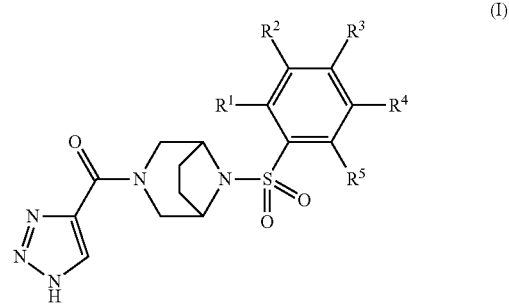

(I)

in which $R^1$, $R^2$, $R^3$, $R^4$ and $R^5$ are as defined for the compound of general formula (I).

7. A method of preparing a compound of general formula (I) according to claim 1, said method comprising the step of allowing an intermediate compound of formula (VII):

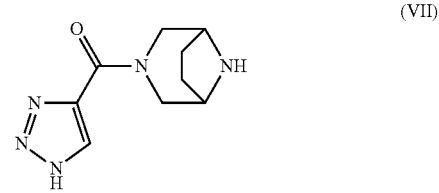

(VII)

to react with a compound of general formula (VIII):

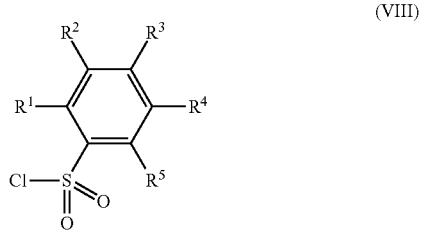
(VIII)

in which R¹, R², R³, R⁴ and R⁵ are as defined for the compound of general formula (I),
thereby giving a compound of general formula (I):

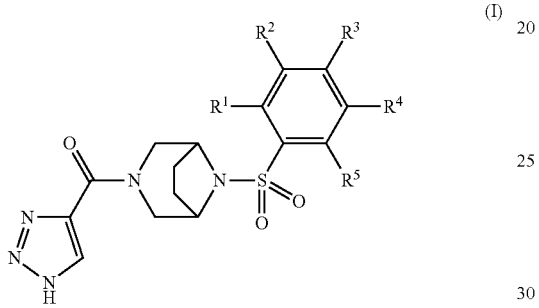
(I)

in which R¹, R², R³, R⁴ and R⁵ are as defined for the compound of general formula (I).

8. A pharmaceutical composition comprising: a compound of general formula (I) according to claim 1, or a stereoisomer, a tautomer, an N-oxide, or a salt thereof; and one or more pharmaceutically acceptable excipients.

9. A pharmaceutical combination comprising:
(a) one or more compounds of general formula (I) according to claim 1, or stereoisomers, tautomers, N-oxides, or salts thereof, or a mixture of same; and
(b) one or more further active ingredients.

10. A pharmaceutical combination according to claim 9, wherein said one or more further active ingredients are selected from the group consisting of anti-androgens, CYP17A1 inhibitors, 5 alpha reductase inhibitors, GNRHa and GNRH antagonists, LHRH agonists for example Flutamide, Bicalutamide, Nilutamide, Enzaluatmide, ODM-201, abiraterone and abiraterone metabolites, finasteride dutasteride, Leuprolide, Goserelin, Triptorelin, Histrelin, and Degarelix.

11. A pharmaceutical combination according to claim 9, wherein a further active ingredient is a chemotherapeutic agent comprising an oxo-group, which can be reduced by the enzymatic activity of AKR1C3.

12. A method of using a compound of general formula (I) according to claim 1 for treatment of a disease; said method comprising administering an effective amount of the compound to a patient.

13. A method of using a combination comprising (a) one or more compounds of general formula (I) according to claim 1, or stereoisomers, tautomers, N-oxides, or salts thereof, or a mixture of same; and (b) one or more further active ingredients for treatment of a disease; said method comprising administering an effective amount of the one or more compounds, stereoisomers, tautomers, N-oxides, salts, or mixture; and the one or more further active ingredients to a patient.

14. The method according to claim 12, wherein the disease is a gynecological disorder; a hyperproliferative disorder; a metabolic disorder; an inflammatory disorder; an endometriosis-related gynecological disorder, condition or disease; a polycystic ovary syndrome-related gynecological disorder, condition or disease; atopic dermatitis; keloids; anthracycline resistant cancer; prostate cancer, or castration-resistant prostate cancer.

15. The method according to claim 13, wherein the disease is a gynecological disorder; a hyperproliferative disorder; a metabolic disorder; an inflammatory disorder; an endometriosis-related gynecological disorder, condition or disease; a polycystic ovary syndrome-related gynecological disorder, condition or disease; atopic dermatitis; keloids; anthracycline resistant cancer; prostate cancer, or castration-resistant prostate cancer.

16. A pharmaceutical combination according to claim 11, wherein the chemotherapeutic agent comprises anthracycline.

17. A compound of general formula (III), (IV) or (VII)

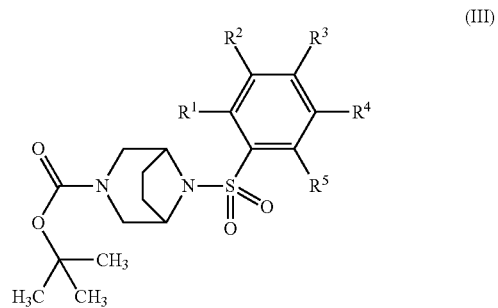
(III)

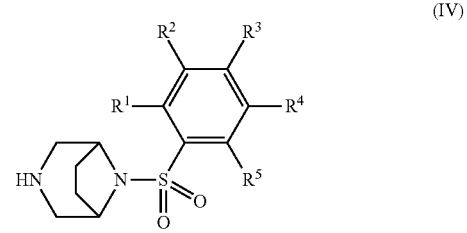
(IV)

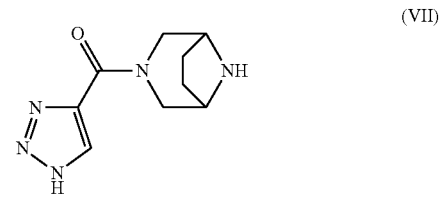
(VII)

in which R¹, R², R³, R⁴ and R⁵ are as defined for a compound of general formula (I) according to claim 1; wherein at least one of R¹, R², R³, R⁴ and R⁵ is different from hydrogen.

18. A method of using a compound of general formula (III), (IV) or (VII) according to claim 17

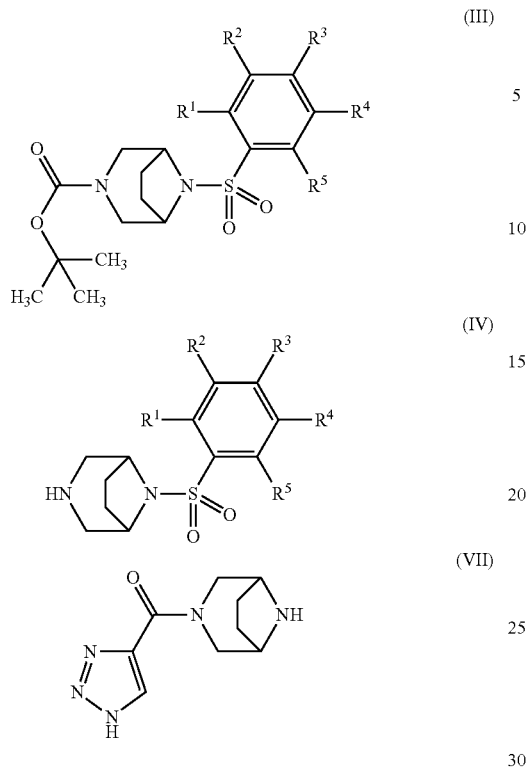
for preparation of the compound of general formula (I).
* * * * *